United States Patent
Williams et al.

(10) Patent No.: US 11,311,622 B2
(45) Date of Patent: Apr. 26, 2022

(54) DEVELOPMENT OF MASKED THERAPEUTIC ANTIBODIES TO LIMIT OFF-TARGET EFFECTS

(71) Applicants: CITY OF HOPE, Duarte, CA (US); Thomas Jefferson University, Philadelphia, PA (US)

(72) Inventors: John C. Williams, Monrovia, CA (US); Cindy Zer, Duarte, CA (US); Kendra N. Avery, Pasadena, CA (US); Ulrich Rodeck, Philadelphia, PA (US); Joshua M. Donaldson, Lumberion, NJ (US); Csaba Kari, Rosemont, CA (US)

(73) Assignees: City of Hope, Duarte, CA (US); Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 16/460,957

(22) Filed: Jul. 2, 2019

(65) Prior Publication Data
US 2020/0164077 A1    May 28, 2020

Related U.S. Application Data

(63) Continuation of application No. 14/949,648, filed on Nov. 23, 2015, now Pat. No. 10,357,571, which is a continuation of application No. 13/424,272, filed on Mar. 19, 2012, now Pat. No. 9,193,791, and a continuation-in-part of application No. 12/849,786, filed on Aug. 3, 2010, now abandoned.

(60) Provisional application No. 61/454,500, filed on Mar. 19, 2011.

(51) Int. Cl.
| *A61K 47/55* | (2017.01) |
| *C07K 16/28* | (2006.01) |
| *C07K 16/30* | (2006.01) |
| *C07K 16/22* | (2006.01) |

(52) U.S. Cl.
CPC .......... *A61K 47/55* (2017.08); *C07K 16/2863* (2013.01); *C07K 16/30* (2013.01); *C07K 2317/31* (2013.01); *C07K 2317/33* (2013.01); *C07K 2317/34* (2013.01); *C07K 2317/622* (2013.01); *C07K 2317/73* (2013.01); *C07K 2317/76* (2013.01); *C07K 2317/92* (2013.01); *C07K 2319/32* (2013.01); *C07K 2319/50* (2013.01)

(58) Field of Classification Search
CPC .... A61K 47/55; C07K 16/2863; C07K 16/30; C07K 16/22; C07K 16/2803; C07K 16/2887; C07K 16/32; C07K 2319/705; C07K 2317/31; C07K 2317/33; C07K 2317/34; C07K 2317/622; C07K 2317/73; C07K 2317/76; C07K 2317/92; C07K 2319/32; C07K 2319/50
See application file for complete search history.

(56) References Cited

U.S. PATENT DOCUMENTS

| 8,895,702 | B2 | 11/2014 | Williams et al. |
| 9,193,791 | B2 | 11/2015 | Williams et al. |
| 10,357,571 | B2 | 7/2019 | Williams et al. |
| 2005/0142133 | A1 | 6/2005 | Lazar et al. |
| 2006/0177448 | A1 | 8/2006 | Carey et al. |
| 2009/0304719 | A1 | 12/2009 | Daugherty et al. |

FOREIGN PATENT DOCUMENTS

WO    WO-02/38796 A2    5/2002

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Yu et al., Investigative Ophthalmology & Visual Science 49(2): 522-527 (Year: 2008).*
Witte et al., Cancer and Metastasis Reviews 17: 155-161 (Year: 1998).*
Cochran et al., J. Immunol. Meth. 287: 147-158 (Year: 2004).*
Stancovski et al., PNAS, 88: 8691-8695 (Year: 1991).*
Adams, G. P., et al., "Monoclonal antibody therapy of cancer," Nat. Biotechnol. 23(9):1147-1157 (2005).
Arkin, M., et al., "A new data analysis method to determine binding constants of small molecules to proteins using equilibrium analytical ultracentrifugation with absorption optics," Anal. Biochem. 299:98-107 (2001).
Backstrom, J. R., et al., "Matrix metalloproteinase-9 (MMP-9) is synthesized in neurons of the human hippocampus and is capable of degrading the amyloid-beta peptide (1-40)," J. Neurosci. 16(24):7910-7919 (1996).
Baselga, J., et al., "Critical update and emerging trends in epidermal growth factor receptor targeting in cancer," J. Clin. Oncol. 23:2445-2459 (2005).
Biscardi, J. S., et al., "Characterization of human epidermal growth factor receptor and c-Src interactions in human breast tumor cells," Molecular Carcinogenesis 21:261-272 (1998).

(Continued)

*Primary Examiner* — Phuong Huynh
(74) *Attorney, Agent, or Firm* — Mintz, Levin, Cohn, Ferris, Glovsky and Popeo, P.C.

(57) ABSTRACT

In one embodiment, a masked monoclonal antibody (mAb) is provided, the mAb, encoded by a nucleic acid sequence or an amino acid sequence molecule comprising a signal sequence, a masking epitope sequence, a linker sequence that is cleavable by a protease specific to a target tissue; and an antibody or a functional fragment thereof. In another embodiment, a masked monoclonal antibody (mAb) is provided, which includes a therapeutic mAb and a mask, the mask comprising protein A and protein L attached by a protease cleavable linker.

5 Claims, 45 Drawing Sheets
Specification includes a Sequence Listing.

(56) References Cited

OTHER PUBLICATIONS

Cox, G., et al., "Matrix Metalloproteinase 9 and the epidermal growth factor signal pathway in operable non-small cell lung cancer," Clin. Cancer Res. 6(6):2349-2355 (2000).
Dechant, M., et al., "Complement-dependent tumor cell lysis triggered by combinations of epidermal growth factor receptor antibodies," Cancer Res. 68(13):4998-5003 (2008).
Delano, W. L., "Unraveling hot spots in binding interfaces: progress and challenges," Curr. Opin. Struct. Biol. 12:14-20 (2002).
Dodson, E. J., et al. "Protein predictions," Nature 450:176-177 (2007).
Ferguson, K.M., "Active and inactive conformations of the epidermal growth factor receptor," Biochem. Soc. Trans. 32(5):742-745 (2004).
Ferguson, K.M., "Extracellular domains drive homo- but not heterodimerization of erbB receptors," Embo J. 19(17):4632-4643 (2000).
Friedman, L. M., et al., "Synergistic down-regulation of receptor tyrosine kinases by combinations of mAbs: Implications for cancer immunotherapy," Proc. Natl. Acad. Sci. 102(6):1915-1920 (2005).
Gill, G. N., et al., "Monoclonal anti-epidermal growth factor receptor antibodies which are inhibitors of epidermal growth factor binding and antagonists of epidermal growth factor binding and antagonists of epidermal growth factor-stimulated tyrosine protein kinase activity," J. Biol. Chem. 259:7755-7760 (1984).
Greenspan, N. S., et al., "Defining epitopes: It's not as easy as it seems," Nat. Biotechnol. 17:936-937 (1999).
Jost, M., et al., "Epidermal growth factor receptor dependent control of keratinocyte survival and Bcl-xL expression through a MEK-dependent pathway," J. Biol. Chem. 276:6320-6326 (2001b).
Jost, M., et al., "Matrix-independent survival of human keratinocytes through an EGF receptor/MAPK-Kinase-dependent pathway," Molecular Biology of the Cell 12:1519-1527 (2001).
Kamat, V., et al., "Enhanced EGFR inhibition and distinct epitope recognition by EGFR antagonistic mAbs C225 and 425," Cancer Biol. Ther. 7(5):726-733 (2008).
Kim, E.S., et al., "Epidermal growth factor receptor biology (IMC-C225)," Curr. Opin. Oncol. 13:506-513 (2001).
Krishnamurthy, V. M., et al., "Dependence of effective molarity on linker length for an intramolecular protein-ligand system," J. Am. Chem. Soc. 129:1312-1320 (2007).
Lacouture, M., E., et al., "Non-rash skin toxicities associated with novel targeted therapies," Clinical Lung Cancer 8(Suppl. 1):S36-S42 (2006).
Landry, R. C., et al., "Antibody recognition of a conformational epitope in a peptide antigen: Fv-peptide complex of an antibody fragment specific for the mutant EGF receptor, EGFRvIII," J. Mol. Biol. 308:883-893 (2001).
Lax, I., et al., "Noncontiguous regions in the extracellular domain of EGF receptor define ligand-binding specificity," Cell Regul. 2:337-345 (1991).
Li, S., et al., "Structural basis for inhibition of the epidermal growth factor receptor by cetuximab," Cancer Cell 7:301-311 (2005).
Lynch, T. J., et al., "Epidermal growth factor receptor inhibitor-associated cutaneous toxicities: An evolving paradigm in clinical management," The Oncologist 12:610-621 (2007).
Masui, H., et al., "Growth inhibition of human tumor cells in athymic mice by anti-epidermal growth factor receptor monoclonal antibodies," Cancer Res. 44:1002-1007 (1984).
Meira, D.D., et al., "Different antiproliferative effects of matuzumab and cetuximab in A431 cells are associated with persistent activity of the MAPK pathway," Eur. J. Cancer 45(7):1265-1273 (2009).
Mendelsohn, J., et al., "The EGF receptor family as targets for cancer therapy," Oncogene 19:6550-6565 (2000).
Moscatello, D. K., et al., "Transformational and altered signal transduction by a naturally occurring mutant EGF receptor," Oncogene 13:85-96 (1996).
Murthy, U., et al., "Binding of an antagonistic monoclonal antibody to an intact and fragmented EGF-receptor polypeptide," Arch. Biochem. Biophys. 252:549-560 (1987).

Nagane, M., et al., "Aberrant receptor signaling in human malignant gliomas: mechanisms and therapeutic implications," Cancer Lett. 162:S17-S21 (2001).
Nahta, R., et al., "The HER-2-Targeting Antibodies Trastuzumab and Pertuzumab Synergistically Inhibit the Survival of Breast Cancer Cells," Cancer Res. 64:2343-2346 (2004).
Ogiso, H., et al., "Crystal structure of the complex of human epidermal growth factor and receptor extracellular domains," Cell 110:775-787 (2002).
Riemer, A. B., et al., "Vaccination with cetuximab mimotopes and biological properties of induced anti-epidermal growth factor receptor antibodies," J. Natl. Cancer Inst. 97(22):1663-1670 (2005).
Rodeck, U., "Skin toxicity caused by EGFR antagonists—An autoinflammatory condition triggered by deregulated IL-1 signaling?" J. Cell Physiol. 218:32-34 (2009).
Rodeck, U., et al., "Tumor growth modulation by a monoclonal antibody to the epidermal growth factor receptor: Immunologically mediated and effector cell-independent effects," Cancer Res. 47:3692-3696 (1987).
Schmiedel, J., et al., "Matuzumab binding to EGFR prevents the conformational rearrangement required for dimerization," Cancer Cell 13:365-373 (2008).
Segaert, S., et al., "Clinical signs, pathophysiology and management of skin toxicity during therapy with epidermal growth factor receptor inhibitors," Annals of Oncology 16:1425-1433 (2005).
Seidman, A., et al., "Cardiac Dysfunction in the trastuzumab clinical trials experience," J. Clin. Oncol. 20:1215-1221 (2002).
Slamon, D. J., et al., "Use of chemotherapy plus a monoclonal antibody against HER2 for metastatic breast cancer that overexpresses HER2," New England Journal of Medicine 344:783-792 (2001).
Spangler, J. B., et al., "Combination antibody treatment down-regulates epidermal growth factor receptor by inhibiting endosomal recycling," Proceedings of the National Academy of Sciences 107:13252-13257 (2010).
Swinson, D.E.B., et al., "Coexpression of epidermal growth factor receptor with related factors is associated with a poor prognosis in non-small-cell lung cancer," British Journal of Cancer 91:1301-1307 (2004).
Tan-Chiu, E., et al., "Assessment of cardiac dysfunction in a randomized trial comparing doxorubicin and cyclophosphamide followed by paclitaxel, with or without trastuzumab as adjuvant therapy in node-positive, human epidermal growth factor receptor 2-overexpressing breast cancer: NSABP B-31," J. Clin. Oncol. 23:7811-7819 (2005).
Thali, M., et al., "Characterization of conserved human immunodeficiency virus type 1 gp120 neutralization epitopes exposed upon gp120-CD4 binding," J. Virol. 67:3978-3988 (1993).
Turk, B. E., et al., "Determination of protease cleavage site motifs using mixture-based oriented peptide libraries," Nat. Biotechnol. 19:661-667 (2001).
Van Cutsem, E., et al., "An open-label, single-arm study assessing safety and efficacy of panitumumab in patients with metastatic colorectal cancer refractory to standard chemotherapy," Annals of Oncology 19:92-98 (2008).
Vanhoefer, U., et al., "Phase I study of the humanized antiepidermal growth factor receptor monoclonal antibody EMD72000 in patients with advanced solid tumors that express the epidermal growth factor receptor," J. Clin. Oncol. 22(1):175-184 (2004).
Wen, X., et al., "Conjugation with (111)In-DTPA-poly(ethylene glycol) improves imaging of anti-EGF receptor antibody C225," J. Nucl. Med. 42:1530-1537 (2001).
Wong, D. T., Neoplasia 2006, 8, (11), 925-932.
Yan, L., et al., "Antibody-based therapy for solid tumors," Cancer J. 14:178-183 (2008).
Yarden, Y., et al., "Untangling the ERBB signaling network," Nat. Rev. Mol. Cell Biol. 2:127-137 (2007).
Zhou, X., et al., "Global expression-based classification of lymph node metastasis and extracapsular spread of oral tongue squamous cell carcinoma," Neoplasia 8(11):925-932 (2006).

\* cited by examiner

Fig. 9A
Masked C225 [ sEGFR dIII | Linker | scFv C225 | H₆ ]
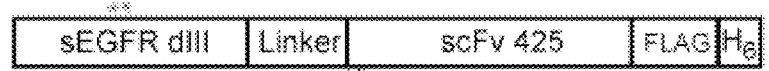
Masked 425 [ sEGFR dIII | Linker | scFv 425 | FLAG | H₆ ]
SEQ ID NO:4  GGGSGGGSGGGS_VPLSLYS_GSTSGSGKSSEGSGSGAQG
                        MMP9
Fig. 9B
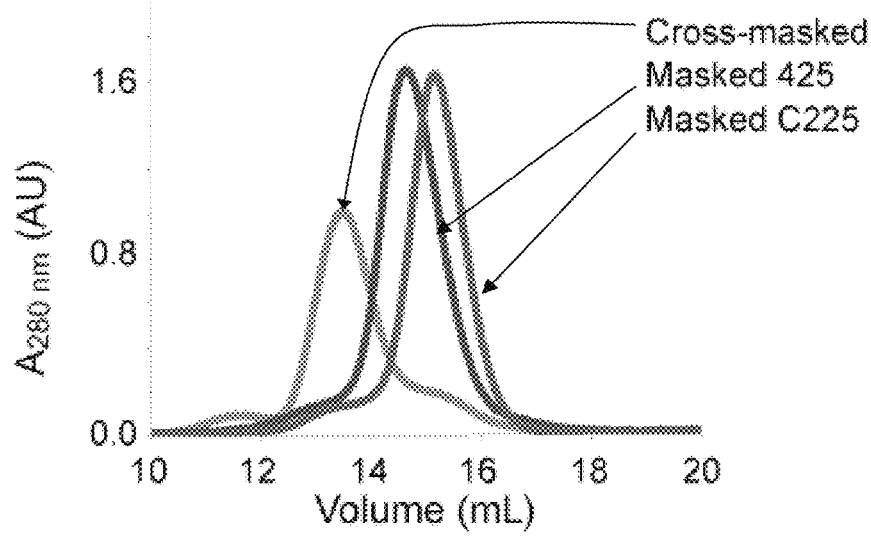
Fig. 9C
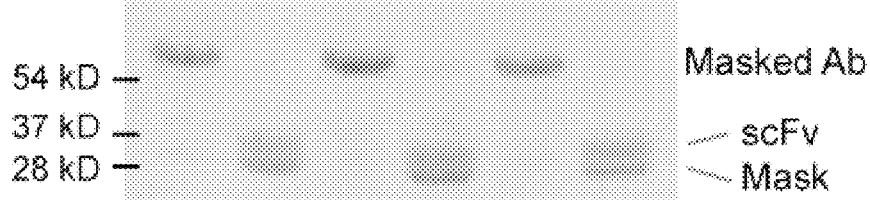

Fig. 14

| Signal Sequence | sEGFRdIII (Q384A/Q408M/H409E)

```
atgcgaccctccgggacggccggggcagcgctcctggcgctgctggctgcgctctgcccggcgagtcgagctcgcaaagtgtgtaac
 M   R   P   S   G   T   A   G   A   A   L   L   A   L   L   A   A   L   C   P   A   S   R   A   R   K   V   C   N
```

```
ggaataggtattggtgaatttaaagactcactctccataaatgctacgaatattaaacacttcaaaaactgcacctccatcagtggc
 G   I   G   I   G   E   F   K   D   S   L   S   I   N   A   T   N   I   K   H   F   K   N   C   T   S   I   S   G
```

```
gatctccacatcctgccggtggcatttaggggtgactccttcacacatactcctcctctggatccacaggaactggatattctgaaa
 D   L   H   I   L   P   V   A   F   R   G   D   S   F   T   H   T   P   P   L   D   P   Q   E   L   D   I   L   K
```

```
accgtaaaggaaatcacagggttttttgctgattgcggcttggcctgaaaaccgtacggacctccatgcctttgagaacctagaaatc
 T   V   K   E   I   T   G   F   L   L   I   A   A   W   P   E   N   R   T   D   L   H   A   F   E   N   L   E   I
```

```
atacgcggcaggaccaagatggagggtcagtttctcttgcagtcgtcagcctgaacataacatccttgggattacgctccctcaag
 I   R   G   R   T   K   M   E   G   Q   F   S   L   A   V   V   S   L   N   I   T   S   L   G   L   R   S   L   K
```

```
gagataagtgatggagatgtgataatttcaggaaacaaaaatttgtgctatgcaaatacaataaactggaaaaaactgtttgggacc
 E   I   S   D   G   D   V   I   I   S   G   N   K   N   L   C   Y   A   N   T   I   N   W   K   K   L   F   G   T
```

```
tccggtcagaaaaccaaaattataagcaatagaggtgaaaacagctgcaaggccacaggccaggtctgccatgccttgtgctcccc
 S   G   Q   K   T   K   I   I   S   N   R   G   E   N   S   C   K   A   T   G   Q   V   C   H   A   L   C   S   P
```
| Linker 1
```
gagggctgctggggcccggagcccaaggactgcgtctcttgccggaatgtcagccgaggcagggaatgctgttctagaggtggtgga
 E   G   C   W   G   P   E   P   K   D   C   V   S   C   R   N   V   S   R   G   R   E   C   C   S   R   G   G   G
```
| MMP-9 Site      | Linker 2
```
agtggtggaggatctggaggaggtagcgttcctctgagcctgtacagcggaagcaccagtggcagcggtaagagcagcgagggaagc
 S   G   G   G   S   G   G   G   S   V   P   L   S   L   Y   S   G   S   T   S   G   S   G   K   S   S   E   G   S
```
| scFv C225 $V_L$
```
ggaagcggggcccaaggagatatttttgctgactcagtctccagtcatcctgtctgtgagtccaggagaaagagtcagtttctcctgc
 G   S   G   A   Q   G   D   I   L   L   T   Q   S   P   V   I   L   S   V   S   P   G   E   R   V   S   F   S   C
```

```
agggctagtcagagtattggcacaaacatacactggtatcagcaaagaacaaatggttctccaaggttgctcataaagtatgcttcg
 R   A   S   Q   S   I   G   T   N   I   H   W   Y   Q   Q   R   T   N   G   S   P   R   L   L   I   K   Y   A   S
```

```
gagtctatctctggcatcccttcgaggtttagtggcagtggatcaggtacagattttactctaagcatcaacagtgtggagtctgaa
 E   S   I   S   G   I   P   S   R   F   S   G   S   G   S   G   T   D   F   T   L   S   I   N   S   V   E   S   E
```
| Linker 3
```
gatattgcagattattattgccaacaaaacaacaactggccaaccacgttcggtgctggaaccaagctggagctgaaacgttctggt
 D   I   A   D   Y   Y   C   Q   Q   N   N   N   W   P   T   T   F   G   A   G   T   K   L   E   L   K   R   S   G
```
| scFv C225 $V_H$
```
tctacgtctggatcgggtaaaccgggttcgggtgaaggttcgacgaaaggacaggtgcagctgaagcagtcaggacctggcctagtg
 S   T   S   G   S   G   K   P   G   S   G   E   G   S   T   K   G   Q   V   Q   L   K   Q   S   G   P   G   L   V
```

```
cagccctcacagagcctgtccatcacctgcacagtctctggtttctcattaactaactatggtgtacactgggttcgccagtctcca
 Q   P   S   Q   S   L   S   I   T   C   T   V   S   G   F   S   L   T   N   Y   G   V   H   W   V   R   Q   S   P
```

```
ggaaagggtctggagtggctgggagtgatatggagtggtggaaacacagactataatacacctttcacatccagactgagcatcaac
 G   K   G   L   E   W   L   G   V   I   W   S   G   G   N   T   D   Y   N   T   P   F   T   S   R   L   S   I   N
```

```
aaggacaattccaagagccaagtttttcttcaagatgaacagcctgcagagcaatgacacagccatatattactgtgccagagccctc
 K   D   N   S   K   S   Q   V   F   F   K   M   N   S   L   Q   S   N   D   T   A   I   Y   Y   C   A   R   A   L
```

Fig. 14 (cont'd)

*Hexahistadine Tag* acctactatgattacgagtttgcttactggggccaaggtactctggtcactgtctctgagaccggtcatcatcaccatcaccattga
 T  Y  Y  D  Y  E  F  A  Y  W  G  Q  G  T  L  V  T  V  S  E  T  G  H  H  H  H  H  H  *

Fig. 15

| Signal Sequence | | sEGFRdIII (S460P/G461N)

atgcgaccctccgggacggccggggcagcgctcctggcgctgctggctgcgctctgcccggcgagtcgagctcgcaaagtgtgtaac
M　R　P　S　G　T　A　G　A　A　L　L　A　L　L　A　A　L　C　P　A　S　R　A　R　K　V　C　N ggaataggtattggtgaatttaaagactcactctccataaatgctacgaatattaaacacttcaaaaactgcacctccatcagtggc
G　I　G　I　G　E　F　K　D　S　L　S　I　N　A　T　N　I　K　H　F　K　N　C　T　S　I　S　G gatctccacatcctgccggtggcatttagggggtgactccttcacacatactcctcctctggatccacaggaactggatattctgaaa
D　L　H　I　L　P　V　A　F　R　G　D　S　F　T　H　T　P　P　L　D　P　Q　E　L　D　I　L　K accgtaaaggaaatcacagggttttttgctgattgcggcttggcctgaaaaccgtacggacctccatgcctttgagaacctagaaatc
T　V　K　E　I　T　G　F　L　L　I　A　A　W　P　E　N　R　T　D　L　H　A　F　E　N　L　E　I atacgcggcaggaccaagatggagggtcagtttctcttgcagtcgtcagcctgaacataacatccttgggattacgctccctcaag
I　R　G　R　T　K　M　E　G　Q　F　S　L　A　V　V　S　L　N　I　T　S　L　G　L　R　S　L　K gagataagtgatggagatgtgataatttcaggaaacaaaaatttgtgctatgcaaatacaataaactggaaaaaactgtttgggacc
E　I　S　D　G　D　V　I　I　S　G　N　K　N　L　C　Y　A　N　T　I　N　W　K　K　L　F　G　T tccggtcagaaaaccaaaattataagcaatagaggtgaaaacagctgcaaggccacaggccaggtctgccatgccttgtgctcccc
S　G　Q　K　T　K　I　I　S　N　R　G　E　N　S　C　K　A　T　G　Q　V　C　H　A　L　C　S　P
　　　　　　　　　　　　　　　　　　　　　　　　　　　　　　　　　　　　　　　　　　　| Linker 1 gagggctgctggggcccggagcccaaggactgcgtctcttgccggaatgtcagccgaggcagggaatgctgttctagaggtggtgga
E　G　C　W　G　P　E　P　K　D　C　V　S　C　R　N　V　S　R　G　R　E　C　C　S　R　G　G　G
　　　　　　　　　　　　　　| MMP-9 Site　　　　　　　　　| Linker 2 agtggtggaggatctggaggaggtagcgttcctctgagcctgtacagcggaagcaccagtggcagcggtaagagcagcgagggaagc
S　G　G　G　S　G　G　G　S　V　P　L　S　L　Y　S　G　S　T　S　G　S　G　K　S　S　E　G　S
　　　　　| scFv 425 V$_L$ ggaagcggggcccaaggagagctcgtcatgacccagtctccagcaatcatgtctgcatctccaggggagaaggtcactatgacctgc
G　S　G　A　Q　G　E　L　V　M　T　Q　S　P　A　I　M　S　A　S　P　G　E　K　V　T　M　T　C agtgccagctcaagtgtaacttacatgtattggtaccagcagaagccaggatcctcccccagactcctgatttatgacacatccaac
S　A　S　S　S　V　T　Y　M　Y　W　Y　Q　Q　K　P　G　S　S　P　R　L　L　I　Y　D　T　S　N ctggcttctggagtccctgttcgtttcagtggcagtgggtctgggacctcttactctctcacaatcagccgaatggaggctgaagat
L　A　S　G　V　P　V　R　F　S　G　S　G　S　G　T　S　Y　S　L　T　I　S　R　M　E　A　E　D
　　　　　　　　　　　　　　　　　　　　　　　　　　　　　　　　　　　　　　　| Linker 3 gctgccacttattactgccagcagtggagtagtcacatattcacgttcggctcggggacaaagttggaaataaaaggtggtggtggt
A　A　T　Y　Y　C　Q　Q　W　S　S　H　I　F　T　F　G　S　G　T　K　L　E　I　K　G　G　G　G
　　　　　　　　　　　　　　　　　| scFv 425 V$_H$ tctggcggcggcgctccggtggtggtggttctcaggtccagttggtcgagtctggagctgaactggtgaagcctggggcttcagtg
S　G　G　G　G　S　G　G　G　G　S　Q　V　Q　L　V　E　S　G　A　E　L　V　K　P　G　A　S　V aagttgtcctgcaaggcttccggctacaccttcaccagccactggatgcactgggtgaagcagagggctggacaaggccttgagtgg
K　L　S　C　K　A　S　G　Y　T　F　T　S　H　W　M　H　W　V　K　Q　R　A　G　Q　G　L　E　W atcggagagtttaatccagcaacggccgtactaactacaatgagaaattcaagagcaaggccacactgactgtagacaaatcctcc
I　G　E　F　N　P　S　N　G　R　T　N　Y　N　E　K　F　K　S　K　A　T　L　T　V　D　K　S　S

Figure 15 (cont'd)

```
agcacagcctacatgcaactcagcagcctgacatctgaggactctgcggtctattactgtgccagtcgggactatgattacgacgga
 S  T  A  Y  M  Q  L  S  S  L  T  S  E  D  S  A  V  Y  Y  C  A  S  R  D  Y  D  Y  D  G
                                               | Flag Tag                    | Hexahistadine
```
```
cggtactttgactactggggccaaggcaccactctcacagtctccgactacaaagacgatgacgataaaaccggtcatcatcaccat
 R  Y  F  D  Y  W  G  Q  G  T  T  L  T  V  S  D  Y  K  D  D  D  K  T  G  H  H  H  H
Tag
```
```
caccattga
 H  H  *
```

Fig. 16A
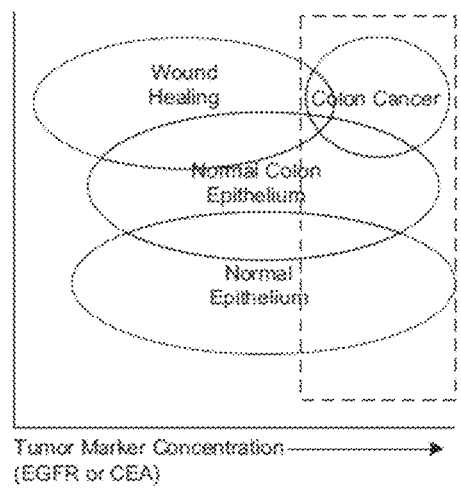
*Current Antibody Selectivity*
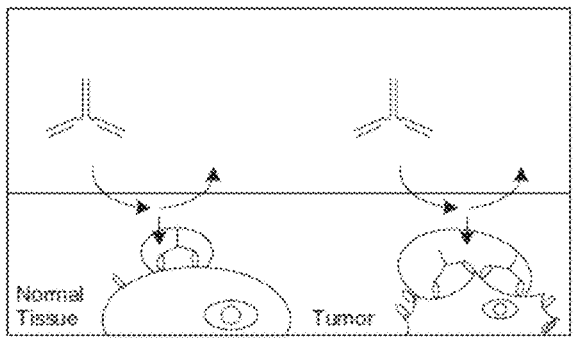
Fig. 16B
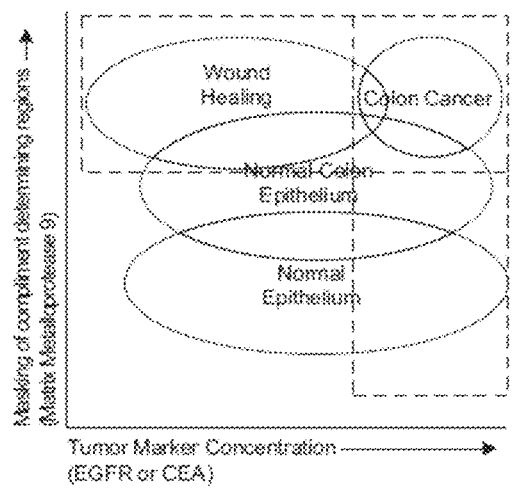
*Enhanced Antibody Selectivity by Masking*
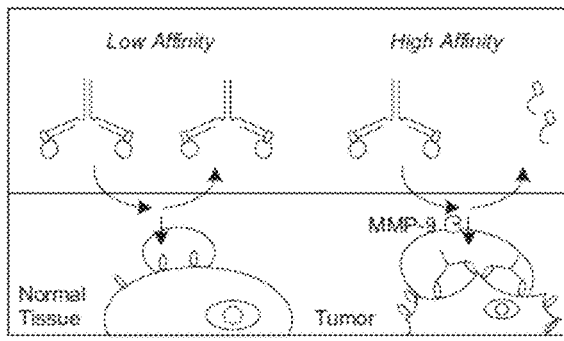

*Masked scFvC225*

SEQ ID NO:9

$V_L$-GGGGSGGGGSGGGGS-$V_H$

Sacl (Q384A/Q408M/H409E) Xbal Apal Agel

Sig Seq — dEGFR domain3 — Linker — scFv C225 — H$_6$

SEQ ID NO:4  GGGSGGGSGGGS-VPLSLYS-GSTSGSGKSSEGSGSGAQG
MMP-9 Cleavage Site

*Masked scFv425*

SEQ ID NO:9

$V_L$-GGGGSGGGGSGGGGS-$V_H$

Sacl (S460P/G461N) Xbal Apal Agel

Sig Seq — dEGFR domain3 — Linker — scFv 425 — FLAG — H$_6$

SEQ ID NO:4  GGGSGGGSGGGS-VPLSLYS-GSTSGSGKSSEGSGSGAQG
MMP-9 Cleavage Site

Fig. 17

Fig. 34A
Fig. 34B
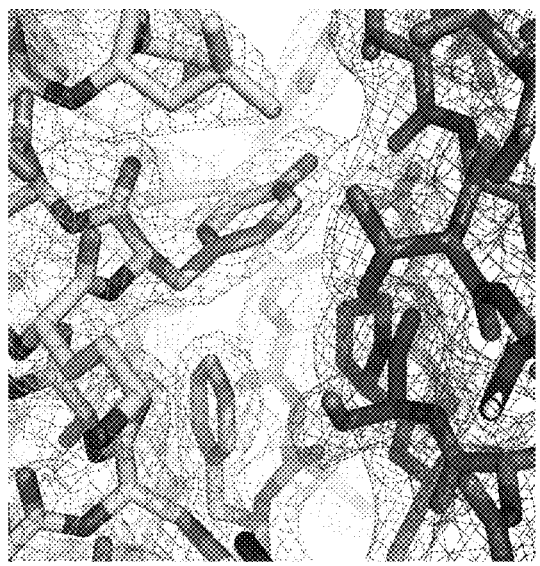
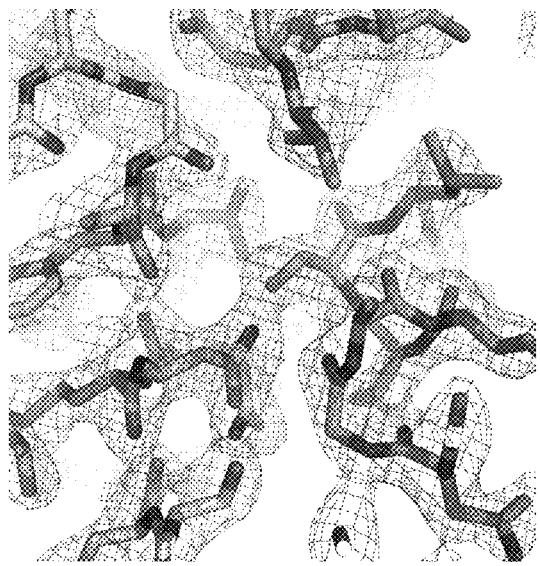
Fig. 34C
Fig. 34D
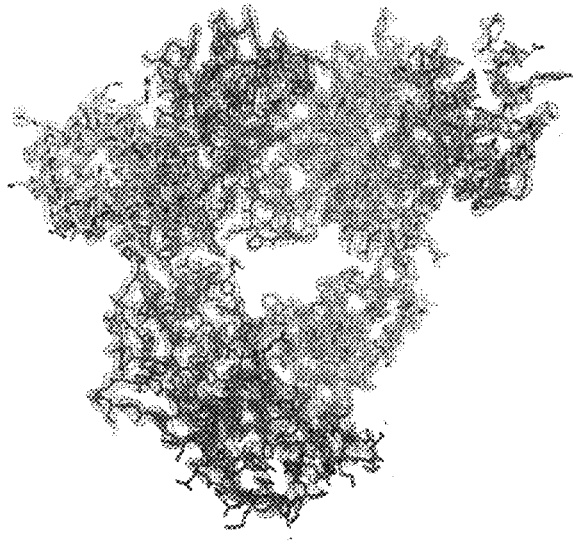

| Complex | |
|---|---|
| Data collection | |
| Space group | P212121 |
| Cell dimensions | |
| $\quad$ a, b, c (Å) | 53.6 104.8 117.7 |
| $\quad$ α, β, γ (°) | 90.00, 90.00, 90.00 |
| Resolution (Å) | 40 - 2.1 (2.2-2.1) |
| $R$mrgd-F | 0.063 (0.37) |
| $I / \sigma(I)$ | 14.7 (3.2) |
| Completeness (%) | 98.8 (93.0) |
| Redundancy | 4.1 (3.3) |
| Multivariate Z score | |
| L-test: | 0.040 |
| | |
| Refinement | |
| Resolution (Å) | 37 - 2.1 |
| No. reflections | 76074 |
| $R$work / $R$free (5%) | 19.1/23.6 |
| No. atoms | |
| $\quad$ Protein | 4151 |
| $\quad$ Water | 374 |
| $B$-factors | |
| $\quad$ Protein | |
| $\quad\quad$ HC | 35.6 |
| $\quad\quad$ LC | 34.8 |
| $\quad\quad$ Prot A | 37.7 |
| $\quad\quad$ Prot L | 43.0 |
| $\quad$ Water | 38.5 |
| r.m.s.d. | |
| $\quad$ Bond lengths (Å) | 0.018 |
| $\quad$ Bond angles (°) | 1.6 |
| Ramachandran | |
| $\quad$ favored / outliers | 97.4% / 0.2% |

Fig. 35

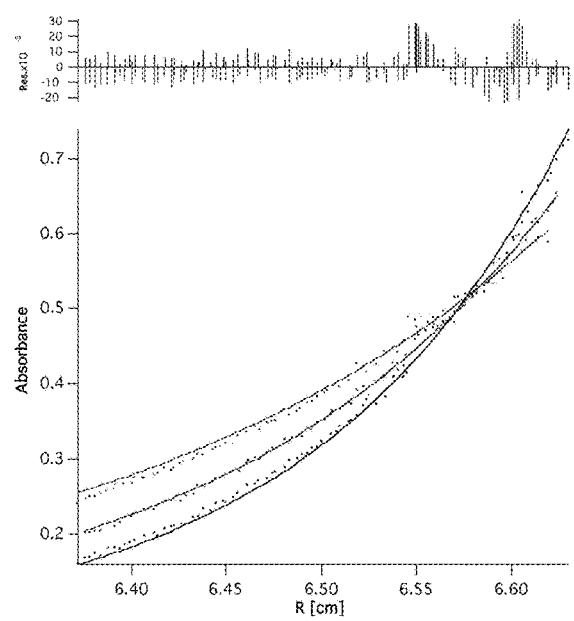
Fig. 36B. protein A-protein L mask
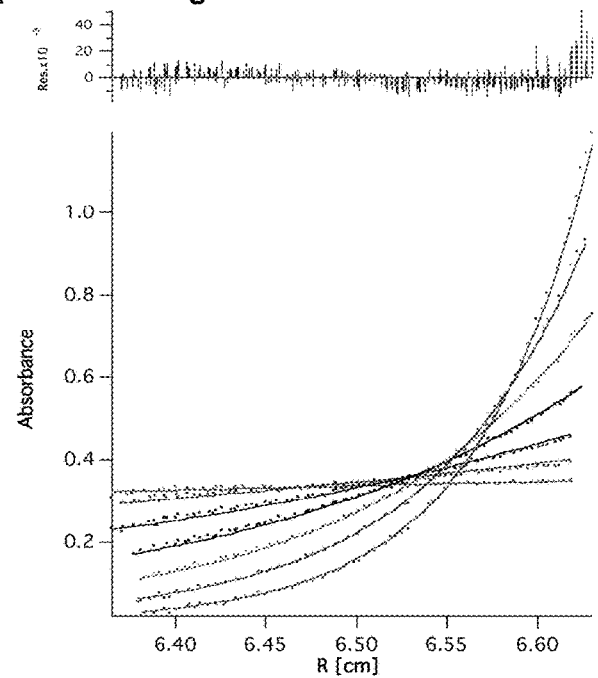
Fig. 36C. trastuzumab fab
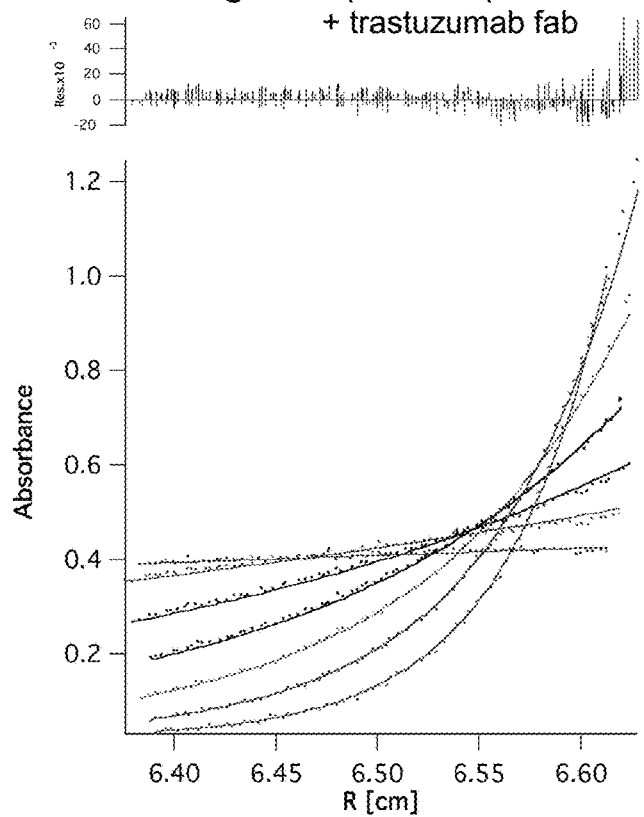
Fig. 36D. protein A-protein L mask + trastuzumab fab

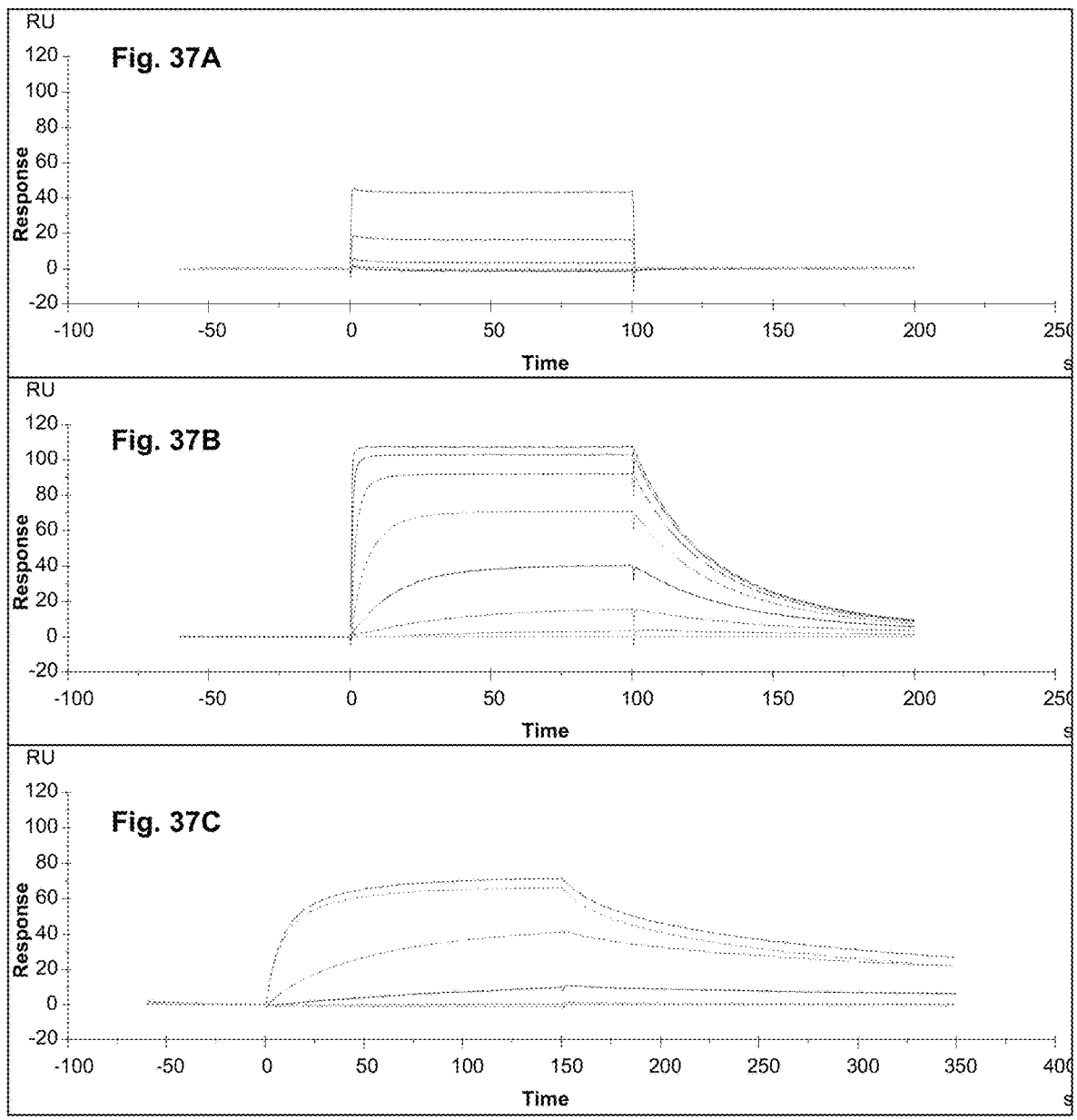

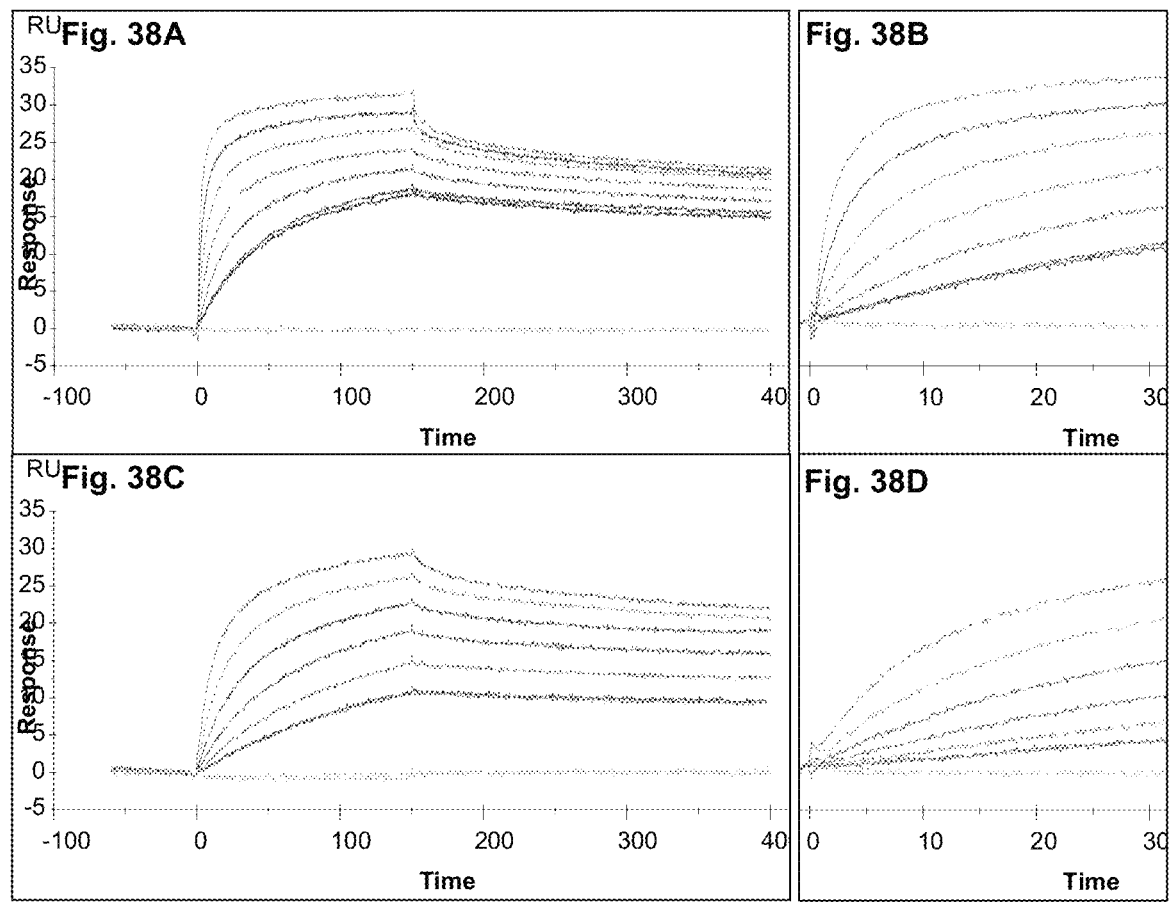

SEQUENCE LISTING

<160> NUMBER OF SEQ ID NOS: 11

<210> SEQ ID NO 1
<211> LENGTH: 1566
<212> TYPE: DNA
<213> ORGANISM: Artificial Sequence
<220> FEATURE:
<223> OTHER INFORMATION: Synthetic construct

<400> SEQUENCE: 1

```
atgcgaccct ccgggacggc cggggcagcg ctcctggcgc tgctggctgc gctctgcccg      60
gcgagtcgag ctcgcaaagt gtgtaacgga ataggtattg gtgaatttaa agactcactc     120
tccataaatg ctacgaatat taaacacttc aaaaactgca cctccatcag tggcgatctc     180
cacatcctgc cggtggcatt taggggtgac tccttcacac atactcctcc tctggatcca     240
caggaactgg atattctgaa aaccgtaaag gaaatcacag ggttttttgct gattgcggct     300 tggcctgaaa accgtacgga cctccatgcc tttgagaacc tagaaatcat acgcggcagg     360
accaagatgg agggtcagtt ttctcttgca gtcgtcagcc tgaacataac atccttggga     420
ttacgctccc tcaaggagat aagtgatgga gatgtgataa tttcaggaaa caaaaatttg     480
tgctatgcaa atacaataaa ctggaaaaaa ctgtttggga cctccggtca gaaaaccaaa     540
attataagca atagaggtga aaacagctgc aaggccacag gccaggtctg ccatgccttg     600
tgctcccccg agggctgctg gggccgagag cccaaggact cgtctcttg ccggaatgtc     660 agccgaggca gggaatgctg ttctagaggt ggtggaagtg gtggaggatc tggaggaggt     720
agcgttcctc tgagcctgta cagcggaagc accagtggca gcggtaagag cagcgaggga     780
agcggaagcg gggcccaagg agatattttg ctgactcagt ctccagtcat cctgtctgtg     840
agtccaggag aaagagtcag tttctcctgc agggctagtc agagtattgg cacaaacata     900
cactggtatc agcaaagaac aaatggttct ccaaggttgc tcataaagta tgcttcggag     960
tctatctctg gcatcccttc gaggtttagt ggcagtggat caggtacaga ttttactcta    1020
agcatcaaca gtgtggagtc tgaagatatt gcagattatt attgccaaca aaacaacaac    1080
tggccaacca cgttcggtgc tggaaccaag ctggagctga acgttctgg ttctacgtct    1140 ggatcgggta aaccgggttc gggtgaaggt tcgacgaaag gacaggtgca gctgaagcag    1200
tcaggacctg gcctagtgca gccctcacag agcctgtcca tcacctgcac agtctctggt    1260
ttctcattaa ctaactatgg tgtacactgg gttcgccagt ctccaggaaa gggtctggag    1320
tggctgggag tgatatggag tggtggaaac acagactata atacacnctt cacatccaga    1380
ctgagcatca caaggacaa ttccaagagc caagttttct tcaagatgaa cagcctgcag    1440
agcaatgaca cagccatata ttactgtgcc agagccctca cctactatga ttacgagttt    1500
gcttactggg gccaaggtac tctggtcact gtctctgaga ccgtcatca tcaccatcac    1560 cattga                                                              1566
```

<210> SEQ ID NO 2
<211> LENGTH: 1575
<212> TYPE: DNA
<213> ORGANISM: Artificial Sequence
<220> FEATURE:
<223> OTHER INFORMATION: Synthetic construct

<400> SEQUENCE: 2

| | | | | | |
|---|---|---|---|---|---|
| atgcgaccct | ccgggacggc | cggggcagcg | ctcctggcgc | tgctggctgc | gctctgcccg | 60 |
| gcgagtcgag | ctcgcaaagt | gtgtaacgga | ataggtattg | gtgaatttaa | agactcactc | 120 |
| tccataaatg | ctacgaatat | taaacacttc | aaaaactgca | cctccatcag | tggcgatctc | 180 |
| cacatcctgc | cggtggcatt | tagggggtgac | tccttcacac | atactcctcc | tctggatcca | 240 |
| caggaactgg | atattctgaa | aaccgtaaag | gaaatcacag | ggttttttgct | gattgcggct | 300 |
| tggcctgaaa | accgtacgga | cctccatgcc | tttgagaacc | tagaaatcat | acgcggcagg | 360 |
| accaagatgg | agggtcagtt | ttctcttgca | gtcgtcagcc | tgaacataac | atccttggga | 420 |
| ttacgctccc | tcaaggagat | aagtgatgga | gatgtgataa | tttcaggaaa | caaaaatttg | 480 |
| tgctatgcaa | atacaataaa | ctggaaaaaa | ctgtttggga | cctccggtca | gaaaaccaaa | 540 |
| attataagca | atagaggtga | aaacagctgc | aaggccacag | gccaggtctg | ccatgccttg | 600 |
| tgctcccccg | agggctgctg | gggcccggag | cccaaggact | gcgtctcttg | ccggaatgtc | 660 |
| agccgaggca | gggaatgctg | ttctagaggt | ggtggaagtg | gtggaggatc | tggaggaggt | 720 |
| agcgttcctc | tgagcctgta | cagcggaagc | accagtggca | gcggtaagag | cagcgaggga | 780 |
| agcggaagcg | gggcccaagg | agagctcgtc | atgacccagt | ctccagcaat | catgtctgca | 840 |
| tctccagggg | agaaggtcac | tatgacctgc | agtgccagct | caagtgtaac | ttacatgtat | 900 |
| tggtaccagc | agaagccagg | atcctccccc | agactcctga | tttatgacac | atccaacctg | 960 |
| gcttctggag | tccctgttcg | tttcagtggc | agtgggtctg | ggacctctta | ctctctcaca | 1020 |
| atcagccgaa | tggaggctga | agatgctgcc | acttattact | gccagcagtg | gagtagtcac | 1080 |
| atattcacgt | tcggctcggg | gacaaagttg | gaaataaaag | gtggtggtgg | ttctggcggc | 1140 |
| ggcggctccg | gtggtggtgg | ttctcaggtc | cagttggtcg | agtctggagc | tgaactggtg | 1200 |
| aagcctgggg | cttcagtgaa | gttgtcctgc | aaggcttccg | gctacacctt | caccagccac | 1260 |
| tggatgcact | gggtgaagca | gagggctgga | caaggccttg | agtggatcgg | agagtttaat | 1320 |
| cccagcaacg | gccgtactaa | ctacaatgag | aaattcaaga | gcaaggccac | actgactgta | 1380 |
| gacaaatcct | ccagcacagc | ctacatgcaa | ctcagcagcc | tgacatctga | ggactctgcg | 1440 |
| gtctattact | gtgccagtcg | ggactatgat | tacgacggac | ggtactttga | ctactggggc | 1500 |
| caaggcacca | ctctcacagt | ctccgactac | aaagacgatg | acgataaaac | cggtcatcat | 1560 |
| caccatcacc | attga | | | | | 1575 |

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Val Pro Leu Ser Leu Tyr Ser
1               5

<210> SEQ ID NO 4

```
<211> LENGTH: 38
<212> TYPE: PRT
<213> ORGANISM: Artificial Sequence
<220> FEATURE:
<223> OTHER INFORMATION: Synthetic peptide

<400> SEQUENCE: 4

Gly Gly Gly Ser Gly Gly Gly Ser Gly Gly Gly Ser Val Pro Leu Ser
1               5                   10                  15
Leu Tyr Ser Gly Ser Thr Ser Gly Ser Gly Lys Ser Ser Glu Gly Ser
            20                  25                  30
Gly Ser Gly Ala Gln Gly
        35

<210> SEQ ID NO 5
<211> LENGTH: 521
<212> TYPE: PRT
<213> ORGANISM: Artificial Sequence
<220> FEATURE:
<223> OTHER INFORMATION: Synthetic construct

<400> SEQUENCE: 5

Met Arg Pro Ser Gly Thr Ala Gly Ala Ala Leu Leu Ala Leu Leu Ala
1               5                   10                  15
Ala Leu Cys Pro Ala Ser Arg Ala Arg Lys Val Cys Asn Gly Ile Gly
            20                  25                  30
Ile Gly Glu Phe Lys Asp Ser Leu Ser Ile Asn Ala Thr Asn Ile Lys
        35                  40                  45
His Phe Lys Asn Cys Thr Ser Ile Ser Gly Asp Leu His Ile Leu Pro
    50                  55                  60
Val Ala Phe Arg Gly Asp Ser Phe Thr His Thr Pro Pro Leu Asp Pro
65                  70                  75                  80
Gln Glu Leu Asp Ile Leu Lys Thr Val Lys Glu Ile Thr Gly Phe Leu
                85                  90                  95
Leu Ile Ala Ala Trp Pro Glu Asn Arg Thr Asp Leu His Ala Phe Glu
            100                 105                 110
Asn Leu Glu Ile Ile Arg Gly Arg Thr Lys Met Glu Gly Gln Phe Ser
        115                 120                 125
Leu Ala Val Val Ser Leu Asn Ile Thr Ser Leu Gly Leu Arg Ser Leu
    130                 135                 140
Lys Glu Ile Ser Asp Gly Asp Val Ile Ile Ser Gly Asn Lys Asn Leu
145                 150                 155                 160
Cys Tyr Ala Asn Thr Ile Asn Trp Lys Lys Leu Phe Gly Thr Ser Gly
                165                 170                 175
Gln Lys Thr Lys Ile Ile Ser Asn Arg Gly Glu Asn Ser Cys Lys Ala
            180                 185                 190
Thr Gly Gln Val Cys His Ala Leu Cys Ser Pro Glu Gly Cys Trp Gly
        195                 200                 205
Pro Glu Pro Lys Asp Cys Val Ser Cys Arg Asn Val Ser Arg Gly Arg
    210                 215                 220
Glu Cys Cys Ser Arg Gly Gly Ser Gly Gly Ser Gly Gly Gly
225                 230                 235                 240
Ser Val Pro Leu Ser Leu Tyr Ser Gly Ser Thr Ser Gly Ser Gly Lys
                245                 250                 255
Ser Ser Glu Gly Ser Gly Ser Gly Ala Gln Gly Asp Ile Leu Leu Thr
            260                 265                 270
Gln Ser Pro Val Ile Leu Ser Val Ser Pro Gly Glu Arg Val Ser Phe
```

```
                275                 280                 285
Ser Cys Arg Ala Ser Gln Ser Ile Gly Thr Asn Ile His Trp Tyr Gln
        290                 295                 300
Gln Arg Thr Asn Gly Ser Pro Arg Leu Leu Ile Lys Tyr Ala Ser Glu
305                 310                 315                 320
Ser Ile Ser Gly Ile Pro Ser Arg Phe Ser Gly Ser Gly Ser Gly Thr
                325                 330                 335
Asp Phe Thr Leu Ser Ile Asn Ser Val Glu Ser Glu Asp Ile Ala Asp
                340                 345                 350
Tyr Tyr Cys Gln Gln Asn Asn Asn Trp Pro Thr Thr Phe Gly Ala Gly
                355                 360                 365
Thr Lys Leu Glu Leu Lys Arg Ser Gly Ser Thr Ser Gly Ser Gly Lys
                370                 375                 380
Pro Gly Ser Gly Glu Gly Ser Thr Lys Gly Gln Val Gln Leu Lys Gln
385                 390                 395                 400
Ser Gly Pro Gly Leu Val Gln Pro Ser Gln Ser Leu Ser Ile Thr Cys
                405                 410                 415
Thr Val Ser Gly Phe Ser Leu Thr Asn Tyr Gly Val His Trp Val Arg
                420                 425                 430
Gln Ser Pro Gly Lys Gly Leu Glu Trp Leu Gly Val Ile Trp Ser Gly
                435                 440                 445
Gly Asn Thr Asp Tyr Asn Thr Pro Phe Thr Ser Arg Leu Ser Ile Asn
                450                 455                 460
Lys Asp Asn Ser Lys Ser Gln Val Phe Phe Lys Met Asn Ser Leu Gln
465                 470                 475                 480
Ser Asn Asp Thr Ala Ile Tyr Tyr Cys Ala Arg Ala Leu Thr Tyr Tyr
                485                 490                 495
Asp Tyr Glu Phe Ala Tyr Trp Gly Gln Gly Thr Leu Val Thr Val Ser
                500                 505                 510
Glu Thr Gly His His His His His His
        515                 520

<210> SEQ ID NO 6
<211> LENGTH: 524
<212> TYPE: PRT
<213> ORGANISM: Artificial Sequence
<220> FEATURE:
<223> OTHER INFORMATION: Synthetic construct

<400> SEQUENCE: 6

Met Arg Pro Ser Gly Thr Ala Gly Ala Ala Leu Leu Ala Leu Leu Ala
1               5                   10                  15
Ala Leu Cys Pro Ala Ser Arg Ala Arg Lys Val Cys Asn Gly Ile Gly
                20                  25                  30
Ile Gly Glu Phe Lys Asp Ser Leu Ser Ile Asn Ala Thr Asn Ile Lys
                35                  40                  45
His Phe Lys Asn Cys Thr Ser Ile Ser Gly Asp Leu His Ile Leu Pro
        50                  55                  60
Val Ala Phe Arg Gly Asp Ser Phe Thr His Thr Pro Pro Leu Asp Pro
65                  70                  75                  80
Gln Glu Leu Asp Ile Leu Lys Thr Val Lys Glu Ile Thr Gly Phe Leu
                85                  90                  95
Leu Ile Ala Ala Trp Pro Glu Asn Arg Thr Asp Leu His Ala Phe Glu
                100                 105                 110
Asn Leu Glu Ile Ile Arg Gly Arg Thr Lys Met Glu Gly Gln Phe Ser
```

```
            115                 120                 125
Leu Ala Val Ser Leu Asn Ile Thr Ser Leu Gly Leu Arg Ser Leu
    130                 135                 140
Lys Glu Ile Ser Asp Gly Asp Val Ile Ile Ser Gly Asn Lys Asn Leu
145                 150                 155                 160
Cys Tyr Ala Asn Thr Ile Asn Trp Lys Lys Leu Phe Gly Thr Ser Gly
                    165                 170                 175
Gln Lys Thr Lys Ile Ile Ser Asn Arg Gly Glu Asn Ser Cys Lys Ala
                180                 185                 190
Thr Gly Gln Val Cys His Ala Leu Cys Ser Pro Glu Gly Cys Trp Gly
            195                 200                 205
Pro Glu Pro Lys Asp Cys Val Ser Cys Arg Asn Val Ser Arg Gly Arg
210                 215                 220
Glu Cys Cys Ser Arg Gly Gly Ser Gly Gly Ser Gly Gly Gly
225                 230                 235                 240
Ser Val Pro Leu Ser Leu Tyr Ser Gly Ser Thr Ser Gly Ser Gly Lys
                245                 250                 255
Ser Ser Glu Gly Ser Gly Ser Gly Ala Gln Gly Glu Leu Val Met Thr
            260                 265                 270
Gln Ser Pro Ala Ile Met Ser Ala Ser Pro Gly Glu Lys Val Thr Met
            275                 280                 285
Thr Cys Ser Ala Ser Ser Ser Val Thr Tyr Met Tyr Trp Tyr Gln Gln
    290                 295                 300
Lys Pro Gly Ser Ser Pro Arg Leu Leu Ile Tyr Asp Thr Ser Asn Leu
305                 310                 315                 320
Ala Ser Gly Val Pro Val Arg Phe Ser Gly Ser Gly Ser Gly Thr Ser
                325                 330                 335
Tyr Ser Leu Thr Ile Ser Arg Met Glu Ala Glu Asp Ala Ala Thr Tyr
                340                 345                 350
Tyr Cys Gln Gln Trp Ser Ser His Ile Phe Thr Phe Gly Ser Gly Thr
            355                 360                 365
Lys Leu Glu Ile Lys Gly Gly Gly Ser Gly Gly Gly Ser Gly
    370                 375                 380
Gly Gly Ser Gln Val Gln Leu Val Glu Ser Gly Ala Glu Leu Val
385                 390                 395                 400
Lys Pro Gly Ala Ser Val Lys Leu Ser Cys Lys Ala Ser Gly Tyr Thr
                405                 410                 415
Phe Thr Ser His Trp Met His Trp Val Lys Gln Arg Ala Gly Gln Gly
                420                 425                 430
Leu Glu Trp Ile Gly Glu Phe Asn Pro Ser Asn Gly Arg Thr Asn Tyr
            435                 440                 445
Asn Glu Lys Phe Lys Ser Lys Ala Thr Leu Thr Val Asp Lys Ser Ser
            450                 455                 460
Ser Thr Ala Tyr Met Gln Leu Ser Ser Leu Thr Ser Glu Asp Ser Ala
465                 470                 475                 480
Val Tyr Tyr Cys Ala Ser Arg Asp Tyr Asp Tyr Asp Gly Arg Tyr Phe
                485                 490                 495
Asp Tyr Trp Gly Gln Gly Thr Thr Leu Thr Val Ser Tyr Lys Asp
            500                 505                 510
Asp Asp Asp Lys Thr Gly His His His His His
        515                 520

<210> SEQ ID NO 7
```

```
<211> LENGTH: 36
<212> TYPE: PRT
<213> ORGANISM: Artificial Sequence
<220> FEATURE:
<223> OTHER INFORMATION: Synthetic construct

<400> SEQUENCE: 7

Gly Ser Arg Ser Gly Gly Thr Ser Gly Gly Gly Ser Val Pro Leu Ser
1               5                   10                  15

Leu Tyr Ser Gly Ser Thr Ser Gly Ser Gly Lys Ser Ser Glu Gly Ser
            20                  25                  30

Gly Gln Ala Ser
        35

<210> SEQ ID NO 8
<211> LENGTH: 36
<212> TYPE: PRT
<213> ORGANISM: Artificial Sequence
<220> FEATURE:
<223> OTHER INFORMATION: Synthetic construct

<400> SEQUENCE: 8

Gly Ser Arg Ser Gly Gly Thr Ser Gly Gly Gly Ser Val Pro Gly Ser
1               5                   10                  15

Gly Ser Ser Gly Ser Thr Ser Gly Ser Gly Lys Ser Ser Glu Gly Ser
            20                  25                  30

Gly Gln Ala Ser
        35

<210> SEQ ID NO 9
<211> LENGTH: 19
<212> TYPE: PRT
<213> ORGANISM: Artificial Sequence
<220> FEATURE:
<223> OTHER INFORMATION: Synthetic construct

<400> SEQUENCE: 9

Val Leu Gly Gly Gly Gly Ser Gly Gly Gly Gly Ser Gly Gly Gly Gly
1               5                   10                  15

Ser Val His

<210> SEQ ID NO 10
<211> LENGTH: 43
<212> TYPE: PRT
<213> ORGANISM: Artificial Sequence
<220> FEATURE:
<223> OTHER INFORMATION: MMP9 cleavable linker

<400> SEQUENCE: 10

Gly Gly Gly Ser Gly Gly Gly Ser Gly Gly Ser Val Pro Leu Ser
1               5                   10                  15

Leu Tyr Ser Gly Ser Thr Ser Gly Ser Gly Lys Ser Ser Glu Gly Ser
            20                  25                  30

Gly Ser Gly Ala Gln Val Gln Leu Lys Gln Ser
        35                  40

<210> SEQ ID NO 11
<211> LENGTH: 43
<212> TYPE: PRT
<213> ORGANISM: Artificial Sequence
<220> FEATURE:
<223> OTHER INFORMATION: MMP9 non-cleavable linker

<400> SEQUENCE: 11
```

-continued

```
Gly Gly Gly Ser Gly Gly Gly Ser Gly Gly Gly Ser Val Pro Gly Ser
1               5                   10                  15

Gly Ser Ser Gly Ser Thr Ser Gly Ser Gly Lys Ser Ser Glu Gly Ser
            20                  25                  30

Gly Ser Gly Ala Gln Val Gln Leu Lys Gln Ser
        35                  40
```

DEVELOPMENT OF MASKED THERAPEUTIC ANTIBODIES TO LIMIT OFF-TARGET EFFECTS

PRIORITY CLAIM

This application is a continuation of U.S. patent application Ser. No. 14/949,648, filed on Nov. 23, 2015, issued as U.S. Pat. No. 10,357,571, Jul. 23, 2019, which is a continuation of U.S. patent application Ser. No. 13/424,272, filed Mar. 19, 2012, issued as U.S. Pat. No. 9,193,791, Nov. 24, 2015, which claims priority to U.S. Provisional Patent Application No. 61/454,500, filed Mar. 19, 2011; and is a continuation-in-part of U.S. application Ser. No. 12/849,786, filed Aug. 3, 2010 which is abandoned, all of which are hereby incorporated by reference in their entirety and for all purposes.

STATEMENT OF GOVERNMENT SUPPORT

The government has certain rights in the present invention. The present invention was made with government support under National Institutes of Health Grant Nos. R21CA135216 and S10 RR022316; and Grant No. W911QY-10-C-0176, awarded by the Department of Defense (DOD). The Government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048440-624C02US_SEQUENCE_LISTING_ST25.txt, created on Sep. 16, 2019, 16,796 bytes, machine format IBM-PC, MS-Windows operating system, is hereby incorporated herein by reference in its entirety and for all purposes.

BACKGROUND

Current monoclonal therapies for both leukemia and solid tumors suffer from a lack of specificity. Most often the targeted epitopes are not tumor specific, but are also present in other non-diseased tissues. In the case of Cetuximab and Matuzumab, expression of EGFR in hair follicles, the intestines and kidney leads to non-tumor toxicity. Patients experience an acneaform rash, gastrointestinal toxicity and hypomagnesemia that may limit the duration of therapy. For Trastuzumab, cardiotoxicity is observed because of the role that ErbB2 plays in cardiomyocyte health. The antibody exacerbates the cardiotoxicity of anthracyclines necessitating years of surveillance for development of dilated cardiomyopathy. For these antibodies and others it would be beneficial to improve tumor selectivity.

In addition to off-target effects, antibody therapies against solid tumors face other challenges. First, tumor vasculature is leaky, resulting in high interstitial pressures that any molecule entering the tumor has to overcome. Second, high affinity antibodies are needed to stay in the tumor long enough to exert their effects, but high affinity antibodies may encounter a "binding site barrier" where they were trapped by the peripheral antigen and never diffuse into the center of a solid tumor. This may result in underexposure of the tumor center. It would therefore be desired to develop antibodies and methods for their delivery to tumor cells that minimize effects to non-diseased tissues.

SUMMARY

Therapeutic antibodies cause side effects by binding receptors in non-target tissues. In one embodiment, a "prodrug" antibody design is described that ameliorates such side effects by occluding (directly or sterically), or "masking" antibody complement determining regions until they reach diseased tissues containing disease-associated proteinases. In one embodiment, a masked mAb may comprise a nucleotide sequence which encodes a first segment comprising a signal sequence; a second segment comprising a masking epitope sequence, wherein the masking epitope sequence contains an epitope specific to the mAb; a third segment comprising a cleavable linker sequence; and a fourth segment comprising an antibody or functional fragment thereof. In some embodiments, the fourth segment is a single chain variable fragment (scFv). In other embodiments, the fourth segment may be an IgG.

In some embodiments, two mAbs may form a heterodimer to produce a cross-masked mAb complex, comprising a first masked mAb comprising (1) a first masked antibody or fragment thereof having an antigen recognition site attached to a first masking epitope via a flexible linker, and (2) a second masked mAb comprising a second antibody or fragment thereof having an antigen recognition site attached to a second masking epitope via a flexible linker. The first and second masked mAbs may form a heterodimer complex by occlusion of the first and second antigen recognition sites by the second and first masking epitopes, respectively. The flexible linker may be cleaved by a protease specific to a target tissue allowing the cross-masked mAb heterodimer complex to dissociate at the target tissue. In some aspects, masked mAbs against the epidermal growth factor receptor (EGFR) were fused with a linker that is susceptible to cleavage by a proteinase to their epitope.

In another embodiment, a masked mAb may include a mAb bound by a protein A-protein L mask (protein A-L) mask. In another embodiment, protein A and/or protein L may be used as crystallization additives for a Fab.

Surface plasmon resonance and flow cytometry were used to confirm that binding is dependent on proteinase release. These molecular designs are generally applicable to other therapeutic antibodies to increase their specificity for diseased tissue.

BRIEF DESCRIPTION OF THE DRAWINGS

FIGS. 1A-C illustrate the combinatorial effects of mAbs 425 and C225 on proliferation and anchorage-independent cell survival of MDA-MB-468 breast cancer cells. FIG. 1A shows dose-dependent effects of either antibody alone at 10 μg/ml and the antibody combination at 10 μg/ml on metabolic activity as determined by WST-1 assay; the experiment was performed three times and results shown as m±SEM. FIG. 1B shows isobolographic representation of synergistic antibody effects at 25% growth inhibition. FIG. 1C shows impaired survival of MDA-MB-468 cells in forced suspension culture in the presence of the 425/C225 combination. In these experiments, the EGFR selective kinase inhibitor, AG1478, was used as a positive control. The capacity of cells to reattach and resume proliferation after two days of forced suspension culture in the presence or absence of 10% FCS was determined. Reattached cells were visualized by crystal violet staining 24 h after reseeding on cell culture-treated plastic FIG. 2 illustrates the effects of mAbs 425 and C225 alone and in combination on signal transduction events upon EGF treatment of MDA-MB-468 cells. Phosphorylation of signaling intermediaries (p-AKTS473; p-42/44MAPK; p-EGFRY1068) was determined by immunoblot analysis using phosphospecific antibodies for up to one hour after addition of EGF (10 ng/ml) to cells. Comparable loading of wells was assessed using antibodies recognizing the EGFR and β-actin, respectively. Use of the antibody combination amplified inhibitory effects of C225 on AKT and MAPK phosphorylation. Representative results of experiments performed three times are shown.

FIGS. 3A-C illustrate simultaneous binding of mAbs C225 and 425 to the extracellular portion of the EGFR (sEGFR). FIG. 3A shows surface plasmon resonance analysis of sEGFR captured by 425 tethered on CM5 chips. The real time sensorgram for each different sEGFR concentration (lighter, wavy lines) is superimposed with the calculated fit using the model of 1:1 Langmuir binding with mass transport limitation (fitted smooth black lines). The residuals of the fit are provided under the sensorgram. For calculation of binding affinities please refer to Table 1. FIG. 3B shows surface plasmon resonance analysis of sEGFR captured by C225 bound to CM5 chips. FIG. 3C shows binding of 425 to sEGFR captured by C225. Approximately 30 RUs of sEGFR were captured on a C225 immobilized CM5 chip and used as ligand to study the binding kinetics of mAb 425. Increasing concentrations of 425 were injected at 20 μl/min for two minutes association time and two minutes dissociation time. All Biacore experiments shown were conducted at least three times with similar results.

FIGS. 4A-B illustrate sedimentation equilibrium analysis of complexes formed by C225 and 425 Fabs and the extracellular portion of EGFR (sEGFR). FIG. 4A shows that the complex was formed by saturating sEGFR with Fab fragments of C225 and 425 and isolated by size exclusion chromatography. FIG. 4B shows radial scans at 280 nm were collected at 8000, 12000 and 16000 RPM at 20° C. The data fit well to a single molecular species and afforded a calculated molecular weight of 167,100+/−1000 Da, consistent with a tripartite complex.

FIGS. 5A-D illustrate independent binding of mAbs C225 and 425 to the human EGFR expressed on cell surfaces. Binding of Alexa Fluor 488-labeled C225 and 425 was assessed by FACS in the presence of unlabeled C225 or 425 as indicated in the panels. This analysis was performed using NIH3T3 cells engineered to express wild-type human EGFR (HC2; FIGS. 5A and 5B) or the tumor-specific EGFRvIII (CO12; FIGS. 5C and 5D) as indicated. In both cases, either antibody competed with itself but not with the other antibody. A representative example of three experiments is shown.

FIG. 6 illustrates modeling of the 425 binding site on the EGFR. Surface representation of the extracellular portion of EGFR bound to C225 (ribbon representation) based on the structure 1YY9 (Li et al., 2005). Glycosylation of asparagine residues found in the structure of 1YY9 are shown as sticks. The EGF-EGFR interface based on the crystal structure 1IVO (Ogiso et al., 2002) and limited to 5 Å cutoff is shown in the figure as "EGF Interface". Note that S460 and G461 represent the only surface residues of interest on domain III that are either not occluded by C225 or likely to be affected by N-linked glycosylation. The figure was made in PyMol (DeLano, 2002).

FIG. 7 illustrates that MAb 425 binds the EGFR at an epitope distinct from C225 as determined by size exclusion chromatography. mAbs 425 and C225 bind to domain III individually (Line 4 and Line 8) and as a combination (Line 9). Note that the complex of 425 with the EGFRdomIIIS460P/G461N elutes slightly earlier than the individual components (Line 5), but significantly later than the non-mutated domain III (Line 4). The complex of C225 with the mutated EGFRdIII (Line 7) eluted at the same volume as the non-mutated domain III (Line 8) indicating that the point mutations do not interfere with the overall tertiary structure. Asterisks denote an impurity present in the C225 preparation. The concentration of each sample added to the column was 4 μM (based on absorbance at 280 nM).

FIGS. 8A-B are schematic views illustrating the masked antibody (or "prodrug") concept in accordance with one embodiment. FIG. 8A illustrates the proof-of-principle, and FIG. 8B is a schematic view of the overall design to generate IgGs that are masked and do not bind antigens in normal tissues.

FIGS. 9A-C illustrate the design, production and characterization of cross-masked 425/C225 scFvs in accordance with one embodiment. FIG. 9A is a schematic diagram illustrating the topology of masked scFv constructs indicating point mutations in EGFRdIII for either mask. FIG. 9B is a graph illustrating the individual masked scFvs are monomeric whereas admixture of C225 and 425 cross-masked scFv is consistent with a heterodimeric complex as illustrated by size exclusion chromatography in accordance with one embodiment. FIG. 9C illustrates specific cleavage of crossmasked heterodimeric scFvs and individual masked scFvs by MMP9 as determined by SDS-PAGE.

FIGS. 10A-B illustrate the binding analysis of cross-masked 425/C225 scFvs in accordance with one embodiment. FIG. 10A shows surface plasmon resonance analysis of cross-masked 425/C225 binding at 1 μM and 100 nM to immobilized sEGFRdIII before and after MMP-9 digestion (indicated by arrow). FIG. 10B shows FACS analysis of scFv binding reveals that after MMP-9 digestion the cross-masked 425/C225 binds to HaCaT cells as well as the native scFvs. IgG 425 binding confirms EGFR expression.

FIG. 11 is an elution profile from Superdex 200 10/300 size exclusion column of masked (native domain III mask) C225 before and after MMP-9 treatment in accordance with one embodiment. Earlier elution in the absence of MMP-9 indicates the presence of a homodimeric cross-masked species that resolves into two non-covalent scFv-mask complexes. Elution volumes from the same column of the singly masked scFvs (with point mutated domain III masks) and cross-masked C225/425 are shown for comparison.

FIGS. 12A-B are graphical representations of traces from surface plasmon resonance affinity determinations for the singly masked C225 and 425 in accordance with one embodiment. The affinities are nearly identical before and after MMP-9 digestion. This suggests that the point mutations reduce the apparent affinity of the homodimer resulting in no masking.

FIG. 14 shows the nucleotide (SEQ ID NO:1) and amino acid (SEQ ID NO:5) sequences of masked C225 (Signal sequence-sEGFRdIII(Q384A/Q408M/H409E)-Linker (MMP-9 site)-scFv C225 ($V_L$-linker-$V_H$)-$H_6$).

FIG. 15 shows the nucleotide (SEQ ID NO:2) and amino acid (SEQ ID NO:6) sequences of masked 425 (Signal sequence-sEGFRdIII(S460P/G461N)-Linker(MMP-9 site)-scFv 425 ($V_L$-linker-$V_H$)-FLAG tag-$H_6$).

Figure 1:
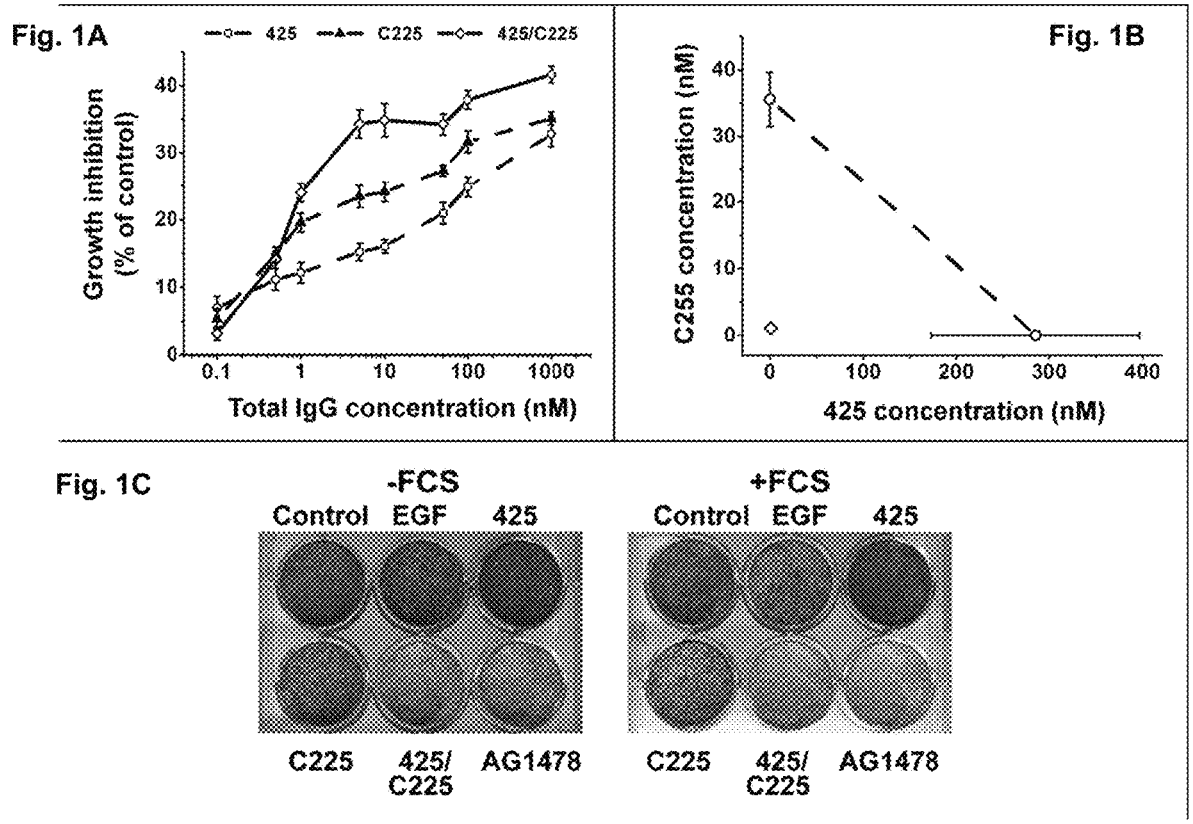

FIGS. 16A-B show a proposed molecular design to increase tumor selection and reduce off-target effects of therapeutic antibodies. FIG. 16A shows that by targeting cells that have increased antigen expression, which results in targeting of normal tissues with high antigen expression. FIG. 16B shows that increased specificity may be attained by designing antibodies that are activated selectively by proteases within tumor tissue (e.g., MMP-9).

FIG. 17 shows the masked antibody C225 and 425 constructs. Antibodies were assembled to include a "mask" comprised of domain III of the EGFR and a linker containing an MMP-9 consensus protease site. Point mutations corresponding to the epitope of the attached antibody were introduced into the domain III masks. The native EGFR signal sequence was used for secretion. Both antibodies were scFv constructs assembled with the light chain into the heavy chain. Only masked 425 contained a FLAG tag, while both antibodies contained a hexa-histadine tag that added in purification.

FIG. 18 shows a schematic diagram of a mask design for Cetuximab according to one embodiment. EGFR domain III is linked to the heavy chain of Cetuximab via an MMP9 cleavable (top line) or non-cleavable (bottom line) linker (left panel). The right panel shows the mask-heavy chain construct (dIII Linker HC) and the light chain (LC) of Cetuximab cloned into a dual expression GS selection vector.

FIG. 19 is a Western blot that illustrates transient and stable expression of masked Cetuximab with an anti-human Fc-HRP antibody of COS-7 culture supernatants three days after transient transfection (left panel); and a dot blot identification of stably-transfected masked-Cetuximab NS0 cell lines. Culture supernatant of single colony clones were spotted and blotted by anti-human Fc-HRP antibody.

FIG. 20 shows a non-reducing (left) and reducing (right) SDS-PAGE of masked Cetuximab with cleavable (WMC) and non-cleavable (XMC) linker. Expected molecular weight (MW) of masked Cetuximab (MC)=200 kD, mask-HC=75 kD, LC=24 kD.

FIG. 21 shows a reducing SDS-PAGE of MMP9 treated with masked Cetuximab with cleavable (WMC) and non-cleavable (XMC) linker.

FIGS. 22A-E illustrate sedimentation equilibrium analysis of (FIG. 22A) masked Cetuximab with a cleavable linker (WMC), (FIG. 22B) masked Cetuximab with a non-cleavable (XMC) linker, (FIG. 22C) WMC-Matuzumab cross-masked complex (WMC+M425), (FIG. 22D) XMC-Matuzumab cross-masked complex (XMC+M425), and (FIG. 22E) Matuzumab alone (M425). The data afforded a calculated molecular weight of 145,180 (M425), 219,890 (WMC), 226,940 (XMC), 239,320 (WMC+M425) and 353, 190 (XMC+M425).

FIG. 23 is a size-exclusion chromatography (SEC) elution analysis of the interaction of masked Cetuximab with a non-cleavable linker (XMC) and Matuzumab (M425). Peak fractions from XMC+M425, XMC and M425 were resolved on a non-reducing SDS-PAGE (left inset).

FIG. 24 is a size-exclusion chromatography (SEC) elution analysis of the interaction of masked Cetuximab with a cleavable linker (WMC) and Matuzumab (M425).

FIG. 25 shows the results of a FACS analysis of masked Cetuximab-matuzamb complex binding to MDA-MB-468 cells. Alexa 647-labeled XMC complexed with M425 were isolated from SEC, treated with MMP9, and mixed with trypsinized MDA-MB-468 cells, M425 were labeled with Alexa 488 anti-human IgG secondary antibodies.

FIG. 26 shows the results of a FACS analysis of masked Cetuximab-matuzamb complex binding to MDA-MB-468 cells. Alexa 647-labeled WMC complexed with M425 were isolated from SEC, treated with MMP9, and mixed with trypsinized MDA-MB-468 cells, M425 were labeled with Alexa 488 anti-human IgG secondary antibodies.

FIG. 27 shows a schematic diagram of a mask design for Trastuzumab according to one embodiment. HER2 domain IV is linked to the Fc region of Trastuzumab via an MMP9 cleavable (top line; SEQ ID NO:7) or non-cleavable (bottom line; SEQ ID NO:8) linker.

FIG. 28 is a non-reducing SDS-PAGE of the supernatant (sup.), flow through (FT) and the eluted protein (Elu.) from culture of baculoviruses that were transfected with the mask-Trastuzumab complex described in FIG. 27. The expected MW of the H4Fc dimer is 79 kDa, which is the band marked by (*).

FIG. 29 is a portion of a size exclusion chromatography (SEC) trace (bottom) was shown on the right, and a non-reducing SDS-PAGE (top) showing the H4Fc eluted from fractions 22-24 (F20-F24), as well as two aggregation species in F17 and F20 and a degradation product, likely the Fc portion, in F26.

FIG. 30 shows surface plasmon resonance analyses of H4Fc including a cleavable linker (HW; top trace) or of H4Fc that includes a non-cleavable linker (HX; bottom trace) captured by the Fab portion of Trastuzumab tethered on CM5 chips.

FIG. 31 is a non-reducing SDS-PAGE to resolve various protein combinations (Trastuzumab, HW, HX, MMP9) as indicated.

FIG. 32 shows results of a FACS analysis of Alexa 488 labeled Trastuzumab incubated with either H4Fc's at a 1:1 or 1:2 ratio for 20 min at room temperature, with or without MMP9 as indicated.

FIG. 33 illustrates the masking scheme for a generic mask to a monoclonal antibody. Upon interaction with a tumor-specific protease (b) (e.g., MMP9 or ADAM10), a masked monoclonal antibody (a), releases the protein A and L mask (c, d) and is free to bind target receptors on tumor cells.

FIGS. 34A-D show the interaction between protein A and Protein L with the heavy chain and light chain of the Trastuzumab Fab (FIGS. 34A, 34B) and the crystal structures of Proteins A and L bound to the Trastuzumab Fab (FIGS. 34C, 34D).

FIG. 35 is a table showing the X-ray diffraction data for Trastuzumab Fab.

FIGS. 36A-D illustrate sedimentation equilibrium analysis of a protein A-protein L mask, a Trastuzumab Fab, and a protein A-protein L mask/Trastuzumab Fab complex. FIG. 36A shows isolation of the protein A-protein L mask (mask), the Trastuzumab Fab (Fab), and a protein A-protein L mask:Trastuzumab Fab complex (Trastuzumab Fab+mask) by size exclusion chromatography. FIGS. 36B-D show radial scans at 280 nm. The data afforded a calculated molecular weight of 162,082+/−162.70 (mask), 45,909+/−166.41 (Fab) and 56,380+/−160.33 (mask+Fab), consistent with a 1:1 complex.

FIGS. 37A-C show surface plasmon resonance (SPR) analyses of the binding affinity of protein A (FIG. 37*a*), protein L (FIG. 37*b*) and protein A-protein L mask for Trastuzumab Fab (FIG. 37*c*), The concentration range for a-b is 3.2 nM to 5 μM and 10 pM to 1 μM.

FIGS. 38A-D show a comparison of on-rates of masked and unmasked Trastuzumab Fab binding to HER2 by illustrating an SPR Analysis of Trastuzumab Fab binding to HER2 (FIGS. 38*a*-38*b*) and Trastuzumab Fab with excess protein A-protein L mask binding to HER2 (FIGS. 38*c*-38*d*). Panels b and d compare the on rates of the two Fab to HER2.

DETAILED DESCRIPTION

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure.

Monoclonal antibodies are increasingly being used in the clinical management of diverse disease states, including cancer (Adams and Weiner, 2005). Monoclonal antibodies (mAbs) that inhibit activation of the epidermal growth factor receptor (EGFR) have shown therapeutic potential in select malignancies including breast cancer. As described in Example 1 below, the combined use of two such mAbs, C225 (Cetuximab) and 425 (EMD55900), reduces growth and survival of EGFR overexpressing MDA-MB-468 breast cancer cells more effectively than either antibody alone. Similarly, the C225/425 antibody combination more effectively inhibited AKT and MAPK phosphorylation in MDA-MB-468 cells. Surface plasmon resonance, size exclusion chromatography and analytical ultracentrifugation demonstrated that mAbs C225 and 425 simultaneously bind to distinct antigenic epitopes on domain III of the soluble wild-type EGFR. Furthermore, neither mAb competed with the other for binding to cells expressing either wild-type EGFR or a mutant EGFR (EGFRvIII) associated with neoplasia. Mutagenesis experiments revealed that residues S460/G461 in EGFR domain III are essential components of the 425 epitope and clearly distinguish it from the EGF/TGFα binding site and the C225 interaction interface. Collectively, these results support the conclusion that therapeutic EGFR blockade in cancer patients by combined use of mAbs C225 and 425 could provide advantages over the use of the two antibodies as single agents.

When used as 'targeted agents,' mAbs generally cause fewer severe side effects than traditional chemotherapy. However, adverse events have been reported and described for many antibody therapeutics due to inadvertent antigen recognition in normal tissues. In the case of epidermal growth factor receptor (EGFR) antagonistic mAbs, dose-limiting toxicities are thought to be due to engagement of the receptor by the therapeutic antibody in normal tissues (Lacouture et al., 2006; Rodeck, 2009).

The Erb tyrosine kinase family includes four members, of which the EGFR and Her2 are frequently deregulated in solid tumors and are of significant interest as therapeutic targets. MAbs to both antigens are used to treat various epithelial cancers. However, EGFR antagonistic mAbs, including Cetuximab (Masui et al., 1984), Matuzumab (Rodeck et al., 1987), and the fully human Panitumumab (Segaert and Van Cutsem, 2005; Van Cutsem et al., 2008), can cause dose-limiting adverse events affecting primarily the skin and the gastrointestinal system (Vanhoefer et al., 2004).

To address undesirable side effects (or "off-target" effects) caused by mAbs, antibody "prodrugs" were developed and tested as described herein. The antibody prodrug design is based on non-covalent protein interactions with the unmodified antibody to occlude of the antigen recognition sites (e.g., the complement determination regions (CDRs)) of mAbs or modulate the dynamics of the CDR through fusion with recombinant antigen fragments (also known as "masking epitopes") via a flexible linker. Invasive tumors typically express proteolytic enzymes, such as matrix metalloproteinases (MMPs), to breakdown the extracellular matrix for invasion and metastasis. Although the MMP family has at least 28 members, MMP-9 is known to correlate with malignancies that respond to epidermal growth factor blockade (Zhou et al. 2006; Swinson et al. 2004; Cox et al. 2000). The presence of these enzymes can distinguish tumor tissue from normal tissue.

Occluded antibody prodrugs that are described herein are also known as 'masked' antibodies and their activated counterparts are also known as 'unmasked' antibodies. Occluded or masked mAbs are prevented from binding in normal tissues that express the epitope but do not express MMPs. However, the mask is designed to be susceptible to MMPs. Masked or occluded mAbs may be 'activated' by including tumor protease specific sequences in the linker so that digestion by MMPs causes the mask to fall off. This adds an additional dimension to the current principle of tumor selectivity. Cell surface receptor (epitope) density is accepted as a primary selection basis for antibody targeting. Since these receptors exist in normal tissues, the antibodies also exert their effects in healthy tissues (FIG. 16A). By adding an additional selection property (i.e., MMP-9 expression), increased tumor specificity may be obtained. (FIG. 16B) Masked and unmasked antibody design has been tested using two EGFR antagonistic antibodies, 425 (Matuzumab) and C225 (Cetuximab); and a HER2 antibody, Trastuzumab.

Any mAb may be developed as a masked antibody. In some embodiments, the masked antibody may be a masked anti-EGFR. The epidermal growth factor receptor (EGFR; ErbB-1;HER1) is one of four members of the ErbB receptor family and contributes to growth, survival, migration and differentiation of epithelial cells (Yarden and Sliwkowski, 2001). Deregulated signaling through the EGFR either alone or in cooperation with other members of the ErbB family, notably ErbB2 and ErbB3, is a hallmark of multiple neoplasms predominantly of epithelial origin. The molecular mechanisms leading to deregulated EGFR-dependent signaling include overexpression of the EGFR, establishment of autocrine loops by aberrant overexpression of EGFR ligands and, the expression of mutated, constitutively active EGFRs (Mendelsohn and Baselga, 2000; Kim et al., 2001; Nagane et al., 2001).

In recognition of the potential roles of aberrant EGFR activation in tumor progression, multiple antagonists of EGFR activation have been developed with therapeutic intent. These can be broadly divided into two classes: (i) small molecules that target the kinase domain of the EGFR and inhibit its phosphorylation activity and (ii) monoclonal antibodies (mAbs) binding to the extracellular domain of the EGFR (Baselga and Arteaga, 2005). Typically, EGFR antagonistic mAbs were selected to disrupt ligand binding to the extracellular domain of the wild-type EGFR. Two examples of EGFR mAbs are the murine mAb 225 and the murine mAb 425. A chimeric version of 225 (C225; Cetuximab; Erbitux) containing a human Fc fragment has been FDA-approved for treatment of several epithelial neoplasias including colorectal carcinoma. A humanized version of 425 (EMD72000; Matuzumab) is currently in Phase II clinical trials in various epithelial neoplasms.

In other embodiments, the masked antibody may be a masked anti-HER2. HER2/ErBB2/Neu is a tyrosine kinase protein receptor which is expressed in the heart, lung, intestine and kidney and its activation is involved in growth and proliferation. HER2 is up-regulated in an aggressive form of metastatic breast cancer making it a potential target for cancer therapy. Herceptin®/Trastuzumab is a therapeutic humanized monoclonal antibody used to treat HER2 positive breast cancer.

Trastuzumab has been shown to elicit adverse side effects which are thought to be caused by off target binding of the antibody to HER2 expressed in healthy tissues at normal levels. This problem is not limited to Trastuzumab or to mAbs in general, in fact most targeted therapies target a mechanism rather than or in addition to the disease site. These adverse side effects could be prevented by specifically targeting the tumor cells rather than other cells that express HER2 at lower levels.

Figure 33:
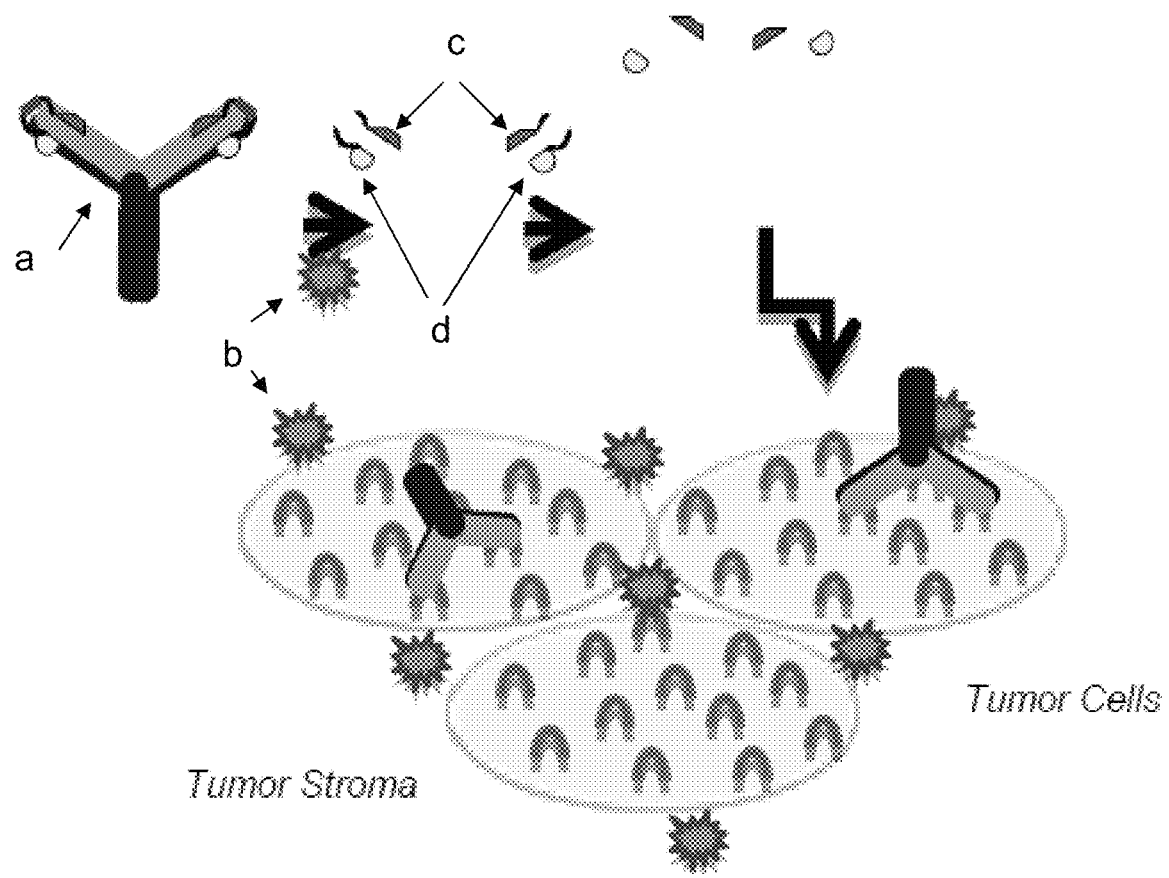
Figure 36A:
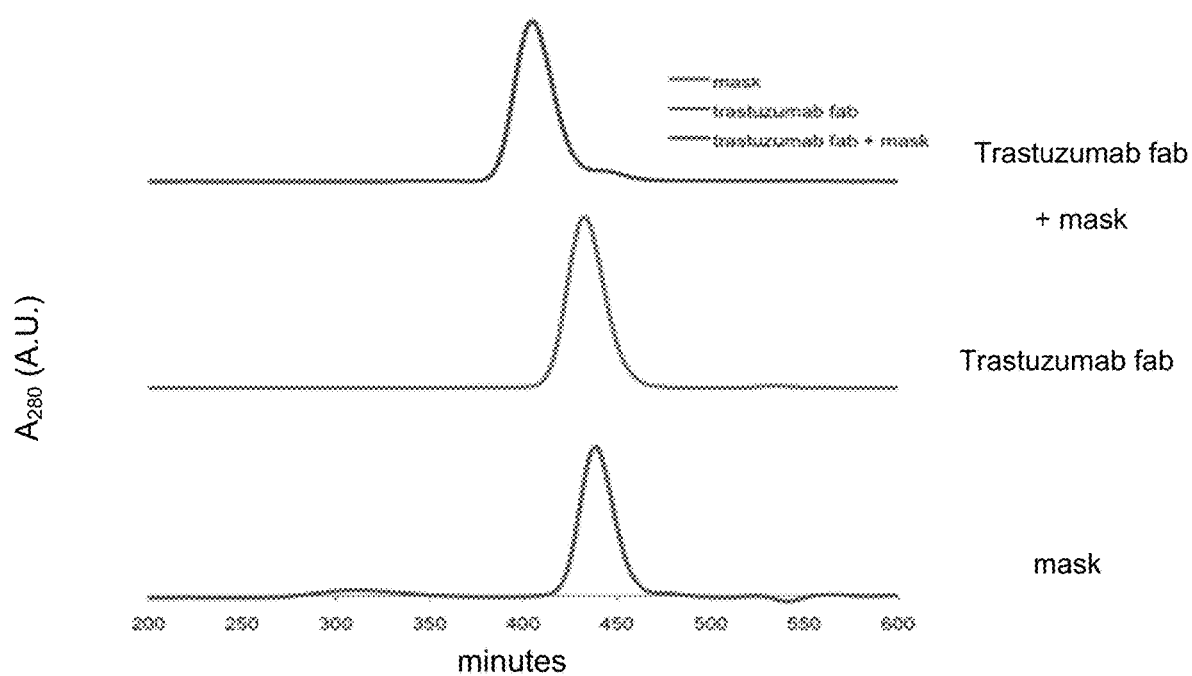

In some embodiments, a masked antibody may comprise a nucleotide sequence which encodes a first segment comprising a signal sequence; a second segment comprising a masking epitope sequence, wherein the masking epitope sequence contains an epitope specific to the mAb, for example the masking epitope sequence is specific to one or more antigen recognition sites (e.g., CDRs) of the mAb (i.e., is specific to the fourth segment, described below); a third segment comprising a cleavable linker sequence; and a fourth segment comprising an antibody or functional fragment thereof.

An antibody or functional antibody fragment thereof refers to an immunoglobulin (Ig) molecule that specifically binds to, or is immunologically reactive with a particular antigen, and includes both polyclonal and monoclonal antibodies. The term antibody includes genetically engineered or otherwise modified forms of immunoglobulins, such as intrabodies, chimeric antibodies, fully human antibodies, humanized antibodies, peptibodies and heteroconjugate antibodies (e.g., bispecific antibodies, diabodies, triabodies, and tetrabodies). The term functional antibody fragment includes antigen binding fragments of antibodies, including e.g., Fab', $F(ab')_2$, Fab, Fv, rIgG, and scFv fragments. The term scFv refers to a single chain Fv antibody in which the variable domains of the heavy chain and of the light chain of a traditional two chain antibody have been joined to form one chain.

In some embodiments, the fourth segment is a single chain variable fragment (scFv). Examples of individual masked antibodies are shown in FIGS. 14 (masked C225; SEQ ID NO:1 (nucleic acid); SEQ ID NO:5 (amino acid)) and 15 (masked 425; SEQ ID NO:2 (nucleic acid); SEQ ID NO:6 (amino acid)). In some embodiments, the fourth segment may be an IgG. The use of an IgG creates a bivalent format with an enhanced affinity to the target.

In some embodiments, two mAbs may form a heterodimer to produce a cross-masked mAb complex, comprising a first masked mAb comprising (1) a first antibody or fragment thereof having an antigen recognition site attached to a first masking epitope via a flexible linker, and (2) a second masked mAb comprising a second antibody or fragment thereof having an antigen recognition site attached to a second masking epitope via a flexible linker. The first and second masked mAbs may form a heterodimer complex by occlusion of the first and second antigen recognition sites by the first and second masking epitopes. The flexible linker may be cleaved by a protease specific to a target tissue allowing the cross-masked mAb heterodimer complex to dissociate at the target tissue.

In one embodiment of the disclosure, the EGFR antagonistic antibodies, 425 and C225 were selected for development of cross-masked antibodies. As shown in FIG. 8A, EGFR domain III, which has an epitope for both 425 and C225, was fused via a cleavable linker to an scFv of C225 and of 425. Point mutations in EGFR domain III favor a heterodimer. When the masked antibody is in the tumor, cleavage by a resident protease releases the EGFR domain III epitope, allowing the antibody to bind its target. FIG. 8B is a schematic view of the overall design to generate IgGs that are masked and do not bind antigen in normal tissues. Cross-masking permits the simultaneous delivery of two antibodies that synergize or target independent oncogenic signaling pathways.

In another embodiment of the disclosure, masked anti-EGFR antibody fragments are generated by cloning domain III of the soluble EGFR (sEGFRdIII)N-terminal to a cleavable linker followed by single chain variable fragment (scFv) versions of the anti-EGFR antibodies Matuzumab (mAb425 or 425) and Cetuximab (mAbC225 or C225) (FIGS. 9A and 17). In some embodiments, a metalloprotease 9 (MMP-9) substrate cleavage site, VPLSLYS (SEQ ID NO:3) (Turk et al., 2001) may be encoded within the cleavable linker. MMP-9 is frequently overexpressed in epithelial malignancies in which EGFR blockade may have therapeutic benefit (Swinson et al., 2004; Cox et al., 2000; Zhou et al., 2006).

In another embodiment, a masked anti-HER2 antibody or fragment thereof is generated by cloning domain IV of the HER2 receptor to a cleavable linker followed by an Fc fragment of the anti-HER2 antibody, Trastuzumab (FIG. 27). In some embodiments, a metalloprotease 9 (MMP-9) substrate cleavage site, VPLSLYS (SEQ ID NO:3) (Turk et al., 2001) may be encoded within the cleavable linker.

In one embodiment, a linker that was significantly longer than the minimal possible distance required may be used to address potential geometric problems of epitope association with the scFv and taking into consideration that affinity decays slowly as a function of linker length (Krishnamurthy et al, 2007). In such an embodiment, the serine-glycine rich linker has 12 and 19 residues flanking an MMP-9 sequence, producing an end-to-end length of approximately 133 angstroms (Å). Crystal structures have revealed the distance between the C-terminus of sEGFRdIII and the N-terminus of the antibody light chains is >35.1 Å for C225 (Li et al., 2005) and 34.7 Å for 425 (Schmiedel et al., 2008).

In further embodiments, the scFv may be replaced by an IgG, which creates a bivalent format. In this case, overall affinity to the tumor-derived antigen may be significantly enhanced due to energy additivity for the following reasons. First, FIG. 2B illustrates that the bivalent IgG 425 binds with greater affinity than the monovalent scFv. Second, cleaved masking epitopes (which are monomeric) compete poorly with tumor-derived EGFR for the unmasked antibody, and the bivalent interaction with cells may be favored over the monovalent mask interactions. Thus, the cleaved masking epitope is free to diffuse from the tumor site, favoring a higher affinity for the antibody. Moreover, the inclusion of an antibody Fc region enables downregulation of EGFR (Friedman et al., 2005) as well as antibody-dependent cell-mediated cytotoxicity (ADCC) and complement-dependent cytotoxicity (CDC) (Yan et al., 2008). Third, assuming no new constraints, the occlusion of the antibody binding sites may improve with the use of IgGs, as the masking will be tetravalent. The gain in affinity in the tetravalent format permits the inclusion of additional mutations in the mask to further enhance the dissociation rate of the masks upon protease cleavage.

In other embodiments, a masked antibody may comprise a protein A-protein L (protein A-L) mask that binds to a monoclonal antibody. Protein A (which binds the heavy chain of an antibody variable region) and Protein L (which binds the light chain of an antibody variable region), are two proteins known to bind antibodies, and in some embodiments, may be attached by a protease cleavable linker to take advantage of avidity providing tighter binding than either protein alone (see Example 4 below). Once the masked antibody reaches the tumor cell, the protease site will be cleaved by tumor over-expressing proteases, avidity will be lost, and the mask will dissociate allowing the antibody to bind at the tumor site (FIG. 33). The mask will not be significantly cleaved in healthy tissues and therefore will prevent off target binding. In one embodiment (as described in detail in the Examples below), the protein A-L mask binds Trastuzumab, but the protein A-L mask may be used to mask any suitable therapeutic antibody known in the art including, but not limited to, alemtuzumab, bevacizumab, Cetuximab, edrecolomab, gemtuzumab, ibritumomab tiuxetan, Matuzumab, panitumumab, rituximab, tositumomab, and Trastuzumab.

Crystallization of some antibodies has traditionally been challenging due to flexibility of the antibodies. One method of inducing crystallization may include addition of a ligand that changes the solubility of the protein. Therefore, in addition to forming a masked antibody, Protein A, Protein L or a combination of both may be used as 'additives' for Fabs that do not readily crystallize and/or to improve the diffraction limits of the same.

The following examples are provided to better illustrate the embodiments and are not to be interpreted as limiting the scope of any claimed embodiment. The extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention. Although the examples described below are focused on EGFR and HER2 mAbs, one skilled in the art would understand that the design strategy is broadly applicable to other mAbs and/or combinations used to treat cancer and chronic inflammation. Further, all references cited above and below are incorporated by reference as if fully set forth herein.

Example 1: EGFR Antagonistic mAbs C225 and 425 Cause Enhanced EGFR Inhibition and Distinct Epitope Recognition Materials and Methods
Cells and Reagents.
Human epithelial breast cancer cells MDA-MB-468 (ATCC HTB-132) were purchased from American Type Culture Collection (ATCC), Rockville, Md., USA. NIH3T3 cells transfected with either full-length human EGFR (CO12) or mutated EGFR variant III (EGFRvIII; HC2) were a generous gift from Dr. Albert Wong (Moscatello et al., 1996). MAb 425 was isolated from murine ascites by affinity purification using Protein A Sepharose columns followed by Ion Exchange columns (GE Health Sciences Q Sepharose 4, fast flow). Purified C225/Cetuximab was purchased from Bristol Myers Squibb, Princeton, N.J. The EGFR selective tyrosine kinase inhibitor, tyrphostin AG1478 (AG1478), was purchased from Calbiochem. For surface plasmon resonance experiments, the extracellular soluble domain of the human EGFR (sEGFR) was purchased from R&D Systems, Inc., WST-1 cell proliferation kit was purchased from Takara Bio Inc. HC2, CO12, and MDA-MB-468 cells were cultured in DMEM supplemented with 1 g/l glucose, 2 mM L-glutamine, 10% FBS, 1% penicillin/streptomycin under standard conditions.

Expression of Recombinant EGFR Fragments.
Soluble EGFR (sEGFR) constructs (including, but not limited to, any soluble EGFR construct including approximately residues 1-618 to residues 1-629), extracellular domain (residues 1-621) and domain III, (residues 310-512) were generated, produced and purified closely following published methods (Ferguson, 2004). Two point mutations, S460P/G461N, were introduced into sEGFR domain III by site directed mutagenesis using the QuikChange method (Stratagene).

Papain Digestion of 425 and C225.
Fab fragments of 425 and C225/Cetuximab were prepared by papain digestion and Protein A reverse purification (Pierce). Each protein was further purified using a HiLoad 16/60 Superdex 75 column.

Flow Cytometry.
Flow cytometric analyses were carried out using mAbs 425 and C225 conjugated to Alexa Fluor 488 through primary amines following the manufacturer's protocol (Molecular Probes). Between 4-6 Alexa 488 molecules were bound per antibody as estimated by measuring the optical density at 280 nm and 494 nm. For FACS analysis, cells were detached using a non-enzymatic cell dissociation solution (Cellgro), collected and resuspended in wash buffer (1×PBS containing 1% BSA). Approximately 500,000 cells were incubated at 4° C. in 50 µl of labeled and unlabelled antibodies as indicated. After 30 minutes of incubation, cells were washed three times with wash buffer and fixed using 1% freshly prepared paraformaldehyde. Samples were analyzed on a FACS Canto (BD Biosciences).

WST-1 Assay.
Effects of C225 and 425 on metabolism of MDA-MB-468 were measured by assaying cleavage of the tetrazolium salt WST-1 to fluorescent formazan by cellular mitochondrial dehydrogenases as quantified by measuring the absorbance of the dye solution at 450 nm. In 48-well plates, approximately 3000 cells/well suspended in 200 µl of DMEM containing 10% FCS were allowed to attach for 24 hours. After 24 hours, 100 µl of antibody solutions diluted in DMEM were added to each well to achieve the desired concentrations. After 72 hours, 30 µl of WST-1 was added for another three hours. For analysis, 60 µl of culture medium was added to 200 µl of 1×PBS buffer and the absorbance was measured at 450 nm using a Victor2 1420 Multilabel counter (Perkin Elmer). The absorbance at 550 nm was used for background correction. The percent inhibition was calculated as 100*(AbsControl−AbsmAb)/AbsControl.

Anchorage-Independent Cell Growth and Survival.
Cell survival in the anchorage-independent state was determined as previously described (Jost et al., 2001a) with minor modifications. Cell suspensions were prepared in DMEM containing 0.2% BSA in the presence and absence of 10% FCS, mAbs 425, C225 or their combination (10 µg/ml final antibody concentration), AG1478 (10 µM) and/or EGF (10 ng/ml). After 48 and 72 hours, 500 µl of cell suspension was transferred to another 6-well plate with the respective culture medium and allowed to attach and grow for 24 hours. Attached cells were fixed in 75% ethanol and stained with crystal violet.

Immunoblot Analyses.
Cells were incubated in complete growth medium in 100 mm petri dishes (1×10$^6$ cells per dish) for 24 hours. After overnight incubation in serum-free DMEM containing 0.2% BSA, antibodies (10 µg/ml final IgG concentration) or AG1478 (10 µM) were added. After one hour, EGF (10 ng/ml final concentration) was added to culture media and cells lysed using Laemmli buffer. Differences in the phosphorylation of MAPK, AKT and EGFR were determined by immunoblot analysis. Antibody binding was detected using an enhanced chemiluminescence system (Pierce).

Biacore Surface Plasmon Resonance Analysis.

Molecular interactions were determined using a Biacore® 3000 optical biosensor (Biacore Inc.). Immobilization of EGFR specific mAbs to CM5 sensor chips were performed following the standard amine coupling procedure. Unless specified otherwise anti-HIV-1 gp120 antibody 17b immobilized on CM5 chips was used as a reference flow cell (Thali et al., 1993). Ligand densities and flow rates were optimized to minimize mass transport and rebinding effects.

Analysis of direct binding of sEGFR in a concentration dependent manner to 425 or C225 was achieved by passage over mAb surfaces with a ligand density of 200 RUs and a flow rate of 50 μl/min for two minutes association and 6 minutes dissociation at 25° C. Regeneration of the surfaces between injections was achieved by injecting three, six sec pulses of 10 mM glycine, pH 2.0 at the flow rate of 100 μl/min.

To study simultaneous binding of 425 and C225, a capture SPR format was employed. Briefly, sEGFR (5 nM) was injected over a low density C225 surface (280 RUs) at 20 μl/min. The captured sEGFR was then used as ligand to perform saturation analysis by injecting increasing concentrations of 425 (0-512 nM) for three minutes at a flow rate of 50 μl/min until binding equilibrium (Req) was achieved. Data were analyzed using BIAevaluation® 4.0 software (Biacore Inc., NJ). The responses of a buffer injection and responses from a reference flow cell were subtracted to account for nonspecific binding and instrument noise. Experimental data were fitted to a simple 1:1 binding model with a parameter included for mass transport.

Sedimentation Equilibrium Analysis.

A complex of full-length sEGFR, Fab425 and FabC225 was incubated for 30 minutes, applied to a HiLoad 16/60 Superdex 200 prep grade column and loaded into a 6-well, analytical centrifugation cell at A280 nm=1.0. The samples were centrifuged using an An-50 Ti rotor at 20° C. in a Beckman ProteomeLab XL-I ultracentrifuge. Absorbance scans at 280 nm were performed after 12 and 14 hours at 8000, 12000 and 16000 RPM. Equilibrium was assessed by comparison of scans at 12 and 14 hours. Analysis was performed using FastFitter (Arkin and Lear, 2001) as implemented in Igor Pro (Wavemetrics, Lake Oswego, Oreg.). The solvent density ($\rho$) was set at 1.0042 g/ml and the specific volume (VBAR) was assumed to be 0.76 ml/g.

Size Exclusion Chromatography.

Complexes comprised of different combinations of sEGFR domain III, the mutated (S460P/G461N) sEGFR domain III, Fab 425 and Fab C225 were prepared at 4 μM and incubated for 20 minutes. Size exclusion chromatography was performed at 4° C. using a Superdex 200 HR10/30 column (GE Health Sciences) and monitored at 280 nm Cooperative Inhibition of Growth and Survival of MDA-MB-468 Breast Carcinoma Cells by mAbs 425 and C225.

Combinations of mAbs binding to different epitopes of the same antigen have proven to exert synergistic effects against tumor cells expressing their cognate antigens at the cell surface. For example, two antibodies to ErbB2 (i.e., Trastuzumab and Pertuzumab) inhibit survival of breast cancer cells more effectively than either antibody alone (Nahta et al., 2004).

The antibodies 425 and C225 both have the capacity to inhibit ligand binding to the EGFR independently, but act synergistically (i.e., a much lower dose of the antibody combination achieved the same biological response) to affect breast tumor cell growth and survival. The C225 binding epitope is in direct competition with EGF/TGFα for binding to domain III of the extracellular portion of the EGFR (Gill et al., 1984; Li et al., 2005). MAb 425 interferes with ligand access to the EGFR (Murthy et al., 1987), but the binding site for 425 is currently unknown. The effects of either antibody alone were compared with those of the combination of both antibodies on growth and survival of MDA-MB-468 breast carcinoma cells that express high levels of EGFR (Biscardi et al., 1998). To avoid effects due to differences in antibody concentration the total amount of IgG was kept constant for all experimental conditions. As shown in FIG. 1A, the combination of the two antibodies is superior to either antibody alone in inhibiting metabolic activity of actively growing, attached MDA-MB-468 cells. The synergistic effect of the antibody combination at 25% growth inhibition is demonstrated by isobologram which depicts equally effective dose pairs (isoboles; FIG. 1B). In this representation, the concentration of one drug required to produce a desired effect is plotted on the horizontal axis while the concentration of another drug producing the same effect is plotted on the vertical axis. A straight line joining these two points represents additive effects expected by the combination of two drugs. FIG. 1B shows that, at 25% growth inhibition, the experimental value for the antibody combination lies well below the theoretical additive line consistent with drug synergism. This demonstrates that the combination of the two antibodies is superior to either antibody alone in inhibiting metabolic activity of actively growing MDA-MB-468 cells.

The capacity of the antibody combination to induce cell death in the anchorage-independent state is illustrated in FIG. 1C. It has been previously demonstrated that EGFR inhibition with either 425 (10 μg/ml) or with small molecule tyrosine kinase inhibitors accelerates apoptosis of epithelial cells maintained in forced suspension culture which precludes extracellular matrix attachment (Jost et al., 2001a; Jost et al., 2001b). A simple method to assay cell survival in these conditions consists of reseeding cells on tissue culture-treated plastic after defined periods of suspension culture and the determination of cell reattachment after 12-24 hours. Treatment with either antibody at 10 μg/ml during suspension culture reduced the number of cells capable of matrix reattachment only marginally irrespective of the culture medium used in these experiments (FIG. 1C). In contrast, the combination of both antibodies where each antibody was used at 5 μg/ml markedly reduced levels of viable reattached cells similar to cultures treated with the small molecule EGFR inhibitor AG1478. This indicates that the antibody combination accelerates death of MBA-MB-468 cells in the anchorage-independent state.

Inhibitory Effects of the C225/425 Antibody Combination on Signal Transduction Events Triggered by EGFR Activation.

Figure 2:
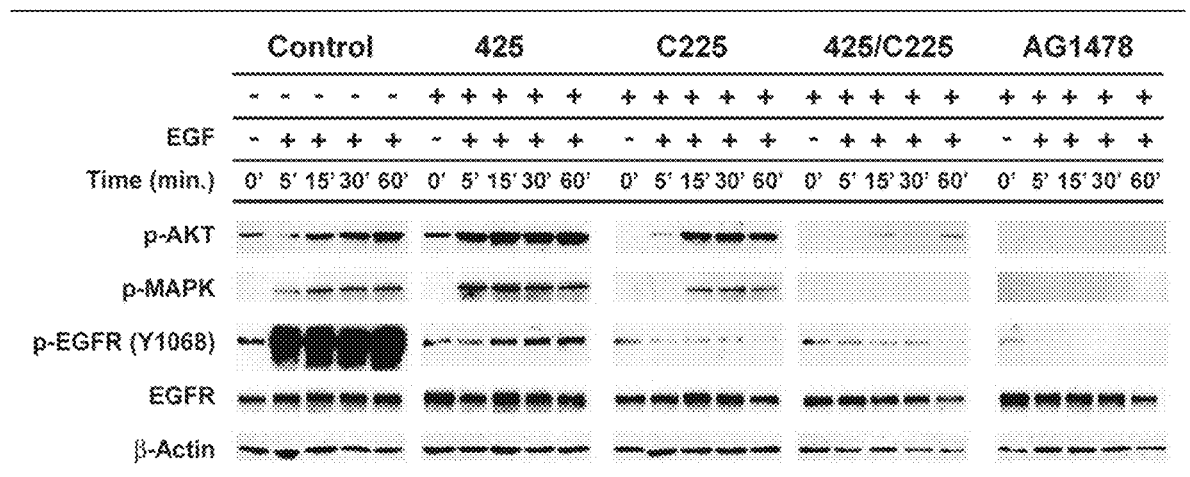

To account for combinatorial inhibitory effects of the C225/425 antibody combination on EGFR-dependent signal transduction events, the effects of the antibodies used either singly or in combination on short-term EGF-induced signal transduction events were determined in serum-starved MDA-MB-468 cells. This revealed more efficient inhibition of AKT and p42/44MAPK phosphorylation in serum-starved cells exposed to EGF and the antibody combination as compared to single antibody treatment (FIG. 2). Moreover, in MDA-MB-468 cells, 425 treatment alone did not inhibit AKT and MAPK phosphorylation, whereas it effectively reduced EGF-dependent phosphorylation of the EGFR on Y1068. As in the case of cell growth inhibition experiments, the effects on signal transduction events occurred although either antibody was used at half the concentration (5 µg/ml) when combined as compared to single antibody treatments (10 µg/ml). Therefore, the C225/425 antibody combination effects were similar to those achieved by using AG1478 at very high concentration (10 µM).

Simultaneous Binding of 425 and C225 to the Extracellular Domain of the EGFR.

Figure 3A:
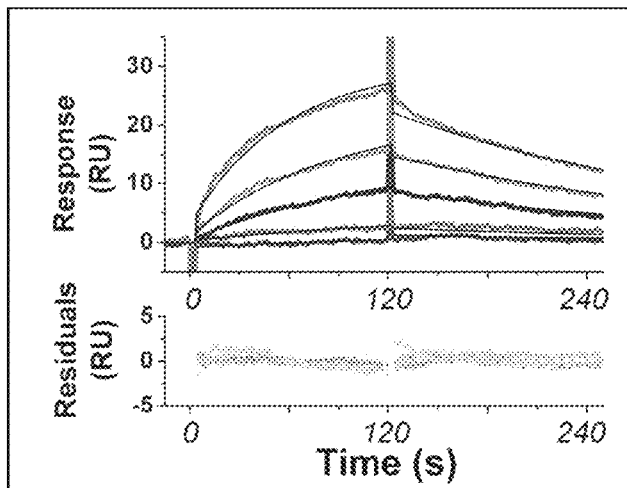
Figure 3B:
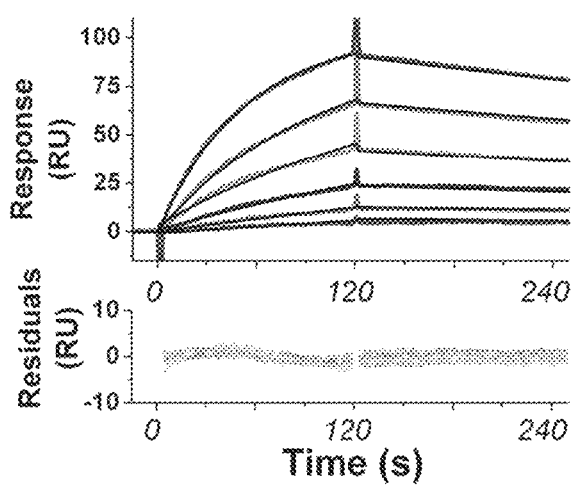

Cooperative growth inhibitory effects by the two antibodies can be explained by the binding of these antibodies to distinct EGFR populations thus providing more effective ligand binding competition. Alternatively, the two antibodies may simultaneously engage distinct epitopes of the EGFR domain III and inhibit EGFR-dependent signal transduction by independent mechanisms. To distinguish between these two possibilities, surface plasmon resonance experiments were performed whereby either antibody was immobilized on a CM5 chip and successive binding of soluble extracellular domain of the EGFR and the second antibody was monitored. First, binding of sEGFR to either 425 or C225 immobilized on the chip was characterized, as shown in FIGS. 3A and 3B. Lower RUs (~200 RU) of mAbs were conjugated to avoid mass transport limitations. Additionally, sEGFR was injected at a high flow rate of 50 µl/min in order to overcome potential receptor rebinding effects. The resultant sensorgrams were then analyzed and the equilibrium rate constants were calculated. Each different concentration of injected sEGFR is represented by a real time sensorgrams (lighter, wavy lines) while the calculated kinetic fit of each interaction is represented by superimposed smooth black line. The results showed that C225 binds to sEGFR with a higher affinity (2.7±0.4 nM) compared to 425 (32.3±6.75 nM) due to a comparatively higher dissociation rate of 425.

Figure 3C:
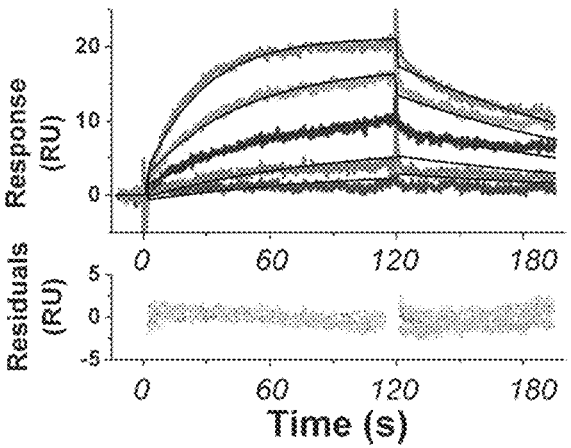

Next, it was determined whether sEGFR bound to C225 immobilized on the chip was capable of capturing 425. To this end, sEGFR (5 nM) was injected over a low density C225 chip (280 RU) followed by different concentrations of 425 (0-512 nM) until binding equilibrium was reached. The sensorgrams show binding of concentration-dependent binding of 425 to sEGFR captured by C225 (FIG. 3C), consistent with noncompetitive binding of the two antibodies to sEGFR.

Figure 4A:
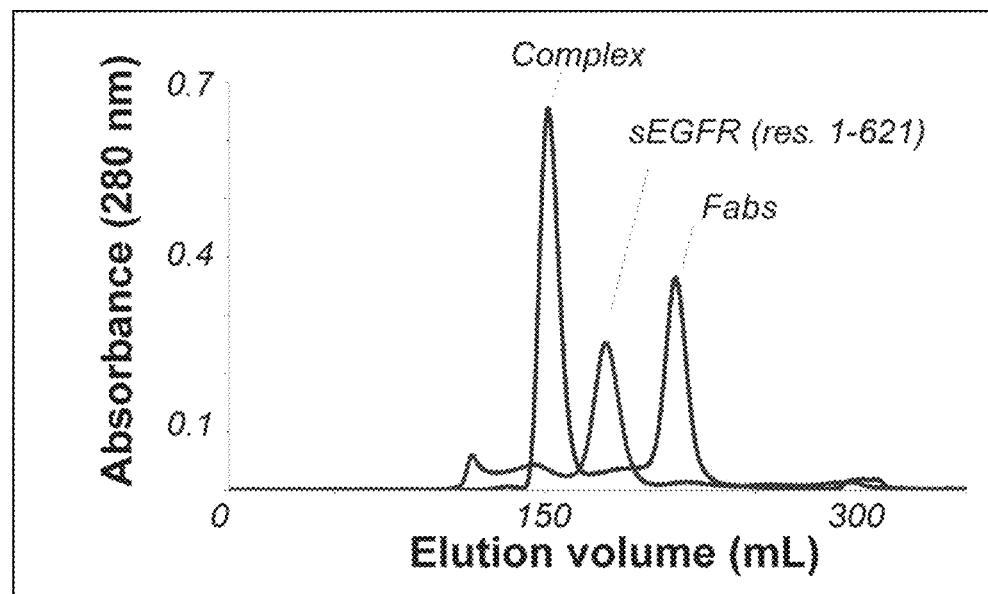
Figure 4B:
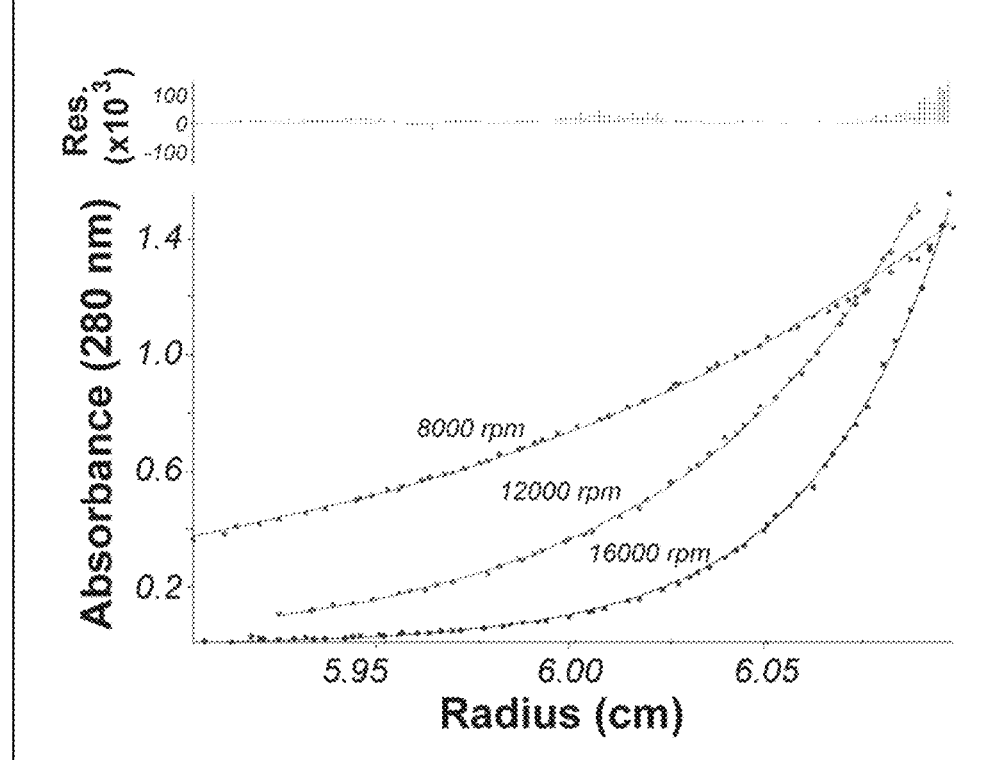
Figure 5A:
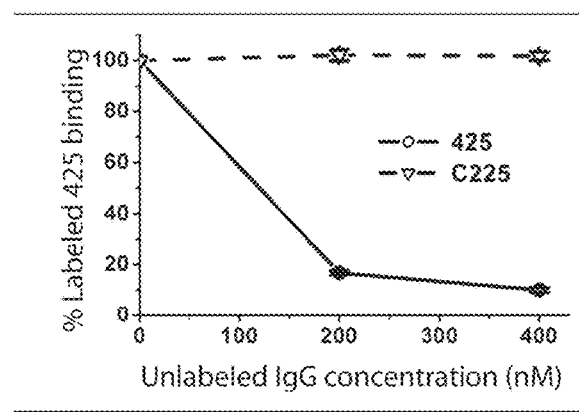
Figure 5B:
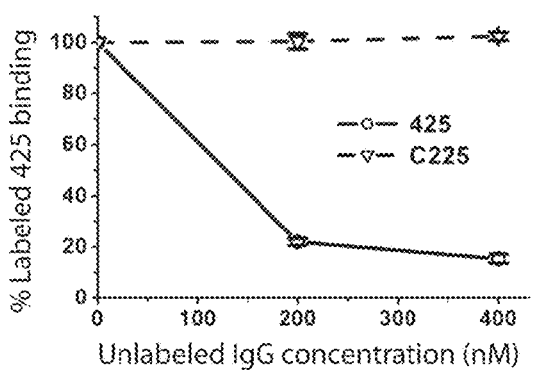
Figure 5C:
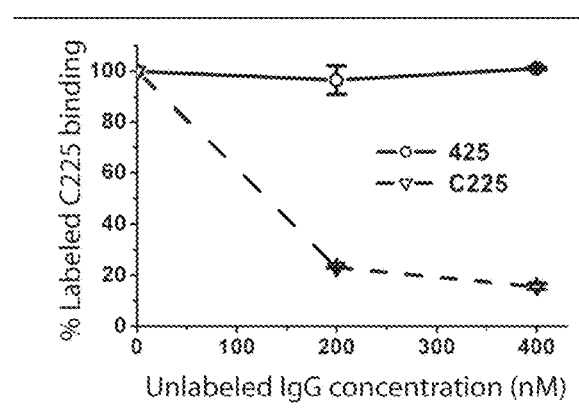
Figure 5D:
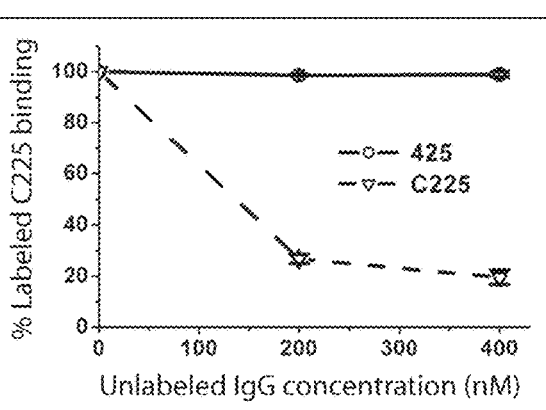

To obtain independent confirmation for simultaneous binding of both antibodies to EGFR, a sedimentation equilibrium analysis was performed by analytical ultracentrifugation using an admixture of C225, 425 and the extracellular portion of the EGFR consisting of domains I to IV (sEGFR). This indicated a single species with an apparent weight of 167 kD, consistent with the existence of a 1:1:1 tripartite molecular complex (FIGS. 4A-B). Note that total concentration was at 4.5 µM or >100-fold and >1000-fold the dissociation constant of 425 or C225 and EFGR, respectively. Together, these results strongly suggest that the binding epitopes of C225 and 425 are distinct albeit both are confined to domain III of the extracellular portion of the human EGFR (Lax et al., 1991).

Next it was determined whether both antibodies could also simultaneously engage the EGFR expressed on cell surfaces. NIH3T3 cells stably transfected with either full length wild-type human EGFR (CO12 cells) or a mutated EGFR characterized by intragenic deletion of most of domain II of the EGFR and prominently expressed in neoplasia (HC2 cells) were used for this purpose (Moscatello et al., 1996). Both antibodies bind exclusively to domain III of the EGFR (Lax et al., 1991), and therefore may bind to both wild-type and tumor-specific EGFRvIII. To avoid confounding effects of endogenous EGFR expression, transfected mouse 3T3 cells were used rather than human cells. Since neither antibody recognizes the murine EGFR (Murthy et al., 1987; Wen et al., 2001), no binding other than to the transfected human EGFR was measured. To assess direct binding competition between the two antibodies, the ability of 425 to replace C225 from the cell surface of CO12 and HC2 cells was determined by FACS analysis. The results showed that each antibody competes with itself for cell surface binding but not with the other antibody (FIGS. 5A-D). In addition, both antibodies recognized both human wild-type EGFR and EGFRvIII. These results indicate that both C225 and 425 antibodies independently and simultaneously bind to distinct epitopes on domain III of the extracellular portion of recombinant human EGFR and cell associated EGFR.

C225 directly competes with ligand binding to domain III of the EGFR (Li et al., 2005) and 425 is also known to bind to domain III even though its epitope has yet to be defined. Therefore, the 425 binding site may encompass residues that are different in the human and murine EGFR sequences, since 425 recognizes a conformationally defined epitope of the human but not the murine EGFR (Murthy et al., 1987). Residues that differ between the murine and human sequences and are present on the surface of the sEGFR domain III are likely candidates for the epitope defined by 425 binding. In addition, because C225 and 425 bind simultaneously to the surface of EGFR domain III, the 425 epitope likely lies outside of the surface masked by C225.

Figure 6:
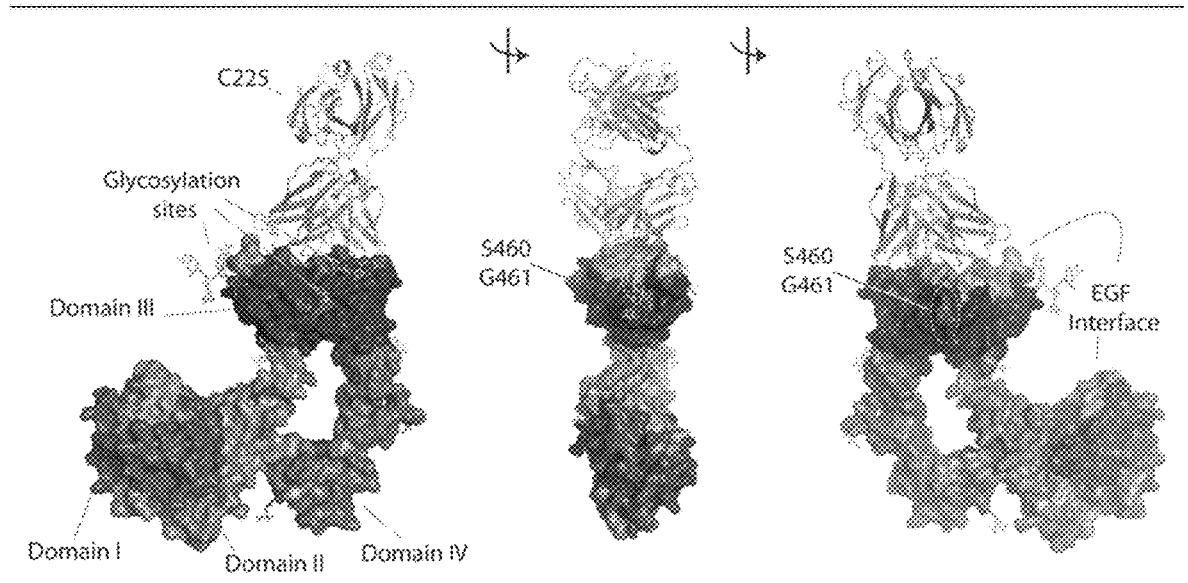
Figure 7:
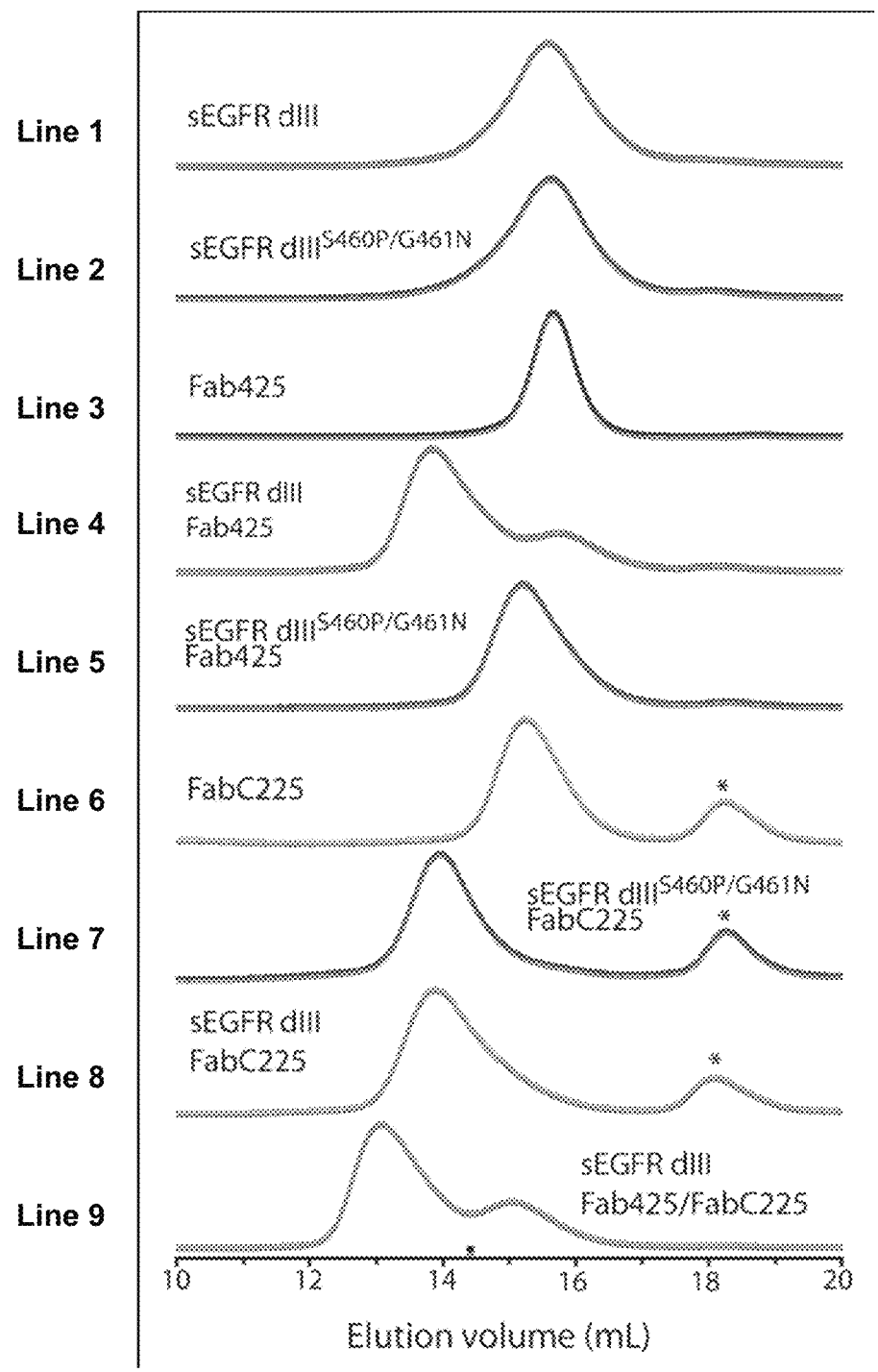
Figure 8A:
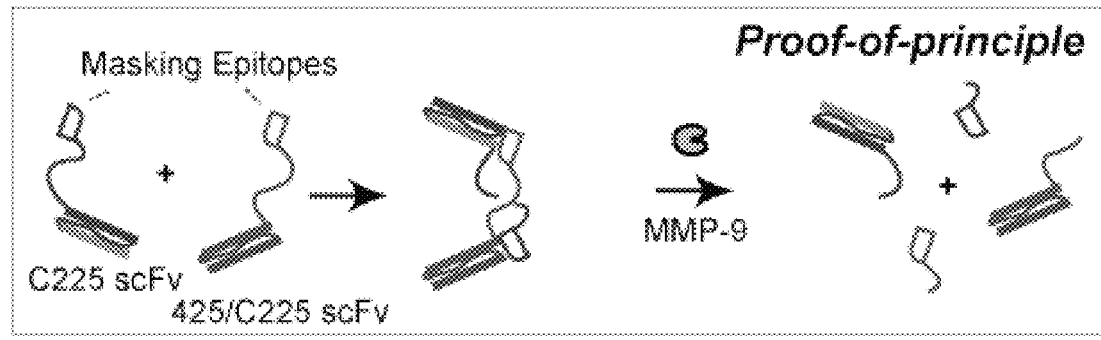
Figure 8B:
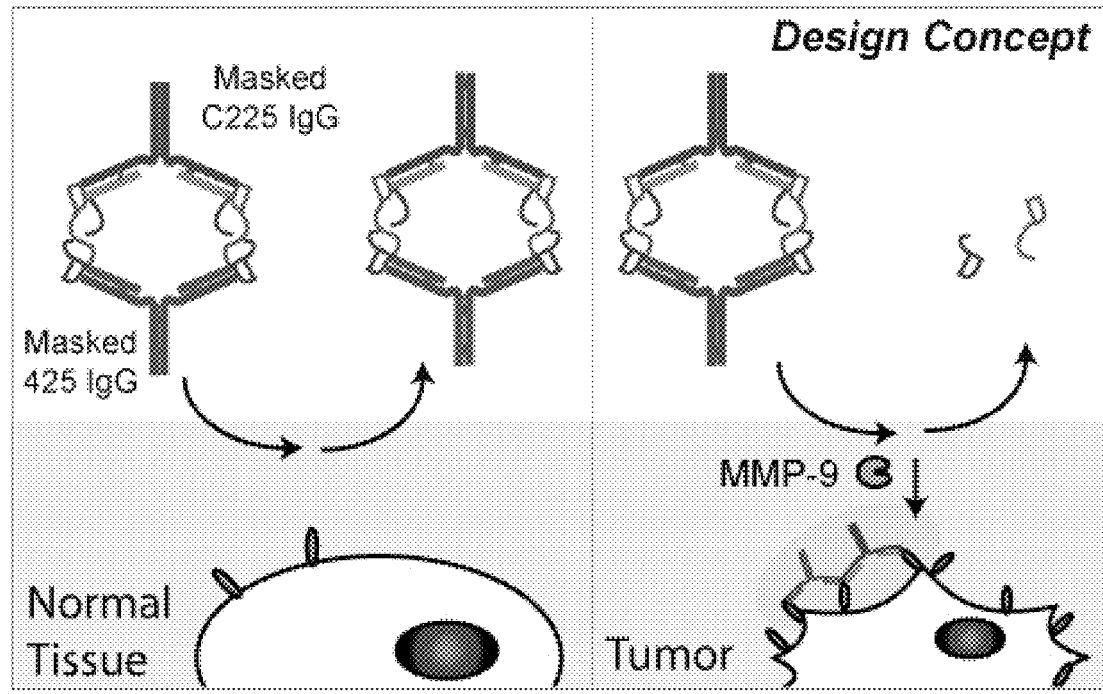

Mapping of the human EGFR using these constraints produced a handful of potential EGFR/425 interaction sites (FIG. 6). Many of these sites are located near glycosylation sites and were considered unlikely targets for 425 binding because it was previously shown that 425 recognizes a protein epitope on the deglycosylated EGFR (Murthy et al., 1987). After exclusion of residues occluded by either C225 or by putative carbohydrate side chains, two adjacent amino acids emerged as likely candidates for 425 docking (Ser460 and Gly461 highlighted in FIG. 6). To investigate the role of these residues in 425 binding, these two residues were changed in human EGFR domain III to the corresponding murine sequence, (i.e., Pro460 and Asn461), expressed and purified this domain, and used size exclusion chromatography to test whether 425 could bind sEGFR domain III encoding S460P and G461N mutations (FIG. 7). The individual Fabs and sEGFR domain III proteins eluted at 15.6 mL. Co-incubation of sEGFR domain IIIS460P/G461N with Fab425 resulted in a slightly earlier elution, 15.2 mL, indicating weak association. The concentration of the mixture added to the column is 4 µM, which is greater than the KD of the native EGFR/425 interaction by a factor of 125, indicating a weak association. Similarly, mutations that define the C225 epitope on EGFR-domain III reduce the affinity from 2.3 nM to 340 nM (Li et al., 2005) and a complex formed by such a mutant and C225 also show residual binding wherein the concentration is greater than the original KD (e.g., ~290 nM) by a factor of 125. However, human sEGFR domain III at the same concentration forms a saturated complex that eluted at 13.9 mL. To demonstrate that the point mutations did not affect the tertiary structure of the sEFGR domain III, the S460P and G461N mutant were also mixed with C225 Fab and subjected to analysis by size exclusion chromatography. The resulting elution point at 14.0 mL was similar to the wild-type sEGFR domain III complexed with C225. Finally, when wild-type sEGFR domain III and both Fabs were mixed and applied to the column, a distinct peak eluting at 13.1 mL emerged, consistent with a tripartite complex. These data indicate that Ser460 and Gly461 significantly contribute to the overall affinity of the EGFR-425 interaction.

Because 425 does not compete with C225 for binding and recognizes surface residues distinct from the ligand binding site, a different mechanism of action that is independent of C225 and the ligand may account for its biological effects. Specifically, interaction of 425 with the EGFR may interfere with high affinity ligand binding by blocking a conformational change to bring domains I and III of the extracellular domain of the EGFR in close proximity.

Example 2: EGFR-Specific scFvs Engineered to Enable Selective Antigen Recognition Upon Proteolytic Activation Generation of C225 and 425 Masked mAbs The masked scFvs were produced as secreted proteins from insect cells infected with baculovirus and were purified by Ni-affinity and size exclusion chromatography.

Domain III of the soluble epidermal growth factor receptor (sEGFRdIII, comprising residues 310-512) was cloned into pAcSG2 behind the human EGFR secretion signal sequence. To this was added a flexible, glycine-serine linker containing the matrix metalloproteinase 9 (MMP-9) consensus protease site-VPLSLYS (SEQ ID NO:3) and finally a single chain variable region (scFv) anti-EGFR antibody. The full linker sequence is (GGGSGGGSGGGSVPLSLYSGST-SGSGKSSEGSGSGAQG) (SEQ ID NO:4; MMP-9 protease site is underlined). Both scFv constructs of C225 and 425 were assembled $V_L$-linker-$V_H$. C-terminal FLAG (425 only) and hexahistadine tags (C225 and 425) were also added. This vector was mixed with linearized baculovirus DNA (BD Biosciences), transfected and expanded for three rounds before confirming viral titers. Large-scale expression (5 L) was conducted in suspension culture. The media was separated from cellular material and diafiltered against purification buffer as described previously (Ferguson et al., 2000). Protein purification was accomplished using a nickel-NTA column followed by a HiLoad 26/60 Superdex 200 preparative column (Amersham).

Figure 13:
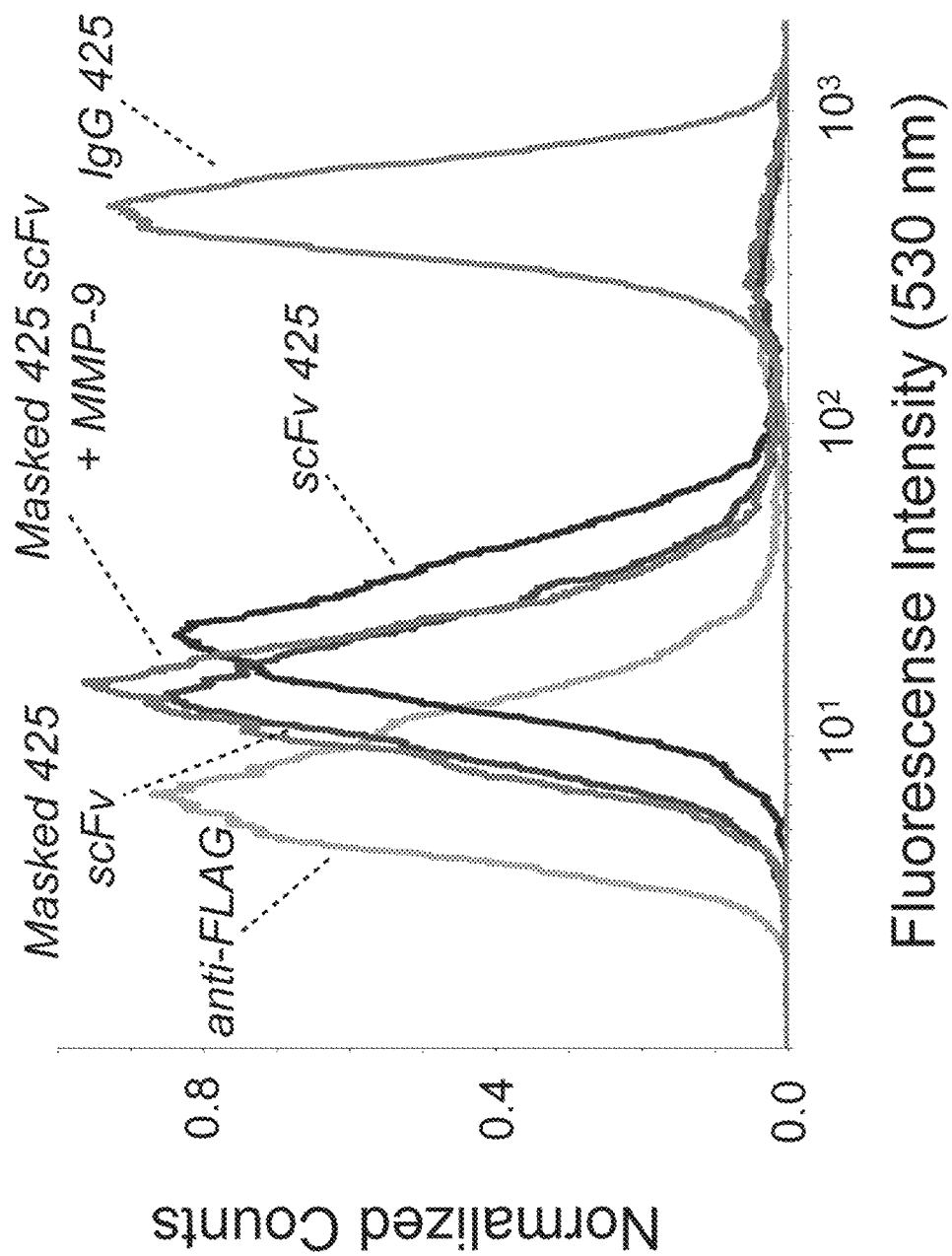
FIG. 13 is a flow cytometry graph illustrating that masked 425 alone does not exhibit an MMP-9 dependent increase in binding. However, the sEGFRdIII-antibody fusion is free to bind before linker digestion, indicating a lack of masking.
Figure 18:
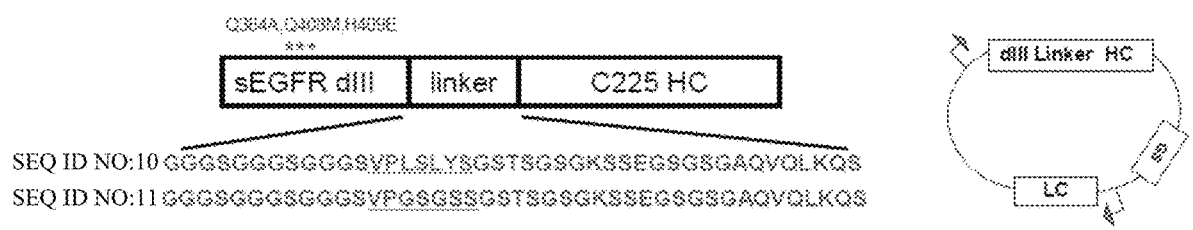
Figure 19:
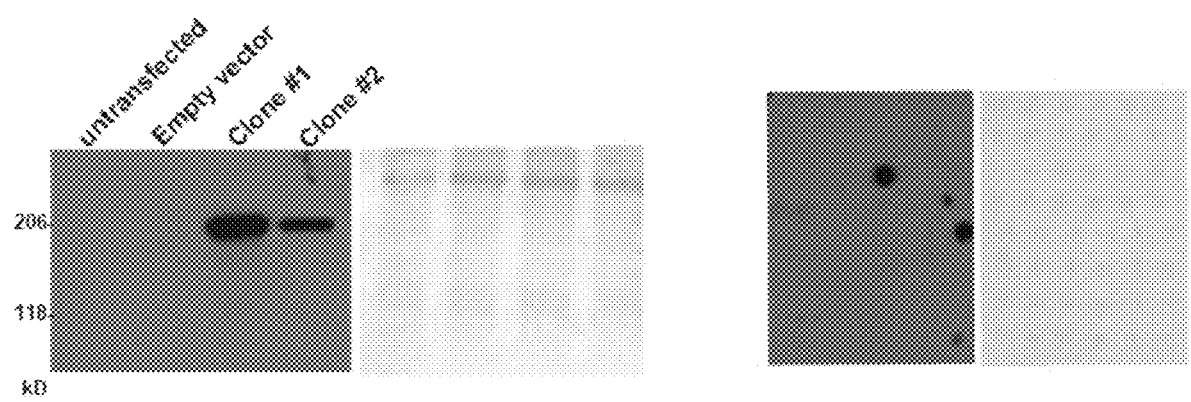
Figure 20:
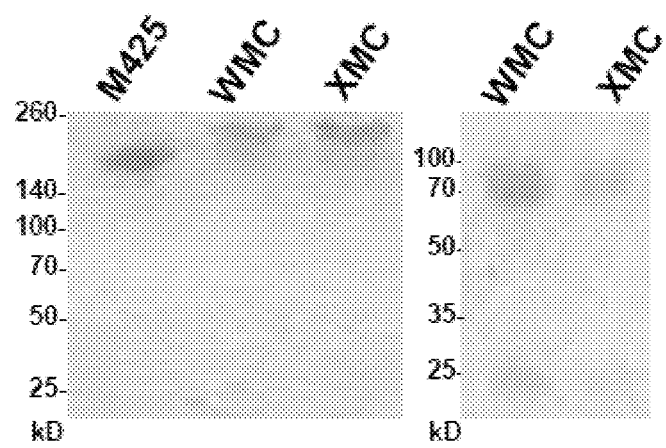
Figure 21:
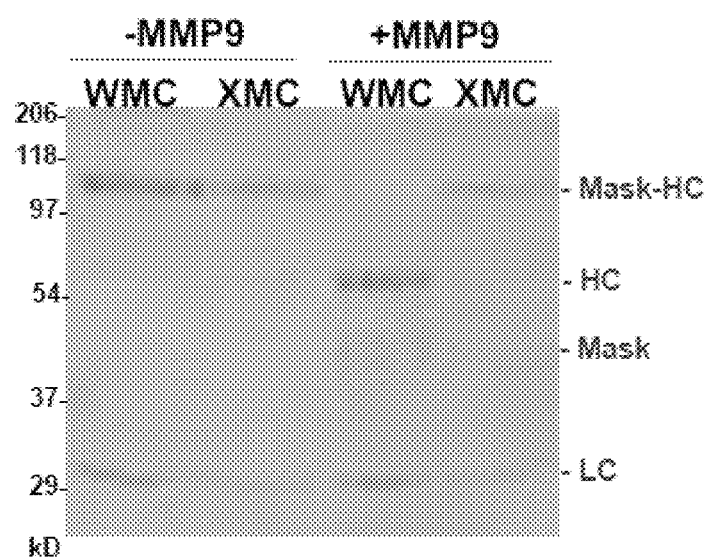
Figure 22A:
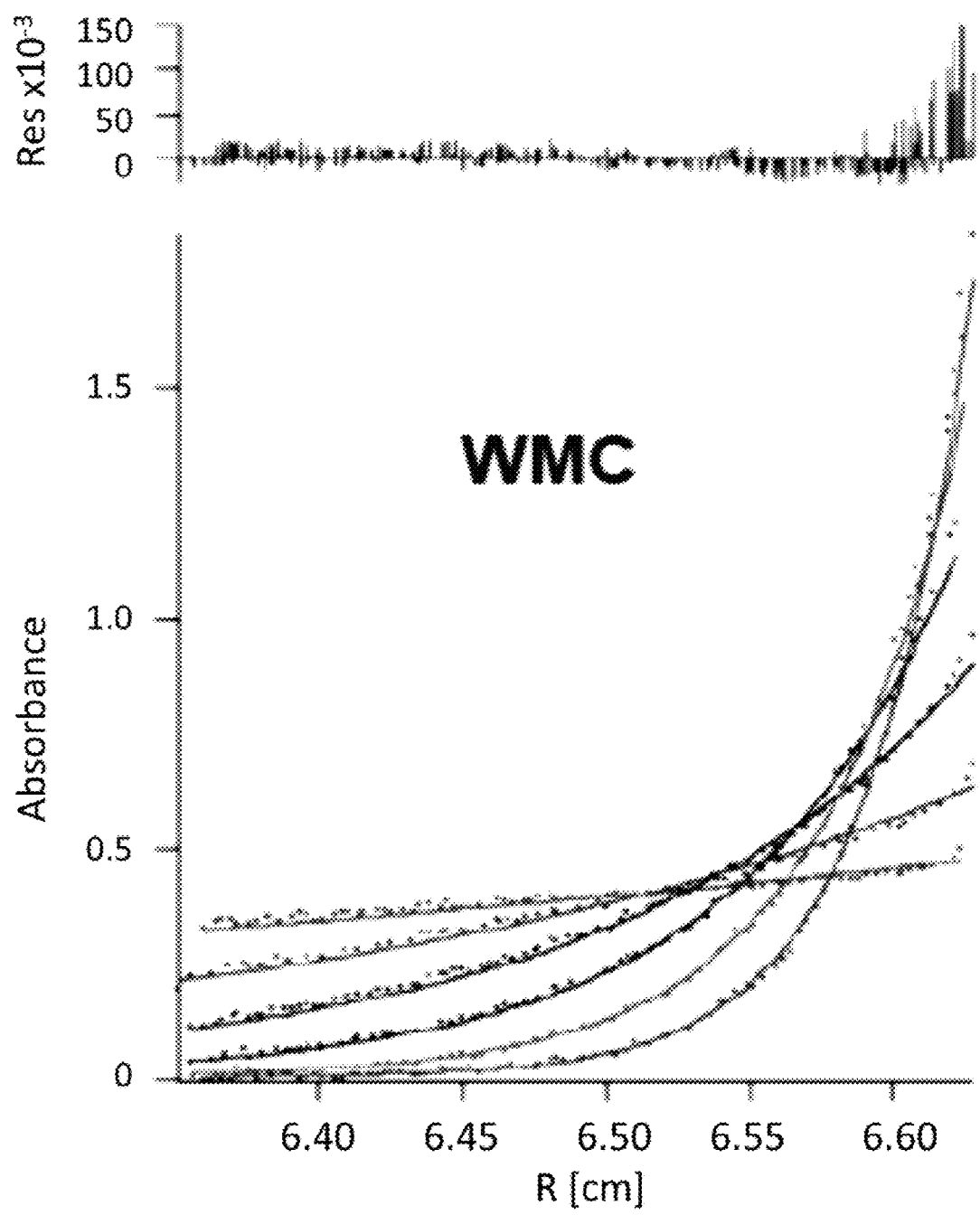
Figure 22B:
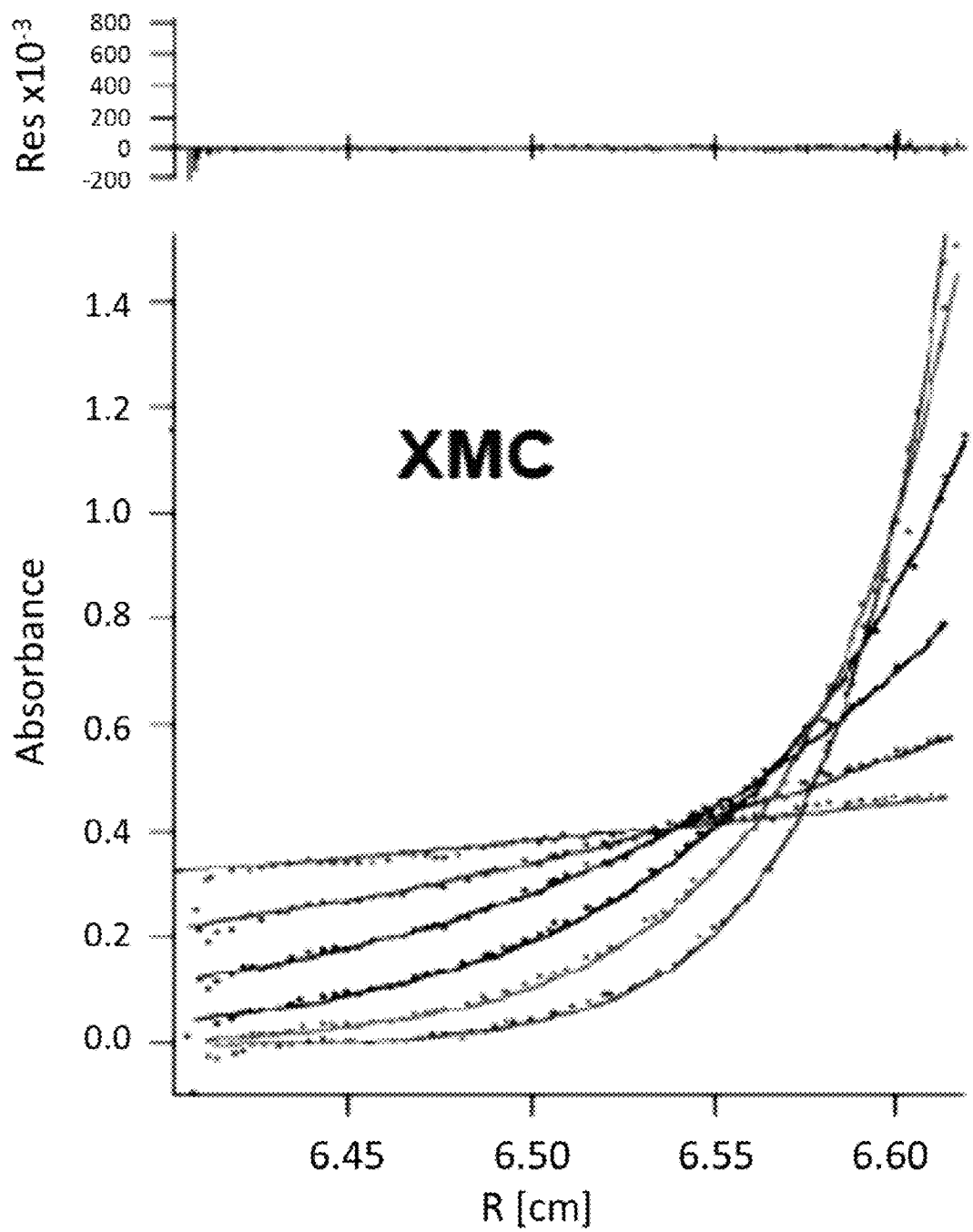
Figure 22C:
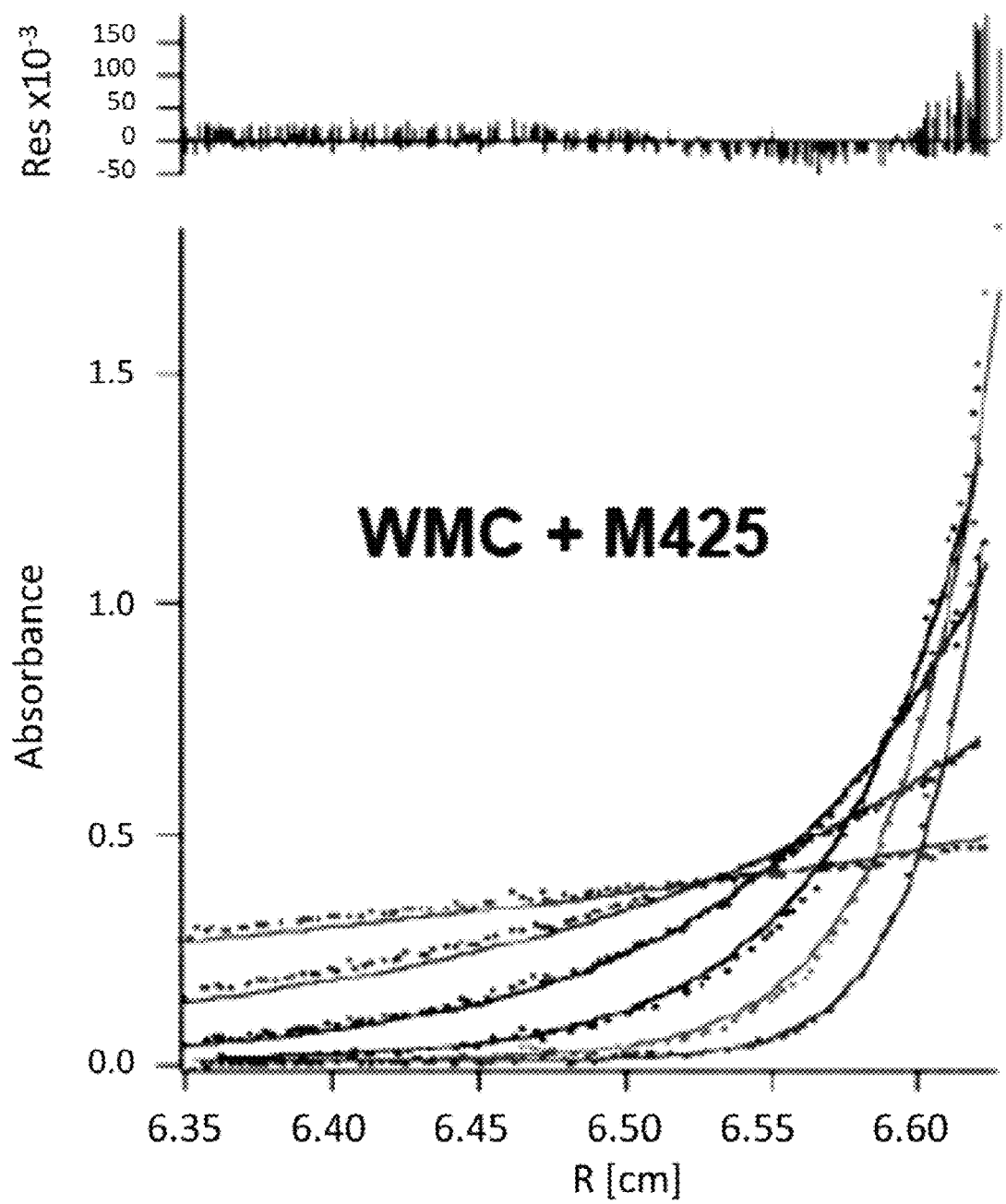
Figure 22D:
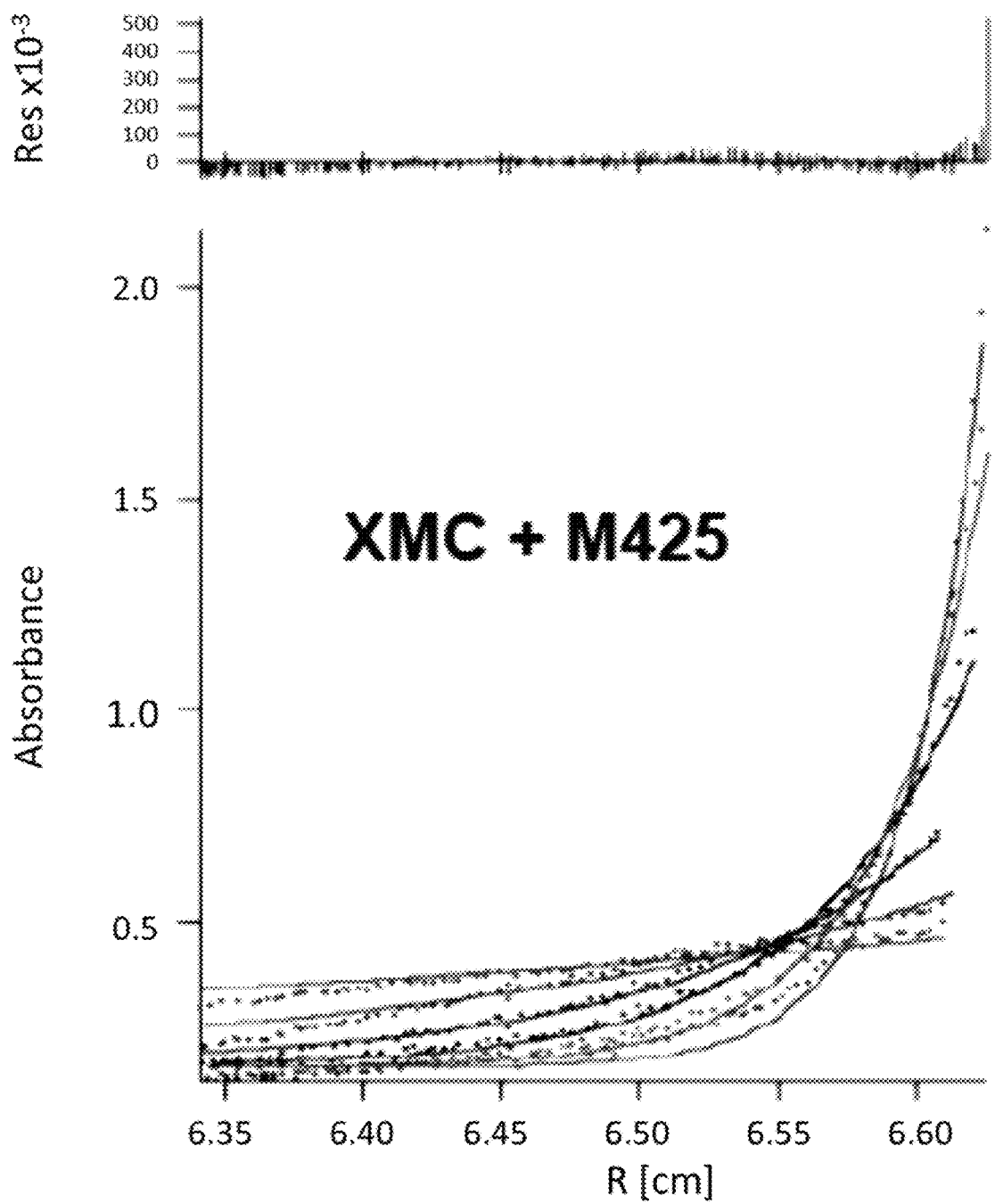
Figure 22E:
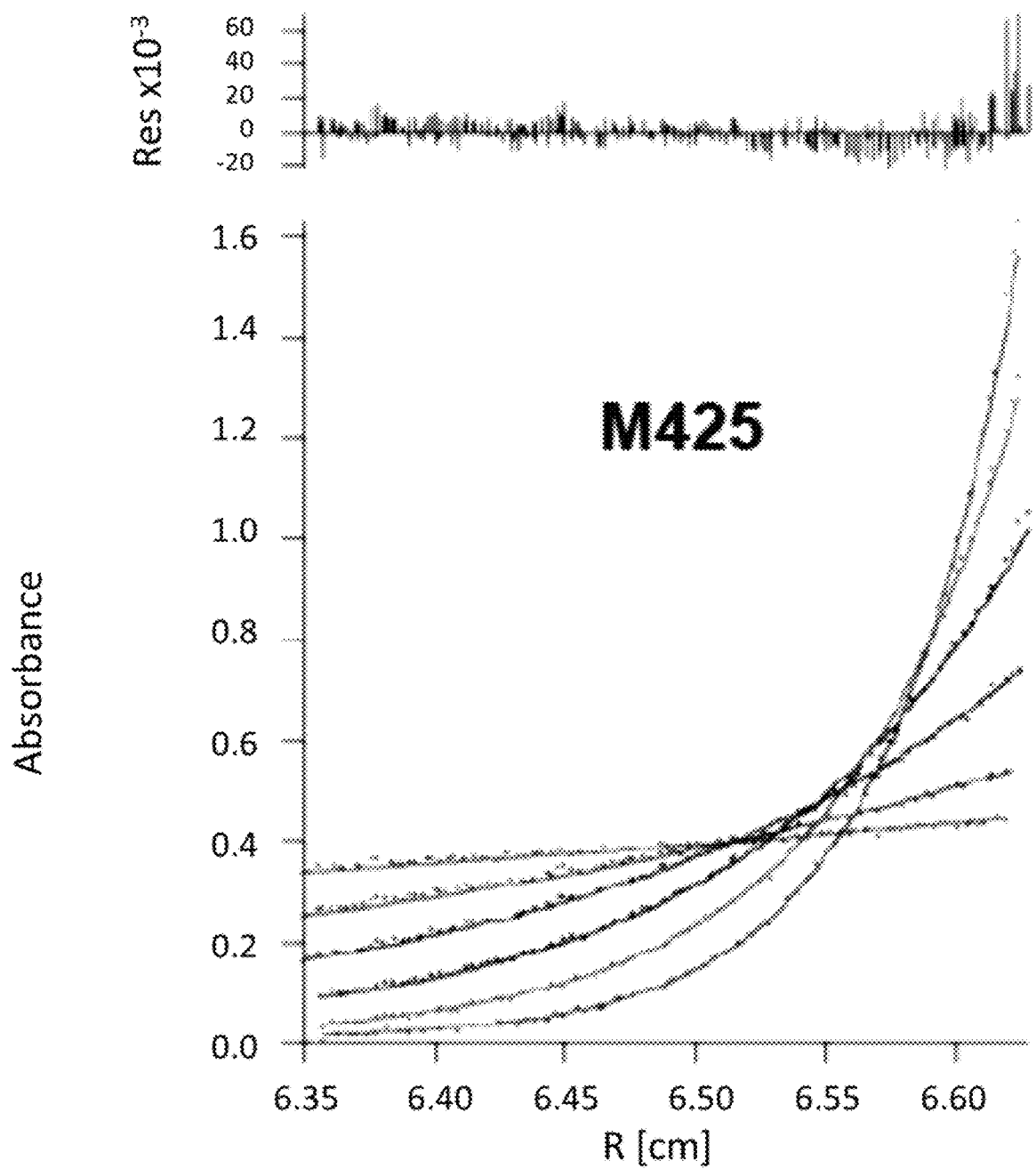
Figure 23:
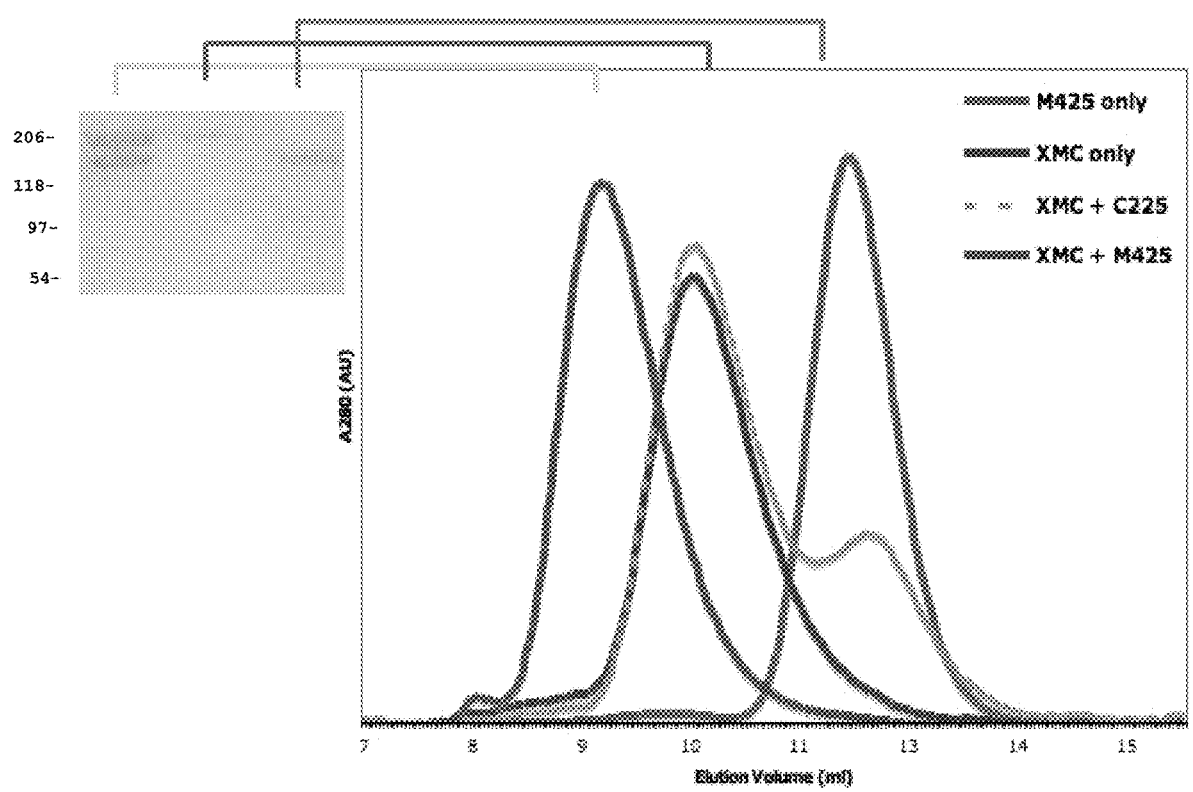
Figure 24:
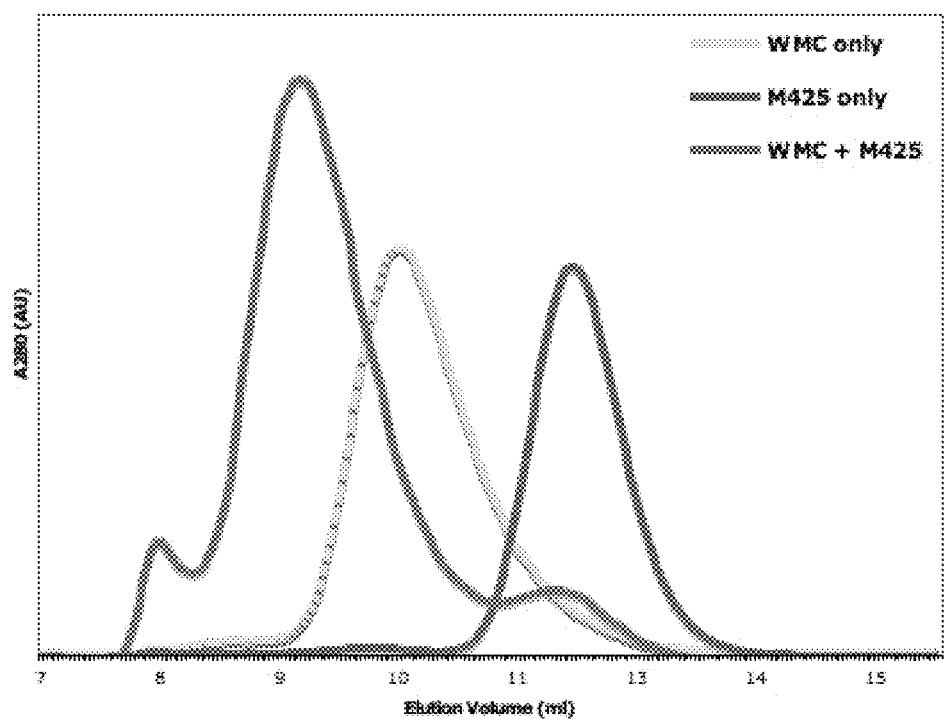
Figure 25:
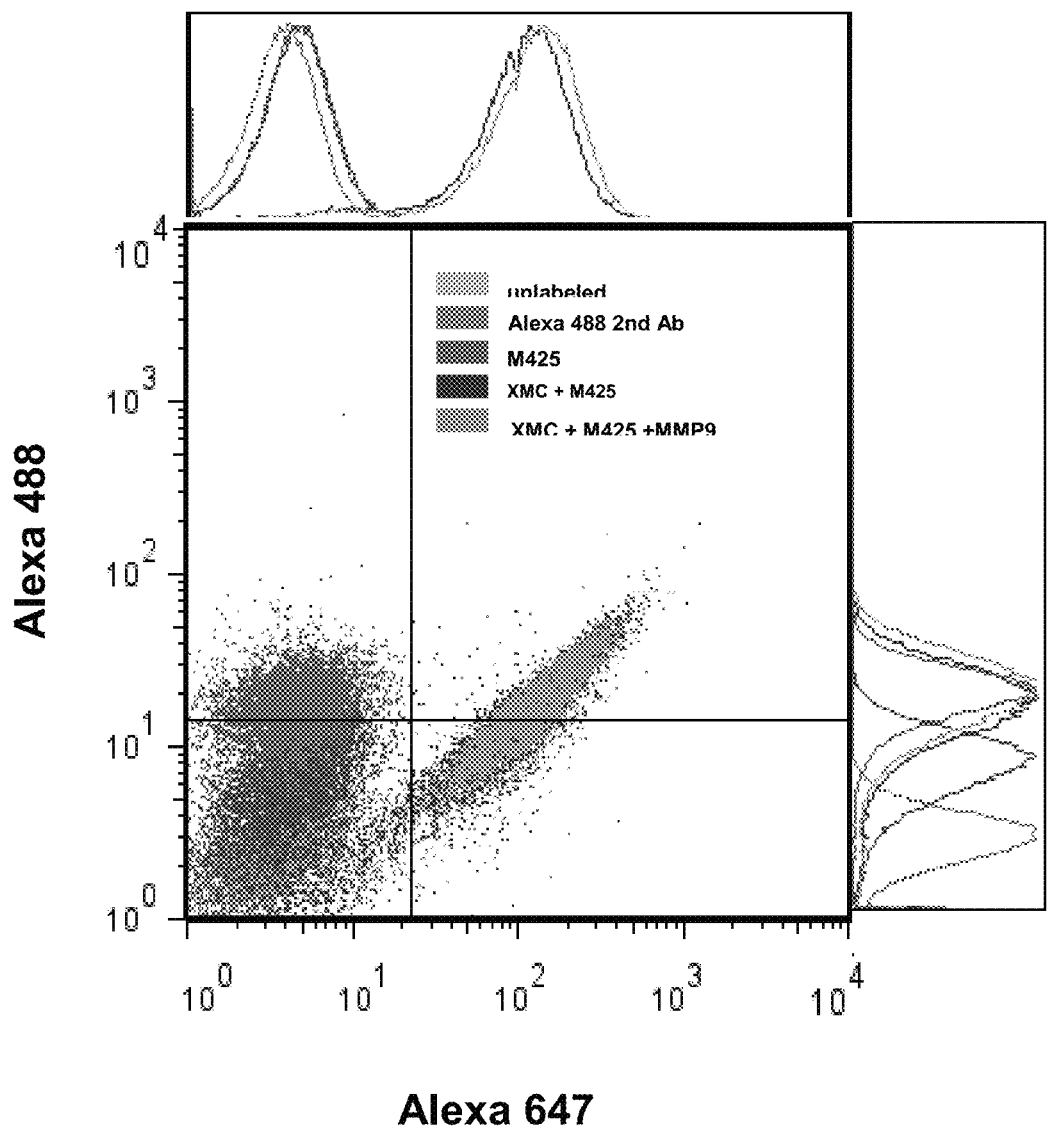
Figure 26:
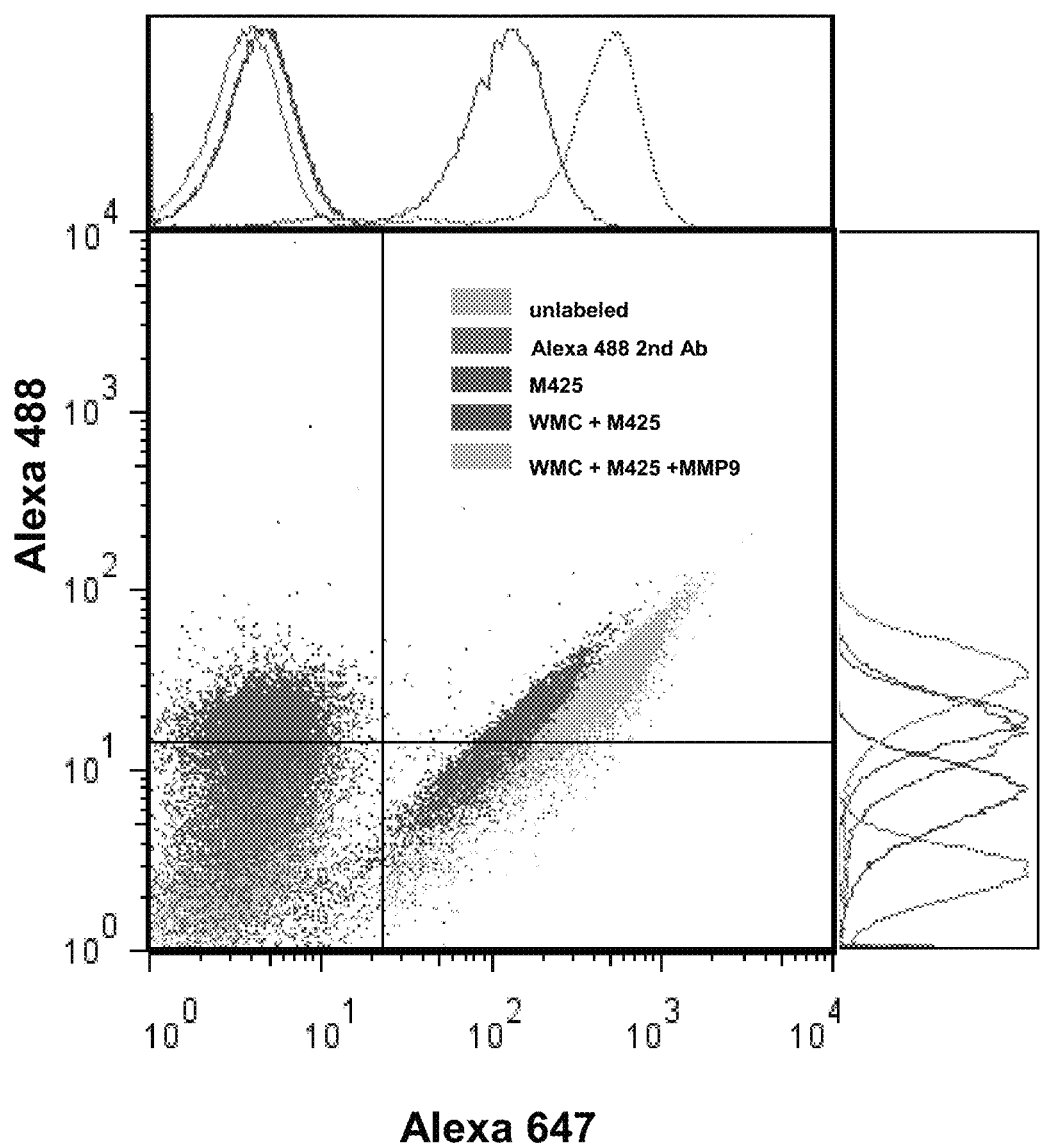

Secreted masked mAbC225 scFv contained a mixture of the expected length and digested fragments. Analytical size exclusion chromatography (SEC) of the purified material indicated dimeric species, but no monomeric or oligomeric species. Treatment of the purified material with MMP-9 and analysis by SEC indicated that the homodimeric complex was cleaved (FIG. 13). In addition, SDS-PAGE of the protease-treated, homodimeric complex indicated that MMP-9 cleavage was specific, producing two bands of the predicted molecular weight and no cleavage of the individual domains or scFv linker. Together, this suggests that the linker may interfere with the intramolecular association of the epitope to the scFv (e.g., a single masked species), potentially reflecting a combination of steric clashes and an entropic penalty. These data provide evidence that it is possible to mask the complement-determining region (CDR) and cleave the masking agent.

Since a dimeric interaction was observed, a heterodimeric or crossed-masked design was also produced to simultaneously deliver two therapeutic antibodies to the tumor site was also considered. The utility of such a design is justified by studies, as described in Example 1, which show that the combination of C225 and 425 act synergistically to inhibit EGF-stimulated cell growth and survival (Kamat et al., 2008), and is more effective in eliciting complement-dependent tumor cell lysis than other combinations of anti-EGFR antibodies with C225 (Dechant et al., 2008). To favor assembly of 'cross-masked' 425/C225 complexes wherein the mask linked to C225 scFv binds to 425 scFv (and vice versa), the native epitopes were altered by introducing point mutations that diminish intramolecular affinity but not intermolecular complex formation. Hexahistidine and FLAG tags facilitated purification and detection. Purification by affinity and size exclusion chromatography of the masked 425 and C225 scFvs yielded undigested material of greater than 95% purity (FIG. 9C). Despite the multivalent nature of the constructs, size exclusion chromatography did not reveal the presence of aggregates.

Purified masked 425 [sEGFRdIII (S460P/G461N)-scFv425; FIG. 15; SEQ ID NO:2 (nucleic acid); SEQ ID NO:6 (amino acid)] and masked C225 [sEGFRdIII (Q384A/Q408M/H409E)-scFv C225; FIG. 14; SEQ ID NO:1 (nucleic acid); SEQ ID NO:5 (amino acid)] were allowed to associate for 20 minutes at 4° C. and then loaded onto a Superdex 200 10/300 GL. Fractions corresponding to the crossmasked reagent were concentrated using a Centricon Spin Concentrator (10 kDa, Millipore). This material was then exchanged 4 times into 2 volumes of reaction buffer: 50 mM Tris, pH 7.4, 150 mM NaCl, 5 mM $CaCl_2$, 0.02% Nonidet P-40 substitute (Backstrom et al., 1996). Active, recombinant MMP-9 (Calbiochem) was incubated with the cross-masked 425/C225 and masked scFvs at a molar ratio of 1:42. The completeness of the reaction was assessed by reducing SDS-PAGE and was at least 95% complete by Coomassie staining. The masked 425 and masked C225 scFvs formed a cross-masked, non-covalent 425/C225 scFv complex, which eluted from a size exclusion column as a symmetric peak consistent with the calculated molecular mass of 106 kDa (FIG. 9B). Both antibody derivatives were completely cleaved by recombinant active MMP-9 into the mask and scFv proteins (FIG. 9C). Samples were immediately frozen at −20° C. until needed for experiments.

Affinity of C225 and 425 Masked mAbs for EGFR Domain III.

Surface Plasmon Resonance Interaction Studies.

Figure 10A:
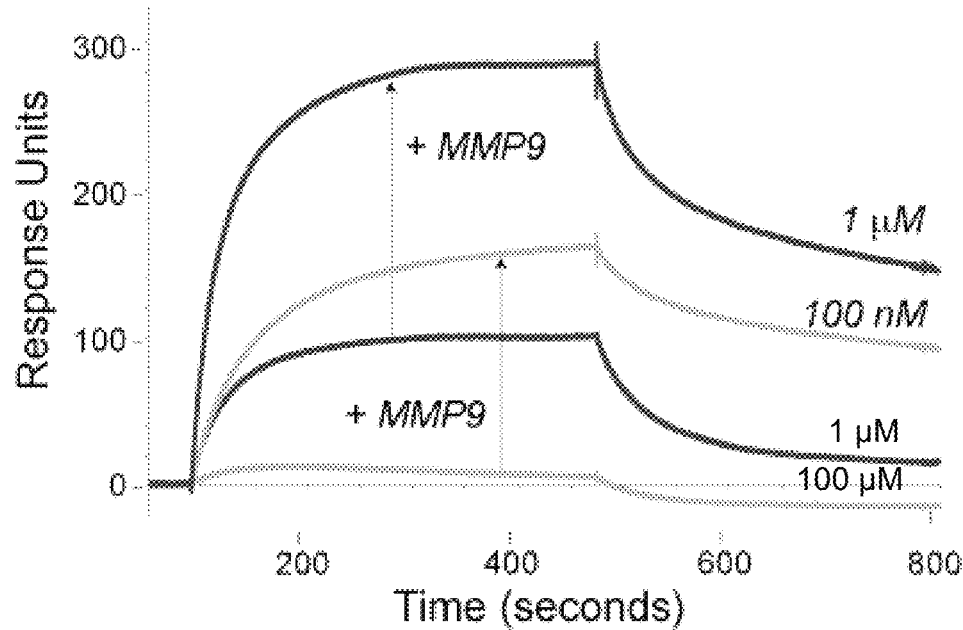
Figure 12A:
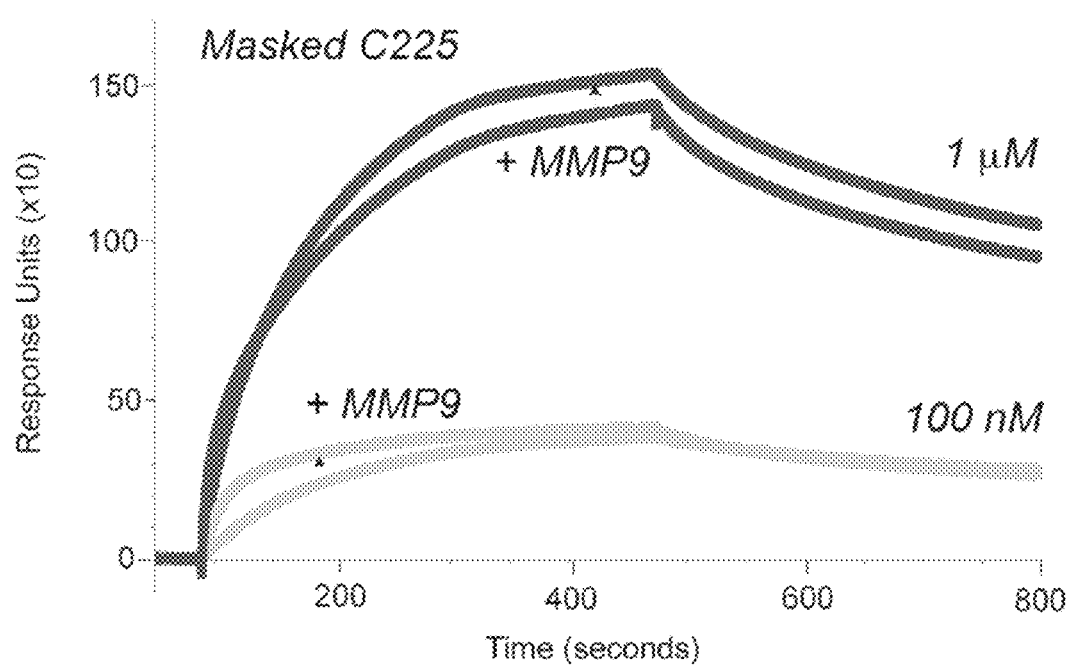
Figure 12:
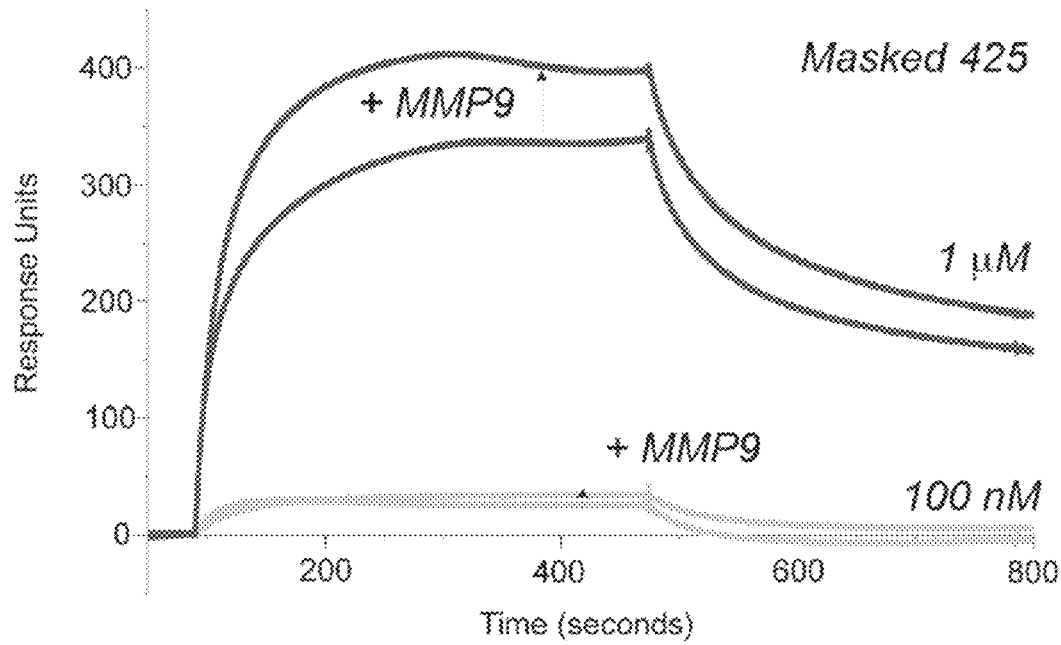

The affinity of masked antibodies for immobilized sEGFRdIII was determined using surface plasmon resonance (SPR) analysis. F(ab)' fragments of the parental antibodies mAb425 and mAbC225 were used as controls to verify the immobilization and stability of the sEGFRdIII over multiple analytical cycles (see supporting data). The affinity of F(ab)' 425 and C225 were 91±23 and 5.3±0.6 nM, respectively (Table 1, below). The scFv constructs bound with weaker affinity of 260±40 and 110±20 nM, respectively. After characterizing these antibody fragments, the masked antibodies were measured singly or as a heterodimer before and after MMP-9 digestion. For masked C225 scFv and masked 425 scFv, no difference in affinity as compared to the respective unmasked scFvs was observed, demonstrating that the point mutations interfere with self-association. However, the CDRs of the cross-masked 425/C225 scFvs were effectively occluded, as shown by weak binding to sEGFRdIII. In contrast, treatment of cross-masked 425/C225 with MMP-9 increased binding affinity by approximately an order of magnitude. Representative traces are shown at 1 μM and 100 nM in FIGS. 10A and 12A-B. Specifically, in the absence of MMP-9, the affinity for sEGFRdIII was 3.5±1.1 μM, but after MMP-9 exposure the affinity increased to 420±270 nM Binding experiments were performed on a BIAcore T100 instrument at 25° C. in HBS-EP buffer (10 mM HEPES, 150 mM NaCl, 3 mM EDTA, pH 8.0 and 0.005% Tween 20). Immobilization was accomplished using standard amine coupling to a CM5 chip. Blank immoblization was used for the reference cell. sEGFR domain III was applied at 50 µg/mL in acetate buffer, pH 5.5 for a target of 5000 response units (3310 RU final). Bioactivity of the chip was confirmed by steady state binding of Fab225 at 30 µL/min. All other analyses were conducted at the same flow rate. Binding was assessed at 1 µM, 100 nM, 50 nM, 25 nM, 12.5 nM and 6.25 nM. The association phase was 380 seconds and dissociation 300 seconds. Regeneration was accomplished using 30 µl of 100 mM glycine, pH 3.0 at a flow rate of 90 µL/min. Steady state measurements were fit to the expression RU= ($R_{max}$*[ ])/([ ]+$K_d$). Each dissociation constant was determined at least three times. The bioactivity of the chip gradually declined over time as a result of the regeneration conditions. However, minimal variation within a run permitted analysis.

TABLE 1

Dissociation constants ($K_D$) of antibody fragments

| Antibody Fragments | Dissociation Constant* (nM) | | Ratio |
|---|---|---|---|
| | (−) MMP-9 | (+) MMP-9 | |
| Cross-masked 425/C225 | 3500 ± 1100 | 420 ± 270 | 8.26 ± 5.92 |
| Masked 425 | 240 ± 100 | 370 ± 110 | 0.66 ± 0.34 |
| Masked C225 | 560 ± 800 | 570 ± 770 | 0.99 ± 1.93 |
| scFv 425 | | 260 ± 40 | 2.87 ± 0.83 |
| Fab 425 | | 91 ± 23 | |
| scFv C225 | | 110 ± 20 | 21.5 ± 4.7 |
| Fab C225 | | 5.3 ± 0.6 | |

*n = 3

Flow Cytometry Interaction Studies.

Figure 10B:
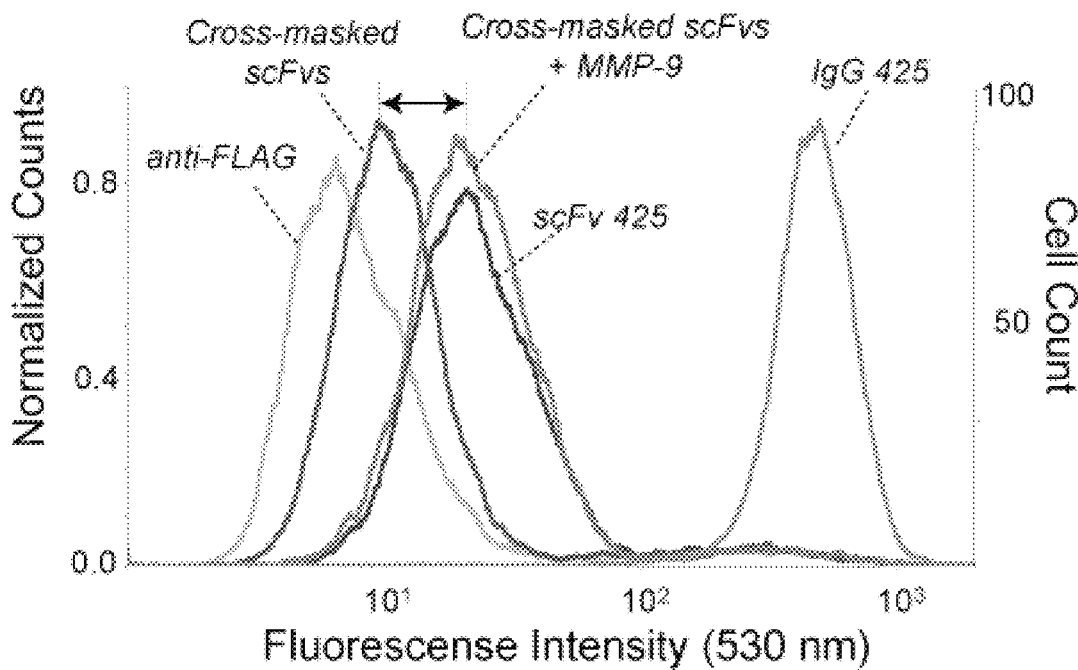
Figure 11:
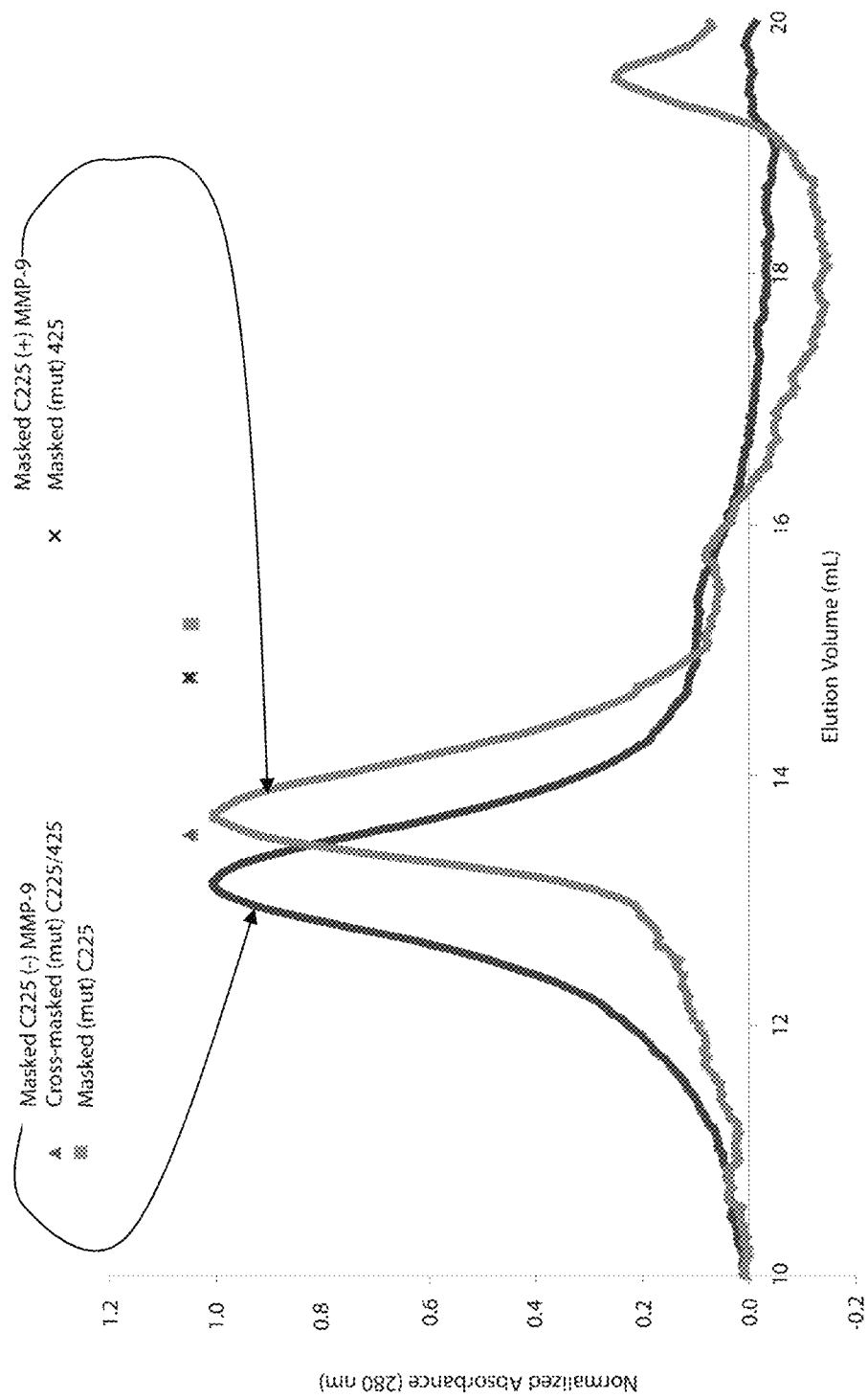

To measure differential affinity in the context of EGFR expressed on target cell surfaces, cross-masked 425/C225 antibody binding to keratinocyte-derived HaCaT cells that express EGFR was also tested. Binding was detected by flow cytometry using an AlexaFluor-labeled anti-FLAG antibody. The antibody only detects the masked 425 because masked C225 lacks a FLAG tag. First, the association of masked 425 with HaCaT cells showed little dependence on MMP-9 digestion (FIG. 13). This is consistent with the intramolecular mask being unable to occlude the linked 425 antibody and consistent with the SPR results. Next, it was observed that the cross-masked 425/C225 had low affinity for the HaCaT cells (FIG. 10B), whereas cleavage of the antibody derivatives with MMP-9 markedly enhanced their binding (FIG. 10B). Binding of the digested cross-masked 425/C225 scFvs was comparable to that of the 425 scFv alone (FIG. 10B), indicating that the N-terminal extension remaining after digestion does not compromise binding.

Flow cytometric analyses were carried out using mAb425 and anti-FLAG (clone M2, Sigma) amine-conjugated to Alexa Fluor 488 according to the manufacturer's protocol (Molecular Probes). Between 4-8 Alexa 488 molecules were bound per antibody as estimated by measuring the optical density at 280 nm and 494 nm. For FACS analysis, HaCaT cells were detached with trypsin/EDTA. The trypsin was inactivated with DMEM/FBS and the cells were collected and resuspended in wash buffer (1×PBS containing 1% BSA). Approximately 1,000,000 cells were incubated at 4° C. in 50 µl of digested and undigested cross-masked 425/C225 as indicated. After 45 minutes of incubation, cells were washed twice with wash buffer and incubated for 20 minutes with the anti-FLAG secondary antibody or mAb425. Samples were analyzed on a FACSCalibur (BD Biosciences). The specificity of scFv 425 was confirmed by pre-incubation with unlabeled mAb425. scFv C225 did not yield any signal above the anti-FLAG control since it lacks the FLAG tag (FIG. 13).

Expression and Cleavage by MMP9 of Cetuximab Masked with EGFR Domain III Linked Via a Cleavable or Non-Cleavable Linker.

Mask Design.

FIG. 18 shows the Design of a mask. Briefly, EGFR domain III is fused to heavy chain of Cetuximab via a MMP9 cleavable (top line) or non-cleavable linker (bottom line). The mask-heavy chain and light chain of Cetuximab are cloned into a dual expression GS selection vector.

Transient Transfection.

4 μg of dual vector and 10 μl of Lipofectamine 2000 were mixed in 500 μl of Opti-MEM and applied to 0.5×$10^6$ COS 7 cells in 6-well plates. Culture supernatants were collected 72 h post-transfection. FIG. 19 (left) shows transient and stable expression of mask Cetuximab by Western blot with an anti-human Fc-HRP antibody of COS-7 culture supernatants three days after transient transfection.

Stable Cell Line Transfection and Selection.

100 μg of linearized dual vector were nucleofacted into 5×106 NS0 cells and plated into 96 wells plates by limited dilution 24 h later. Single colonies were assayed for expression 3 weeks later, and positive colonies were expanded. The right panel of FIG. 19 shows dot blot identification of stably-transfected mask-Cetuximab NS0 cell lines. Culture supernatant of single colony clones were spotted and blotted by anti-human Fc-HRP antibody. This indicates that masked Cetuximab can be stably expressed in NS0 cells.

Mmp9 Cleavage.

Substrate proteins were exchanged into 50 μl MMP9 cleavage buffer. 40-80 μg of MMP9 were added and incubate at 37° C. for at least 3 h to overnight. FIG. 20 shows a non-reducing (left) and reducing (right) SDS-PAGE of mask Cetuximab with cleavable (WMC) and non-cleavable (XMC) linker, confirming presence of indicate proteins. FIG. 21 establishes that the masked Cetuximab with the cleavable linker is able to be cleaved by MMP9 in vitro.

Size Exchange Chromatography.

80 μl of protein in PBS were separated on a Sephrodex 200 analytical SEC and were eluted into PBS in 0.5 ml fractions at 4° C. Both WMC and XMC could form a complex with Matuzumab, indicated by the shift in the elution peak. Peak fractions from XMC+M425, XMC and M425 were resolved on a non-reducing SDS-PAGE. Mask Cetuximab did not form a complex with Cetuximab (FIGS. 23 and 24).

Ultracentrifugation (AUC).

100 μl of 1 mg/ml of isolated complexes were ultracentrifuged in PBS at 3000, 6000, 9000, 12,000, 15,000 rpm at 20° C. FIGS. 22A-E show the determination of the molecular weight of the referenced samples and the stoichiometry of the mask Cetuximab-Matuzumab cross-masked complex. Masked Cetuximab was shown to be able to form a complex with Matuzumab in a 1:1 ratio.

FACS.

Alexa 647-labeled WMC/XMC complexed with M425 were isolated from SEC, 50 μl of 5 nM complexes treated with MMP9, and mixed with 0.5×106 trypsinized MDA-MB-468 cells in 50 μl of 1% BSA in PBS. M425 were labeled with Alexa 488 anti-human IgG secondary antibodies. MMP9 cleavage released masked Cetuximab-matuzamb complex for binding to EGFR over-expressing tumor cells (FIGS. 25 and 26).

Example 3: Non-Covalent Masking of Trastuzumab with a HER2 Domain IV-MMP9-Fc Bivalent Mask Construct Design.

Figure 27:
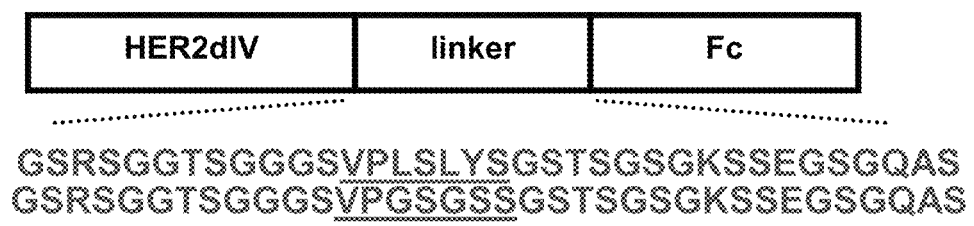

HER2 domain and the Fc portion of an IgG1 were connected by a flexible linker containing a MMP9 cleavage site (top sequence underlined). As a control, a version with a mutated MMP9 cleavage site (bottom sequence underlined) was also constructed (FIG. 27).

Expression and Purification.

Figure 28:
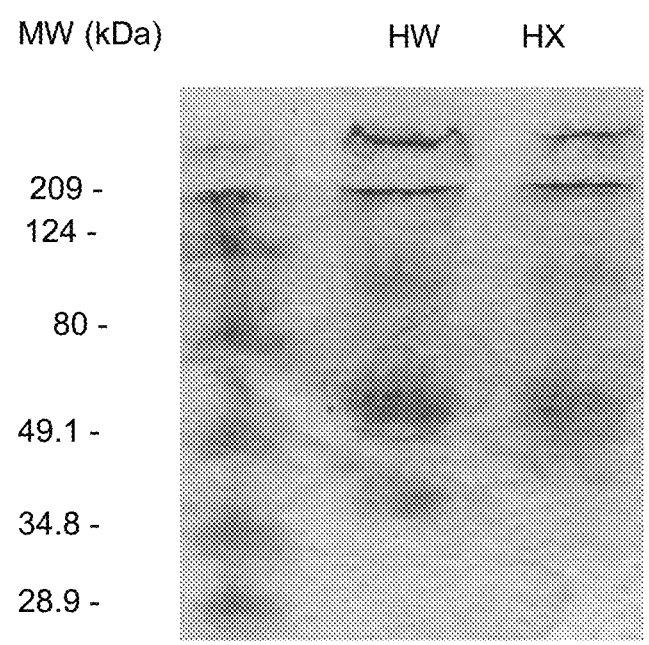
Figure 29:
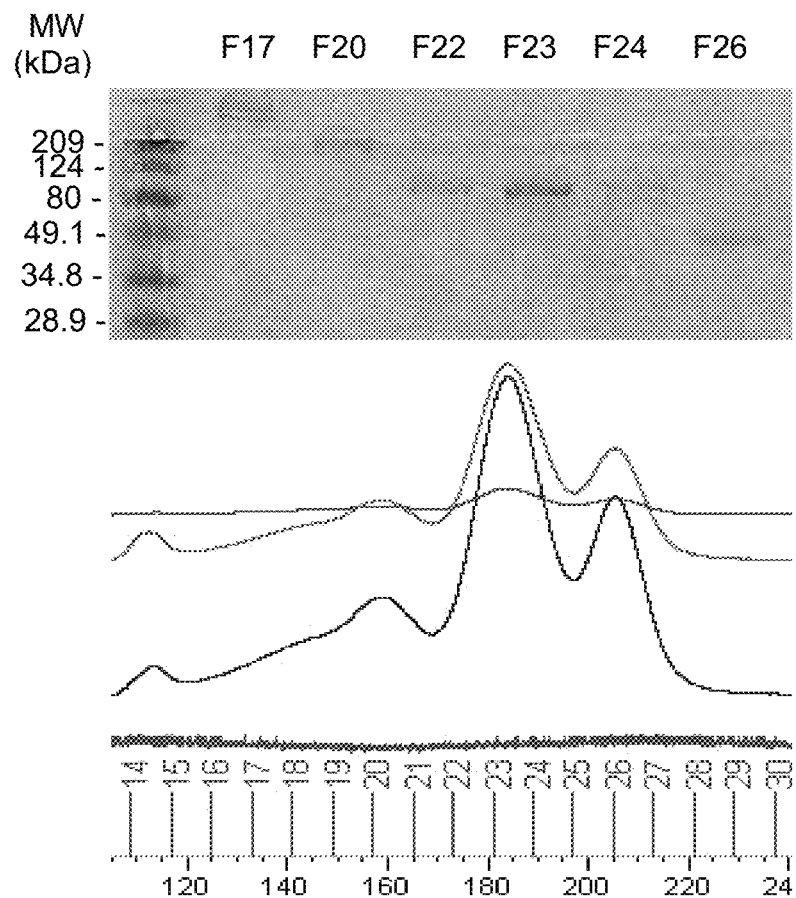

The constructed were separately cloned into a pAcGP67A baculovirus transfer vector. Each vector was co-transfected with BD BaculoGold Linearized Baculovirus DNA into Sf9 cells for baculovirus production. After three rounds of amplification a virus titer of about $2\times10^8$/ml virus particles was reached. High Five cells at $2\times10^6$/ml culture density were transfected with the baculoviruses at MOI of 3. The culture supernatants were harvested 72 hrs post transfection. The retrieved media were clarified and passed through a Protein A agarose bead column. The column was washed extensively with PBS, and the H4Fc was eluted with 0.1M glycine at pH3 into 0.1 volume of 1M Tris at pH9 for neutralization. FIG. 28 shows that the transfection and culture produced the H4Fc dimer, which is 79 kDa. The band below the dimer is likely the Fc alone, indicating that some degradation occurred during expression. The also protein tends to aggregate at high concentrations. Therefore, the eluted H4Fc was further purified on a Superdex 200 size exclusion column. The protein was eluted from about 170-195 ml, or fractions 22 to 24. A portion of the SEC trace and a non-reducing SDS-PAGE (FIG. 29) show the H4Fc eluted from fractions 22-24, as well as two aggregation species in F17 and F20 and a degradation product, likely the Fc portion, in F26.

Binding of H4Fc to Trastuzumab.

Figure 30:
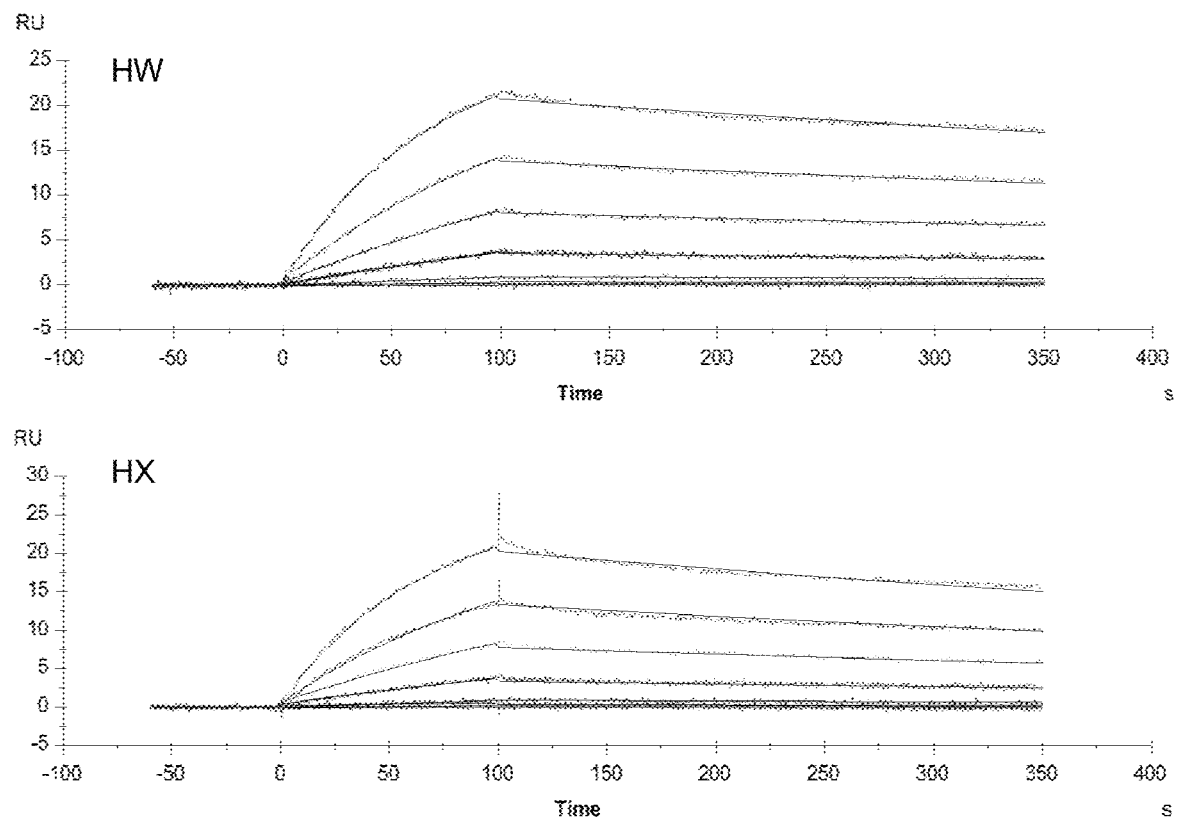
Figure 31:
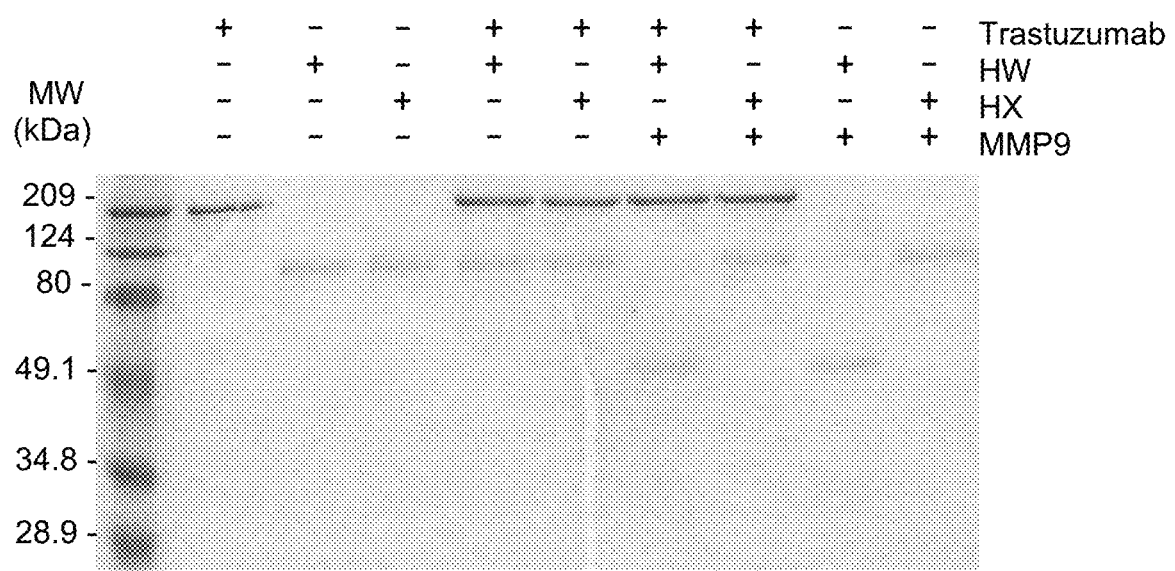
Figure 32:
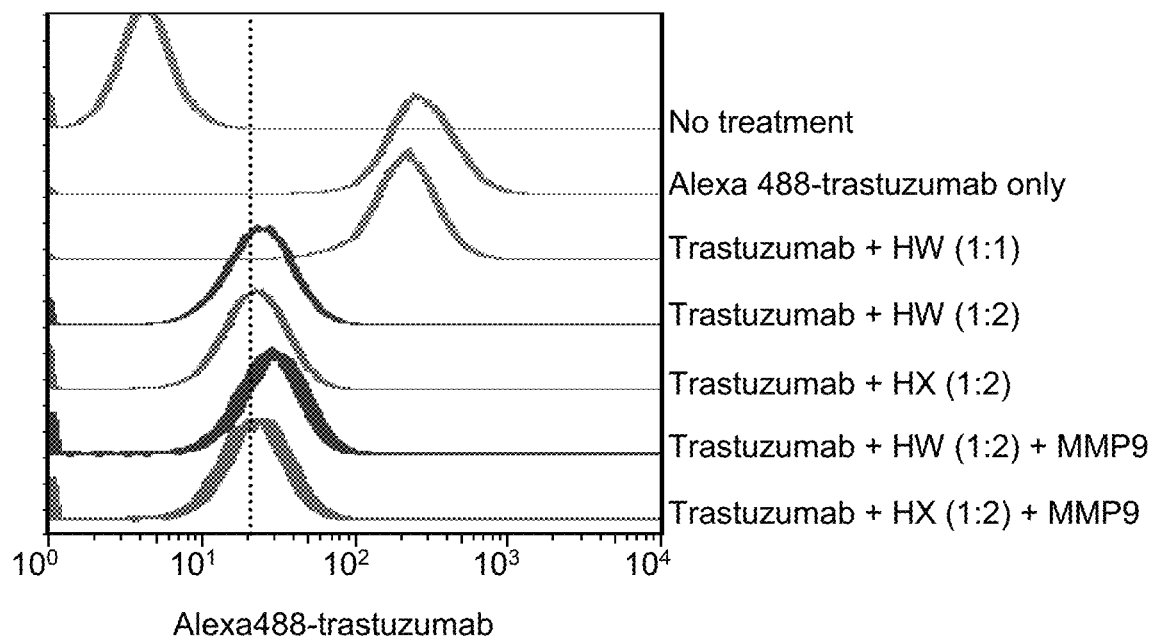

The purified H4Fc with either the wildtype or the mutated MMP9 cleavage sequence were tested by SPR for binding to the Trastuzumab. Fab portion of Trastuzumab was immobilized on the CM5 chip, and the H4Fc's were flown over the chip (FIG. 30). For the wildtype H4Fc, ka=1.377E+4 1/Ms, kd=8.641E-4 1/s; KD=6.277E-8 M; as for the mutated version, KD=$8.979\times10^{-8}$ M; ka=$1.344\times10^4$, kd=0.001207.

Mmp9 Cleavage.

The presence of the MMP9 cleavage within linker is to release the mask from Trastuzumab when the complex reaches the tumor microenvironment. To test if the MMP9 linker is active when the mask is in complex with Trastuzumab, the H4Fc's were incubated with Trastuzumab at equal molar concentration for 20 min, room temperature, and then MMP9 was added for an overnight incubation at 37° C. The proteins were resolved on a non-reducing SDS-PAGE (FIG. 31). As expected, the H4Fc with the wildtype MMP9 cleavage site was cleaved in the presence or absence of Trastuzumab, while the mutated H4Fc showed no cleavage by recombinant MMP9.

H4Fc Inhibits Trastuzumab Binding to SKBR3 Cells.

Alexa 488 labeled Trastuzumab was incubated with either H4Fc's at a 1:1 or 1:2 ratio for 20 min at room temperature, and then MMP9 was added for incubated an overnight incubation at 37° C. The mixtures were then applied to trypsinized SKBR3 cell suspensions for 1 hr, washed thoroughly, and subjected to FACS analysis. As shown in FIG. 32, the binding of the mAb to SKBR3 cells showed a dose-dependent inhibition by the increasing amount of H4Fc in the system. The addition of MMP9 to the wildtype H4Fc containing sample restored some binding of the mAb to cells. On the other hand, the mutated H4Fc containing samples showed no difference whether MMP9 was added or not.

Example 4: Modulation of Antibody Binding Kinetics Via Non-Covalent Masking

Diffraction Studies of Protein A and Protein L Bound to Trastuzumab.

The Trastuzumab Fab was co-crystallized with protein A and protein L. The crystal structure provides the basis to rationally design steric masks activated at the tumor microenvironment. As determined by the structures (FIGS. 34A-D) and the X-ray diffraction data for the Trastuzumab Fab (FIG. 35), Protein A and L have been shown to be useful as 'additives' for Fabs that do not readily crystallize and/or to improve the diffraction limits. The data set was collected at SSRL, the structure was solved by MR and refined using phenix software. Maps were contoured at 1.0 and figures were made using pymol.

Hydrodynamic Analysis.

To characterize the interaction between the protein A-protein L mask and the Trastuzumab Fab, a sedimentation equilibrium analysis was performed by analytical ultracentrifugation, using an admixture of protein A-protein L mask (FIG. 36B), Trastuzumab Fab (FIG. 36C), and the protein A-protein L mask and Trastuzumab Fab (FIG. 36D). As shown by FIGS. 36A-D and the data in Table 2 (below), the hydrodynamic studies indicate a 1:1 complex.

TABLE 2

Expected and calculated masses derived from sed. eEq. experiments

| Sample | Expected MW | AUC Experimental MW |
|---|---|---|
| mask | 14,985 | 16,082 +/− 162.70 |
| Fab | 46,755 | 45,909 +/− 166.41 |
| mask + Fab | 61,740 | 56,380 +/− 160.33 |

Spr Analysis.

FIGS. 37A-C show that the protein L-A mask binds with higher affinity than protein A or protein L alone as illustrated by surface plasmon resonance (SPR) analysis of the binding affinity of protein L (FIG. 37*a*), protein L (FIG. 37*b*) and protein A-protein L mask for Trastuzumab Fab (FIG. 37*c*), The concentration range for a-b is 3.2 nM to 5 μM and 10 pM to 1 μM. The binding affinity values are summarized in Table 3 (below).

TABLE 3

| Sample | KD | chi2 |
|---|---|---|
| Protein A | 29.98 uM | 0.0157 |
| Protein L | 173.5 nM | 17.5 |
| Protein A-Protein L mask | 86.2 nM | 2.04 |

FIGS. 38A-D show a comparison of on-rates of masked and unmasked Trastuzumab Fab binding to HER2 by illustrating an SPR Analysis of Trastuzumab Fab binding to HER2 (FIGS. 38*a*-38*b*) and Trastuzumab Fab with excess protein A-protein L mask binding to HER2 (FIGS. 38*c*-38*d*). Panels b and d compare the on rates of the two Fab to HER2. The on-rate is slower for the masked, illustrating that an antibody can be effectively masked to prevent off-target effects using a generic protein A-protein L mask.

REFERENCES

The References listed below, and all references cited in the specification are hereby incorporated by reference in their entirety as if fully set forth herein.

Adams, G. P.; Weiner, L. M., *Nat Biotechnol* 2005, 23, (9), 1147-57.

Arkin M, Lear J D. A new data analysis method to determine binding constants of small molecules to proteins using equilibrium analytical ultracentrifugation with absorption optics. Anal Biochem 2001; 299:98-107.

Backstrom, J. R.; Lim, G. P.; Cullen, M. J.; Tokes, Z. A., *J Neurosci* 1996, 16, (24), 7910-9.

Baselga J, Arteaga C L. Critical update and emerging trends in epidermal growth factor receptor targeting in cancer. J Clin Oncol 2005; 23:2445-59.

Biscardi J S, Belsches A P, Parsons S J. Characterization of human epidermal growth factor receptor and c-Src interactions in human breast tumor cells. Mol Carcinog 1998; 21:261-72.

Cox, G.; Jones, J. L.; O'Byrne, K. J., *Clin Cancer Res* 2000, 6, (6), 2349-55.

Dechant, M.; Weisner, W.; Berger, S.; Peipp, M.; Beyer, T.; Schneider-Merck, T.; Lammerts van Bueren, J. J.; Bleeker, W. K.; Parren, P. W.; van de Winkel, J. G.; Valerius, T., *Cancer Res* 2008, 68, (13), 4998-5003.

DeLano W L. Unraveling hot spots in binding interfaces: progress and challenges. Curr Opin Struct Biol 2002; 12:14-20.

Ferguson K M. Active and inactive conformations of the epidermal growth factor receptor. Biochem Soc Trans 2004; 32:742-5.

Ferguson, K. M.; Darling, P. J.; Mohan, M. J.; Macatee, T. L.; Lemmon, M. A., *Embo J* 2000, 19, (17), 4632-43.

Friedman, L. M.; Rinon, A.; Lyass, L.; Bacus, S. S.; Sela, M.; Yarden, Y., *Proc. Natl. Acad. Sci. U.S.A.* 2005, 102, (6), 1915-20.

Gill G N, Kawamoto T, Cochet C, Le A, Sato J D, Masui H, McLeod C, Mendelsohn J. Monoclonal anti-epidermal growth factor receptor antibodies which are inhibitors of epidermal growth factor binding and antagonists of epidermal growth factor binding and antagonists of epidermal growth factor-stimulated tyrosine protein kinase activity. Journal of Biological Chemistry 1984; 259:7755-60.

Jost M, Huggett T M, Kari C, Rodeck U. Matrix-independent survival of human keratinocytes through an EGF receptor/MAPK-Kinase-dependent pathway. Molecular Biology of the Cell 2001a; 12:1519-27.

Jost M, Huggett T M, Kari C, Boise L H, Rodeck U. Epidermal growth factor receptor dependent control of keratinocyte survival and Bcl-xL expression through a MEK-dependent pathway. Journal of Biological Chemistry 2001b; 276:6320-6.

Kamat, V.; Donaldson, J. M.; Kari, C.; Quadros, M. R.; Lelkes, P. I.; Chaiken, I.; Cocklin, S.; Williams, J. C.; Papazoglou, E.; Rodeck, U., *Cancer Biol Ther* 2008, 7, (5), 726-33.

Kim E S, Khuri F R, Herbst R S. Epidermal growth factor receptor biology (IMC-C225). Curr Opin Oncol 2001; 13:506-13.

Krishnamurthy, V. M.; Semetey, V.; Bracher, P. J.; Shen, N.; Whitesides, G. M., *J Am Chem Soc* 2007, 129, (5), 1312-20.

Lacouture, M. E.; Boerner, S. A.; Lorusso, P. M., *Clin Lung Cancer* 2006, 8 Suppl 1, S36-42.

Lax I, Fischer R, Ng C, Segre J, Ullrich A, Givol D, Schlessinger J. Noncontiguous regions in the extracellular domain of EGF receptor define ligand-binding specificity. Cell Regul 1991; 2:337-45.

Li S, Schmitz K R, Jeffrey P D, Wiltzius J J, Kussie P, Ferguson K M. Structural basis for inhibition of the epidermal growth factor receptor by Cetuximab. Cancer Cell 2005; 7:301-11.

Lynch, T. J., Jr.; Kim, E. S.; Eaby, B.; Garey, J.; West, D. P.; Lacouture, M. E., *Oncologist* 2007, 12, (5), 610-21.

Masui H, Kawamoto T, Sato J D, Wolf B, Sato G, Mendelsohn J. Growth inhibition of human tumor cells in athymic mice by anti-epidermal growth factor receptor monoclonal antibodies. Cancer Res 1984; 44:1002-7.

Mendelsohn J, Baselga J. The EGF receptor family as targets for cancer therapy. Oncogene 2000; 19:6550-65.

Moscatello D K, Montgomery R B, Sundareshan P, McDanel H, Wong M Y, Wong A J. Transformational and altered signal transduction by a naturally occurring mutant EGF receptor. Oncogene 1996; 13:85-96.

Murthy U, Basu A, Rodeck U, Herlyn M, Ross A H, Das M. Binding of an antagonistic monoclonal antibody to an intact and fragmented EGF-receptor polypeptide. Arch Biochem Biophys 1987; 252:549-60.

Nagane M, Lin H, Cavenee W K, Huang H J. Aberrant receptor signaling in human malignant gliomas: mechanisms and therapeutic implications. Cancer Lett 2001; 162:17-21.

Nahta R, Hung M C, Esteva F J. The HER-2-Targeting Antibodies Trastuzumab and Pertuzumab Synergistically Inhibit the Survival of Breast Cancer Cells. Cancer Res 2004; 64:2343-6.

Ogiso H, Ishitani R, Nureki O, Fukai S, Yamanaka M, Kim J H, Saito K, Sakamoto A, Inoue M, Shirouzu M, Yokoyama S. Crystal structure of the complex of human epidermal growth factor and receptor extracellular domains. Cell 2002; 110:775-87.

Riemer, A. B.; Kurz, H.; Klinger, M.; Scheiner, O.; Zielinski, C. C.; Jensen-Jarolim, E., *J Natl Cancer Inst* 2005, 97, (22), 1663-70.

Rodeck, U., *J Cell Physiol* 2009, 218, (1), 32-4.

Rodeck U, Herlyn M, Herlyn D, Molthoff C, Atkinson B, Varello M, Steplewski Z, Koprowski H. Tumor growth modulation by a monoclonal antibody to the epidermal growth factor receptor: immunologically mediated and effector cell-independent effects. Cancer Res 1987; 47:3692-6.

Segaert, S.; Van Cutsem, E., *Ann Oncol* 2005, 16, (9), 1425-33.

Schmiedel, J.; Blaukat, A.; Li, S.; Knochel, T.; Ferguson, K. M., *Cancer Cell* 2008, 13, (4), 365-73.

Swinson, D. E.; Cox, G.; O'Byrne, K. J., *Br J Cancer* 2004, 91, (7), 1301-7.

Thali M, Moore J P, Furman C, Charles M, Ho D D, Robinson J, Sodroski J. Characterization of conserved human immunodeficiency virus type 1 gp120 neutralization epitopes exposed upon gp120-CD4 binding. J Virol 1993; 67:3978-88.

Turk, B. E.; Huang, L. L.; Piro, E. T.; Cantley, L. C., *Nat Biotechnol* 2001, 19, (7), 661-7.

Van Cutsem, E.; Siena, S.; Humblet, Y.; Canon, J. L.; Maurel, J.; Bajetta, E.; Neyns, B.; Kotasek, D.; Santoro, A.; Scheithauer, W.; Spadafora, S.; Amado, R. G.; Hogan, N.; Peeters, M., *Ann Oncol* 2008, 19, (1), 92-8.

Vanhoefer, U.; Tewes, M.; Rojo, F.; Dirsch, O.; Schleucher, N.; Rosen, O.; Tillner, J.; Kovar, A.; Braun, A. H.; Trarbach, T.; Seeber, S.; Harstrick, A.; Baselga, J., *J Clin Oncol* 2004, 22, (1), 175-84.

Wen X, Wu Q P, Ke S, Ellis L, Charnsangavej C, Delpassand A S, Wallace S, Li C. Conjugation with (111)In-DTPA-poly(ethylene glycol) improves imaging of anti-EGF receptor antibody C225. J Nucl Med 2001; 42:1530-7.

Yan, L.; Hsu, K.; Beckman, R. A., *Cancer J.* 2008, 14, (3), 178-83.

Yarden Y, Sliwkowski M X. Untangling the ERBB signaling network. Nature Reviews Molecular Cell Biology 2001; 2:127-37.

Zhou, X.; Temam, S.; Oh, M.; Pungpravat, N.; Huang, B. L.; Mao, L.; Wong, D. T., *Neoplasia* 2006, 8, (11), 925-32.

What is claimed is:

1. A non-covalent masked antibody complex comprising:

(i) an antibody; and (ii) a protein A-protein L mask comprising:

(a) a protein A non-covalently bound to the heavy chain of the variable region of said antibody; and (b) a protein L non-covalently bound to the light chain of the variable region of said antibody; wherein said protein A and said protein L are bound together by a protease cleavable linker cleavable by a tumor-specific protease, wherein said antibody is alemtuzumab, bevacizumab, cetuximab, edrecolomab, gemtuzumab, ibritumomab tiuxetan, matuzumab, panitumumab, rituximab, or trastuzumab.

2. A pharmaceutical composition comprising a pharmaceutical excipient and the complex of claim 1.

3. A method of treating cancer, said method comprising administering a therapeutically effective amount of the complex of claim 1 to a subject in need thereof.

4. A non-covalently masked antibody complex comprising:

(i) an antibody; and (ii) a protein A-protein L mask comprising:

(a) a protein A bound to the heavy chain of the variable region of said antibody; and (b) a protein L bound to the light chain of the variable region of said antibody;

wherein said protein A and said protein L are bound together by a tumor associated protease MMP-9 linker comprising the amino acid sequence of SEQ ID NO:10; and wherein said antibody is alemtuzumab, bevacizumab, cetuximab, edrecolomab, gemtuzumab, ibritumomab tiuxetan, matuzumab, panitumumab, rituximab, or trastuzumab.

5. A pharmaceutical composition comprising (1) a non-covalently masked antibody complex comprising:

(i) an antibody; and (ii) a protein A-protein L mask comprising:

(a) a protein A bound to the heavy chain of the variable region of said antibody; and (b) a protein L bound to the light chain of the variable region of said antibody;

wherein said protein A and said protein L are bound together by a tumor associated protease MMP-9 linker comprising the amino acid sequence of SEQ ID NO:10; and wherein said antibody is trastuzumab;

and (2) a pharmaceutically acceptable carrier.

* * * * *